(12) United States Patent
Washburn, II et al.

(10) Patent No.: US 10,716,585 B2
(45) Date of Patent: Jul. 21, 2020

(54) CLOT EVACUATION AND VISUALIZATION DEVICES AND METHODS OF USE

(71) Applicant: TRICE MEDICAL, INC., King of Prussia, PA (US)

(72) Inventors: Richard H. Washburn, II, Wayne, PA (US); Alfred J. Intintoli, West Chester, PA (US); Richard T. Briganti, Philadelphia, PA (US)

(73) Assignee: Trice Medical, Inc., King of Prussia, PA (US)

( * ) Notice: Subject to any disclaimer, the term of this patent is extended or adjusted under 35 U.S.C. 154(b) by 576 days.

(21) Appl. No.: 15/461,994

(22) Filed: Mar. 17, 2017

(65) Prior Publication Data

US 2017/0265879 A1 Sep. 21, 2017

Related U.S. Application Data

(60) Provisional application No. 62/470,095, filed on Mar. 10, 2017, provisional application No. 62/309,918, filed on Mar. 17, 2016.

(51) Int. Cl.
*A61B 1/00* (2006.01)
*A61B 17/22* (2006.01)
(Continued)

(52) U.S. Cl.
CPC ...... *A61B 17/22012* (2013.01); *A61B 1/0002* (2013.01); *A61B 1/00009* (2013.01); *A61B 1/07* (2013.01); *A61B 1/126* (2013.01); *A61B 8/0891* (2013.01); *A61B 8/12* (2013.01); *A61B 17/22* (2013.01); *A61B 17/3478* (2013.01); *A61M 25/10* (2013.01); *A61B 17/34* (2013.01); *A61B 90/361* (2016.02); *A61B 90/37* (2016.02);
(Continued)

(58) Field of Classification Search
CPC ..... A61B 1/012; A61B 1/015; A61B 1/00098; A61B 1/00089; A61B 1/00091; A61B 1/00094; A61B 1/00096; A61B 1/00101
USPC ....... 600/104, 106–107, 153, 156, 158, 127, 600/129
See application file for complete search history.

(56) References Cited

U.S. PATENT DOCUMENTS

| 5,334,150 A | 8/1994 | Kaali |
| 5,395,312 A | 3/1995 | Desai |
(Continued)

FOREIGN PATENT DOCUMENTS

| CN | 106455907 A | 2/2017 |
| EP | 1553882 A1 | 7/2005 |
(Continued)

OTHER PUBLICATIONS

International Search Report dated Jul. 25, 2017 for International Application No. PCT/US2017/022794.

*Primary Examiner* — Matthew J Kasztejna
(74) *Attorney, Agent, or Firm* — Wilson Sonsini Goodrich & Rosati

(57) ABSTRACT

An integrated clot evacuation device having visualization for use in neurosurgical applications, particularly for the evacuation of clots formed as a result of intracranial hemorrhage (ICH). The device may further include an integrated camera and light for visualizing the interior of the brain and the clot itself. Further, the device is configured to evacuate clots through aspiration and irrigation.

6 Claims, 64 Drawing Sheets

(51) Int. Cl.
*A61B 1/07* (2006.01)
*A61B 1/12* (2006.01)
*A61B 8/08* (2006.01)
*A61B 8/12* (2006.01)
*A61B 17/34* (2006.01)
*A61M 25/10* (2013.01)
*A61B 90/00* (2016.01)
*A61B 17/00* (2006.01)
*A61B 17/32* (2006.01)
*A61B 34/20* (2016.01)

(52) U.S. Cl.
CPC ............... *A61B 2017/00871* (2013.01); *A61B 2017/00907* (2013.01); *A61B 2017/22062* (2013.01); *A61B 2017/22065* (2013.01); *A61B 2017/22072* (2013.01); *A61B 2017/22079* (2013.01); *A61B 2017/320044* (2013.01); *A61B 2017/320048* (2013.01); *A61B 2017/3456* (2013.01); *A61B 2034/2055* (2016.02); *A61B 2217/005* (2013.01); *A61B 2217/007* (2013.01); *A61M 2025/1084* (2013.01); *A61M 2210/0693* (2013.01); *A61M 2230/201* (2013.01)

(56) References Cited

U.S. PATENT DOCUMENTS

| | | | |
|---|---|---|---|
| 5,591,192 A | 1/1997 | Privitera et al. | |
| 5,607,443 A | 3/1997 | Kieturakis et al. | |
| 5,738,628 A | 4/1998 | Sierocuk et al. | |
| 5,817,123 A | 10/1998 | Kieturakis et al. | |
| 5,860,996 A | 1/1999 | Urban et al. | |
| 6,010,449 A | 1/2000 | Selmon et al. | |
| 6,178,346 B1 | 1/2001 | Amundson et al. | |
| 6,264,604 B1 | 7/2001 | Kieturakis et al. | |
| 6,632,234 B2 | 10/2003 | Kieturakis et al. | |
| 6,660,013 B2 | 12/2003 | Rabiner et al. | |
| 6,685,630 B2 | 2/2004 | Sauer et al. | |
| 6,740,102 B2 * | 5/2004 | Hess ............... A61B 17/00008 600/114 |
| 6,975,898 B2 | 12/2005 | Seibel | |
| 7,154,137 B2 | 12/2006 | Nozaki | |
| 7,161,130 B2 | 1/2007 | Manabe et al. | |
| 7,193,198 B2 | 3/2007 | Dai | |
| 7,196,314 B2 | 3/2007 | Rhodes | |
| 7,209,601 B2 | 4/2007 | Manabe | |
| 7,268,335 B2 | 9/2007 | Hiltunen | |
| 7,344,910 B2 | 3/2008 | Rhodes | |
| 7,345,330 B2 | 3/2008 | Rhodes | |
| 7,355,228 B2 | 4/2008 | Rhodes | |
| 7,368,772 B2 | 5/2008 | He et al. | |
| 7,388,242 B2 | 6/2008 | Yamamoto | |
| 7,699,839 B2 | 4/2010 | Balzano | |
| 7,717,853 B2 | 5/2010 | Nita | |
| 7,828,720 B2 | 11/2010 | Miller et al. | |
| 7,871,392 B2 | 1/2011 | Sartor | |
| 7,927,272 B2 | 4/2011 | Bayer et al. | |
| 7,931,659 B2 | 4/2011 | Bose et al. | |
| 8,206,315 B2 | 6/2012 | Mark et al. | |
| 8,230,867 B2 | 7/2012 | Mark | |
| 8,313,501 B2 | 11/2012 | Miller et al. | |
| 8,333,796 B2 | 12/2012 | Tompkins et al. | |
| 8,343,035 B2 | 1/2013 | To | |
| 8,357,175 B2 | 1/2013 | Mark | |
| 8,366,620 B2 | 2/2013 | Nita | |
| 8,366,735 B2 | 2/2013 | Bose et al. | |
| 8,409,083 B2 | 4/2013 | Mangiardi | |
| 8,430,825 B2 | 4/2013 | Mark | |
| 8,460,312 B2 | 6/2013 | Bose et al. | |
| 8,460,327 B2 | 6/2013 | Mark et al. | |
| 8,486,097 B2 | 7/2013 | Mark et al. | |
| 8,496,599 B2 | 7/2013 | Mark | |
| 8,584,853 B2 | 11/2013 | Knight et al. | |
| 8,608,650 B2 | 12/2013 | Mangiardi | |
| 8,657,841 B2 | 2/2014 | Mark | |
| 8,690,864 B2 | 4/2014 | Hoarau | |
| 8,702,738 B2 | 4/2014 | Mark | |
| 8,888,803 B2 | 11/2014 | Mark | |
| 8,903,476 B2 | 12/2014 | Brennan et al. | |
| 8,911,487 B2 | 12/2014 | Bennett et al. | |
| 8,986,334 B2 | 3/2015 | Mark et al. | |
| 9,028,518 B2 | 5/2015 | Mark | |
| 9,039,626 B2 | 5/2015 | Courtney | |
| 9,044,568 B2 | 6/2015 | Wilcox et al. | |
| 9,119,656 B2 | 9/2015 | Bose et al. | |
| 9,144,372 B2 | 9/2015 | Mark et al. | |
| 9,161,820 B2 | 10/2015 | Mark et al. | |
| 9,186,151 B2 | 11/2015 | Tompkins et al. | |
| 9,186,175 B2 | 11/2015 | Mark et al. | |
| 9,216,015 B2 | 12/2015 | Wilson | |
| 9,216,031 B2 | 12/2015 | Mark et al. | |
| 9,265,523 B2 | 2/2016 | Mark et al. | |
| 9,279,751 B2 | 3/2016 | Mark et al. | |
| 9,370,295 B2 | 6/2016 | Kienzle et al. | |
| 9,386,974 B2 | 7/2016 | Wilson | |
| 9,387,010 B2 | 7/2016 | Mark et al. | |
| 9,445,831 B2 | 9/2016 | Mark et al. | |
| 9,610,007 B2 | 4/2017 | Kienzle et al. | |
| 2003/0040753 A1 | 2/2003 | Daum et al. | |
| 2004/0254422 A1 * | 12/2004 | Singh ................... A61B 1/0008 600/160 |
| 2005/0014995 A1 | 1/2005 | Amundson et al. | |
| 2005/0020914 A1 | 1/2005 | Amundson et al. | |
| 2005/0154262 A1 | 7/2005 | Banik et al. | |
| 2005/0222499 A1 | 10/2005 | Banik et al. | |
| 2006/0058837 A1 | 3/2006 | Bose et al. | |
| 2006/0206118 A1 | 9/2006 | Kim et al. | |
| 2007/0038100 A1 | 2/2007 | Nita | |
| 2007/0083100 A1 | 4/2007 | Schulz-Stubner | |
| 2007/0129652 A1 | 6/2007 | Nita | |
| 2007/0239261 A1 | 10/2007 | Bose et al. | |
| 2007/0260273 A1 | 11/2007 | Cropper et al. | |
| 2008/0015478 A1 | 1/2008 | Bose | |
| 2008/0109026 A1 | 5/2008 | Kassam | |
| 2008/0167527 A1 * | 7/2008 | Slenker ............... A61B 1/00091 600/156 |
| 2008/0319355 A1 | 12/2008 | Nita | |
| 2009/0030400 A1 | 1/2009 | Bose et al. | |
| 2009/0281386 A1 * | 11/2009 | Acosta ............... A61B 17/3421 600/114 |
| 2010/0081873 A1 | 4/2010 | Tanimura et al. | |
| 2010/0121139 A1 | 5/2010 | Ouyang et al. | |
| 2010/0121142 A1 | 5/2010 | Ouyang et al. | |
| 2010/0152762 A1 | 6/2010 | Mark | |
| 2010/0204672 A1 | 8/2010 | Lockhart et al. | |
| 2010/0284580 A1 | 11/2010 | Ouyang et al. | |
| 2010/0286477 A1 | 11/2010 | Ouyang et al. | |
| 2011/0040145 A1 | 2/2011 | Miller et al. | |
| 2011/0160621 A1 | 6/2011 | Nita | |
| 2011/0160757 A1 | 6/2011 | Ferrera et al. | |
| 2011/0184454 A1 | 7/2011 | Barry et al. | |
| 2011/0276113 A1 | 11/2011 | Cybulski | |
| 2011/0313328 A1 | 12/2011 | Nita | |
| 2011/0319927 A1 | 12/2011 | Nita | |
| 2012/0029354 A1 | 2/2012 | Mark et al. | |
| 2012/0071748 A1 | 3/2012 | Mark et al. | |
| 2012/0078140 A1 | 3/2012 | Nita | |
| 2012/0078279 A1 | 3/2012 | Mark | |
| 2012/0078285 A1 | 3/2012 | Griffin | |
| 2012/0095458 A1 | 4/2012 | Cybulski et al. | |
| 2012/0116440 A1 | 5/2012 | Leynov et al. | |
| 2012/0150147 A1 | 6/2012 | Leynov et al. | |
| 2012/0226150 A1 | 9/2012 | Balicki et al. | |
| 2012/0289816 A1 | 11/2012 | Mark et al. | |
| 2012/0330196 A1 | 12/2012 | Nita | |
| 2013/0102851 A1 | 4/2013 | Mark et al. | |
| 2013/0130359 A1 | 5/2013 | Mark et al. | |
| 2013/0158578 A1 | 6/2013 | Ghodke et al. | |
| 2013/0204287 A1 | 8/2013 | Mark et al. | |
| 2013/0237753 A1 | 9/2013 | Mark et al. | |
| 2013/0245374 A1 | 9/2013 | Kunz et al. | |
| 2013/0261730 A1 | 10/2013 | Bose et al. | |

(56) References Cited

U.S. PATENT DOCUMENTS

| | | |
|---|---|---|
| 2013/0324976 A1 | 12/2013 | Mark |
| 2014/0012083 A1* | 1/2014 | Chin .................. A61B 1/00154 600/114 |
| 2014/0017771 A1 | 1/2014 | Mark et al. |
| 2014/0066929 A1 | 3/2014 | Mark et al. |
| 2014/0066930 A1 | 3/2014 | Mark et al. |
| 2014/0128907 A1 | 5/2014 | Hui et al. |
| 2014/0163547 A1 | 6/2014 | Mark et al. |
| 2014/0171873 A1 | 6/2014 | Mark |
| 2014/0180377 A1 | 6/2014 | Bose et al. |
| 2014/0187922 A1 | 7/2014 | Mark et al. |
| 2014/0276024 A1 | 9/2014 | Stigall et al. |
| 2014/0277046 A1 | 9/2014 | Mark et al. |
| 2014/0324080 A1 | 10/2014 | Wallace |
| 2014/0358175 A1 | 12/2014 | Tompkins et al. |
| 2015/0031126 A1 | 1/2015 | Mark et al. |
| 2015/0032025 A1 | 1/2015 | Mark et al. |
| 2015/0038902 A1 | 2/2015 | Mark et al. |
| 2015/0066019 A1 | 3/2015 | Mark et al. |
| 2015/0073524 A1 | 3/2015 | Bennett et al. |
| 2015/0112324 A1 | 4/2015 | Cybulski |
| 2015/0150583 A1 | 6/2015 | Mark et al. |
| 2015/0157387 A1 | 6/2015 | Ouyang et al. |
| 2015/0190159 A1 | 7/2015 | Mark et al. |
| 2015/0196193 A1 | 7/2015 | Kienzle et al. |
| 2015/0196197 A1 | 7/2015 | Kienzle et al. |
| 2015/0196304 A1 | 7/2015 | Rabkin et al. |
| 2015/0196309 A1 | 7/2015 | Matsubara et al. |
| 2015/0196315 A1 | 7/2015 | Mark |
| 2015/0209101 A1 | 7/2015 | Mark et al. |
| 2015/0257745 A1 | 9/2015 | Mangiardi et al. |
| 2015/0289865 A1 | 10/2015 | Novak et al. |
| 2015/0297097 A1 | 10/2015 | Matsubara et al. |
| 2015/0297311 A1 | 10/2015 | Tesar |
| 2015/0313634 A1 | 11/2015 | Gross et al. |
| 2015/0366574 A1 | 12/2015 | Kovarik et al. |
| 2015/0374222 A1 | 12/2015 | Mark et al. |
| 2016/0015374 A1 | 1/2016 | Gifford et al. |
| 2016/0015471 A1 | 1/2016 | Piron et al. |
| 2016/0045224 A1 | 2/2016 | Hendershot, III |
| 2016/0066944 A1 | 3/2016 | Mark et al. |
| 2016/0095623 A1 | 4/2016 | Mark et al. |
| 2016/0128720 A1 | 5/2016 | Mark et al. |
| 2016/0128722 A1 | 5/2016 | Mark et al. |
| 2016/0135800 A1 | 5/2016 | Novak et al. |
| 2016/0166265 A1 | 6/2016 | Nita |
| 2016/0166266 A1 | 6/2016 | Nita |
| 2016/0206348 A1 | 7/2016 | Wilson |
| 2016/0249999 A1 | 9/2016 | Wilson |
| 2016/0317182 A1 | 11/2016 | Mark et al. |
| 2017/0042408 A1 | 2/2017 | Washburn et al. |
| 2017/0086666 A1 | 3/2017 | Kienzle et al. |

FOREIGN PATENT DOCUMENTS

| | | |
|---|---|---|
| EP | 2335550 A2 | 6/2011 |
| EP | 3094231 A1 | 11/2016 |
| WO | WO-2008094436 A1 | 8/2008 |
| WO | WO-2008094439 A2 | 8/2008 |
| WO | WO-2008094444 A2 | 8/2008 |
| WO | WO-2009029639 A1 | 3/2009 |
| WO | WO-2014137530 A1 | 9/2014 |
| WO | WO-2015074045 A2 | 5/2015 |
| WO | WO-2016014819 A1 | 1/2016 |
| WO | WO-2016142749 A1 | 9/2016 |
| WO | WO-2017027749 A1 | 2/2017 |
| WO | WO-2017161177 A1 | 9/2017 |

\* cited by examiner

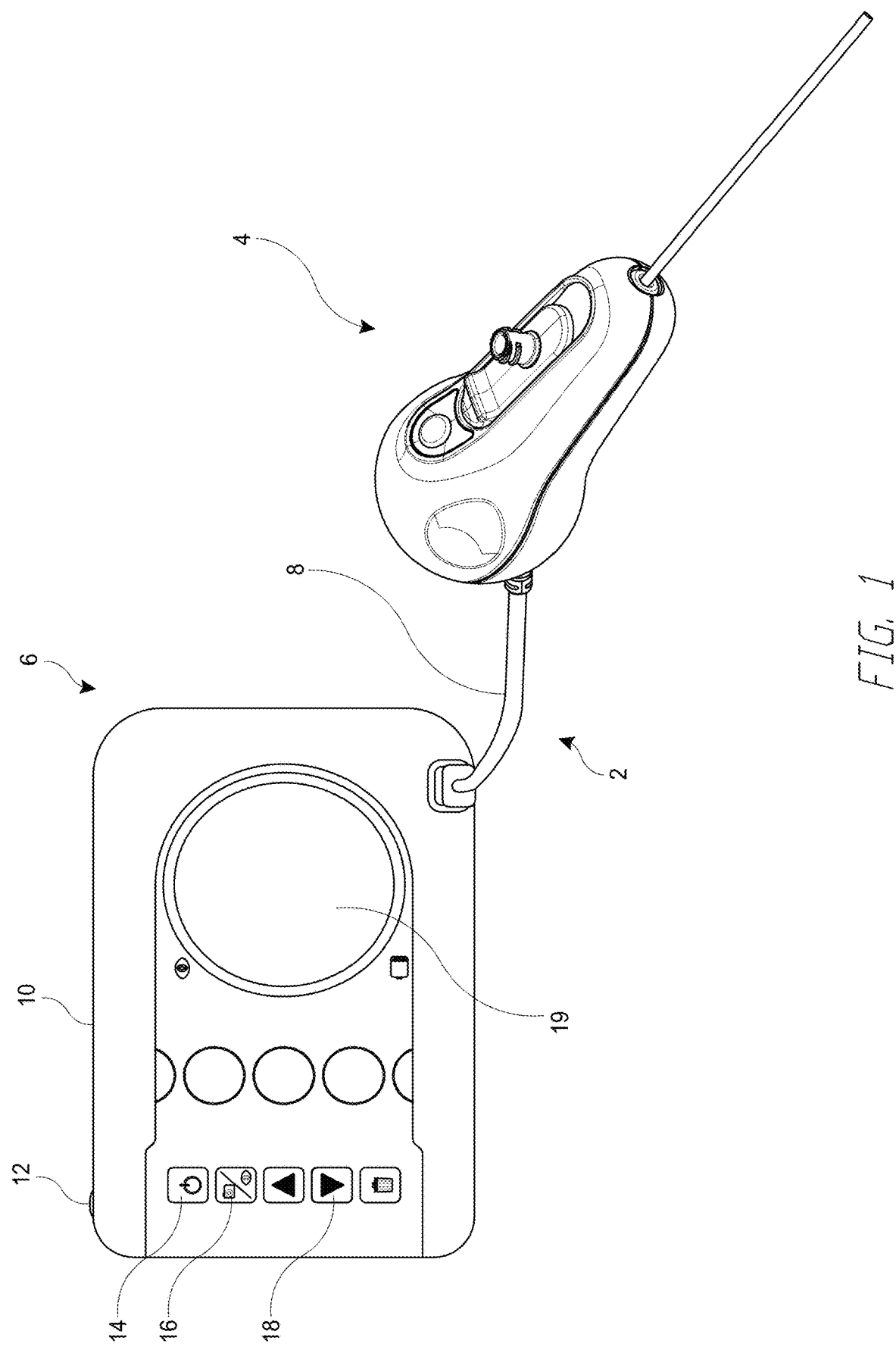

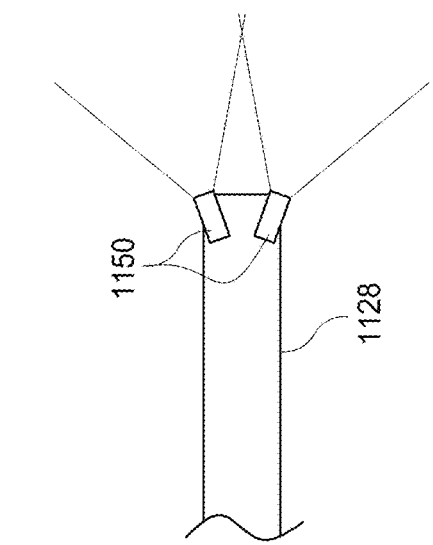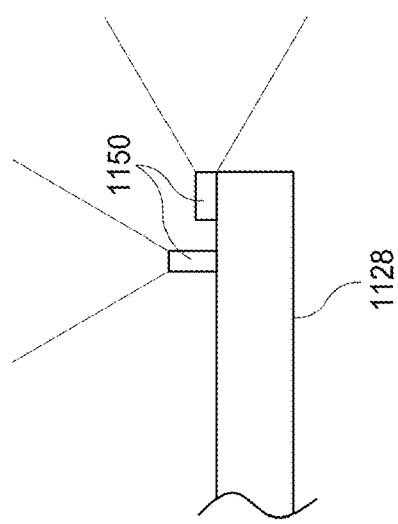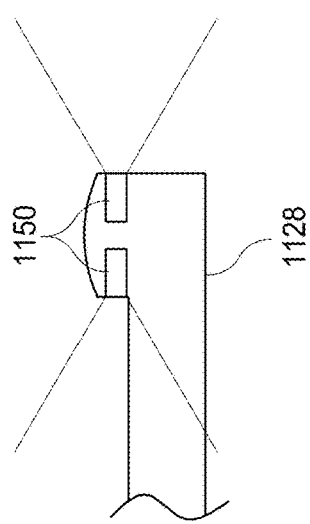
FIG. 3F

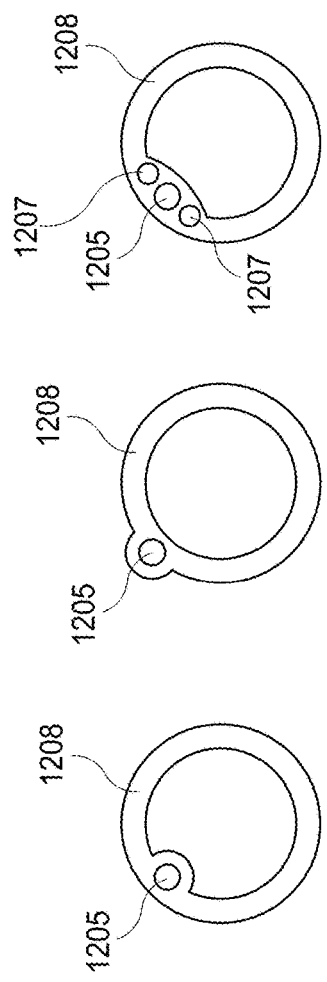
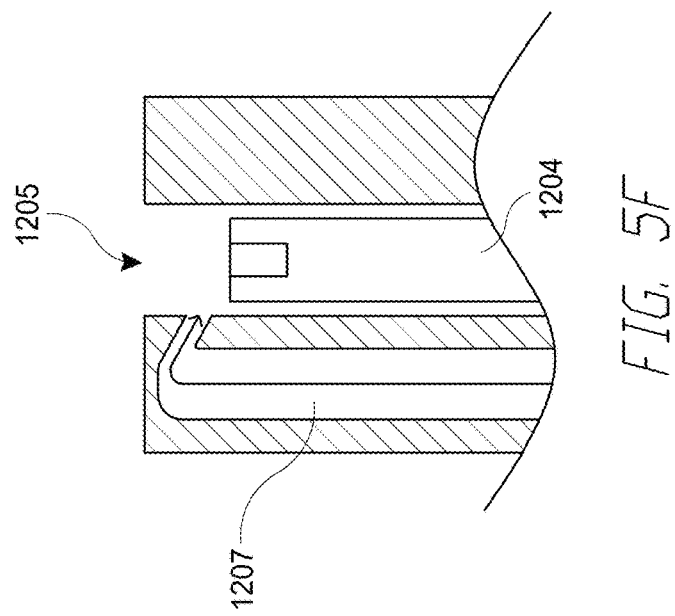
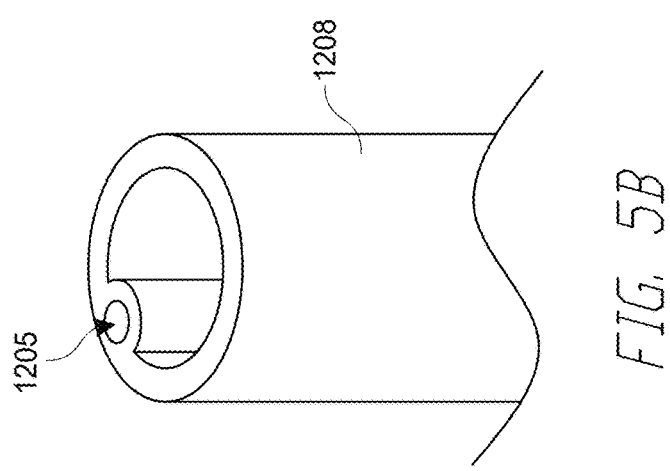
FIG. 5E
FIG. 5D
FIG. 5C
FIG. 5F
FIG. 5B

Without Anti-rotation view
User rotates portion of scope where camera is housed
↓
Rotating camera causes image on monitor to rotate
↓
User can lose rotational orientation
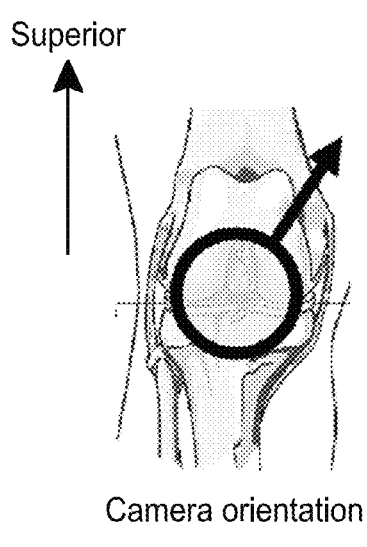
Camera orientation
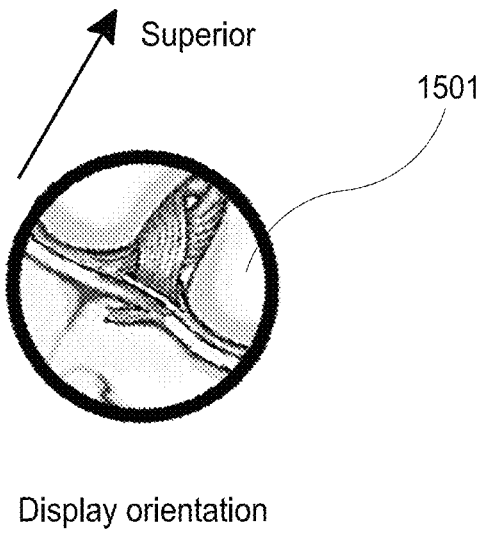
Display orientation
FIG. 8A

With Anti-rotation view
User rotates portion of scope where camera sensor is housed
↓
Sensor determines angular rotation of camera
↓
Sensor/software maintains image on screen relative to patient orientation
↓
User maintains rotational orientation
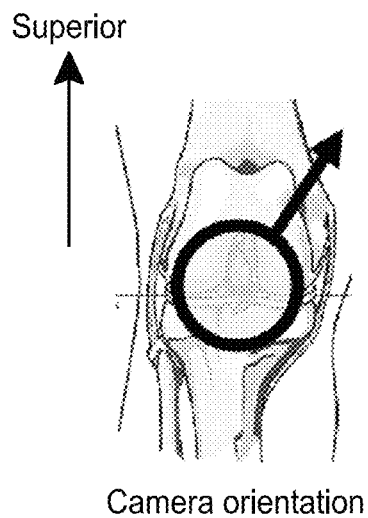
Superior ↑
Camera orientation
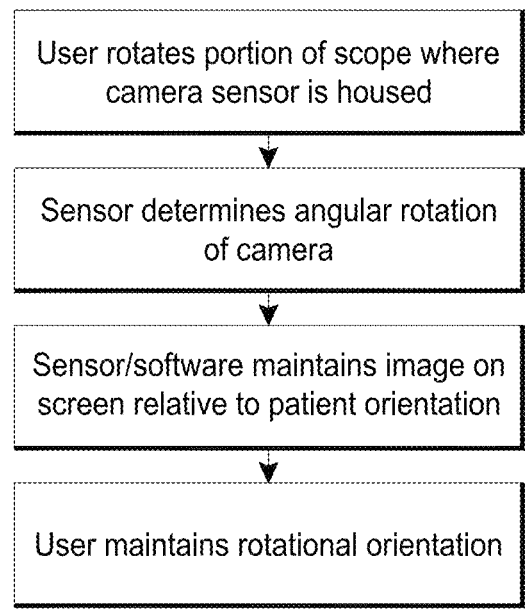
Superior ↑
1503
Display orientation
FIG. 8B Section A-A 5 mm 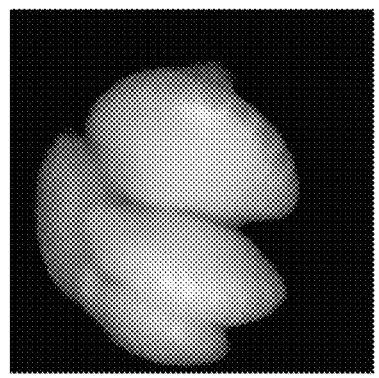 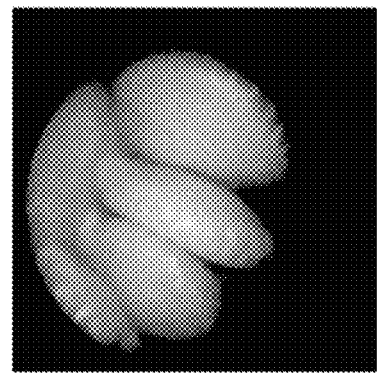
25 mm 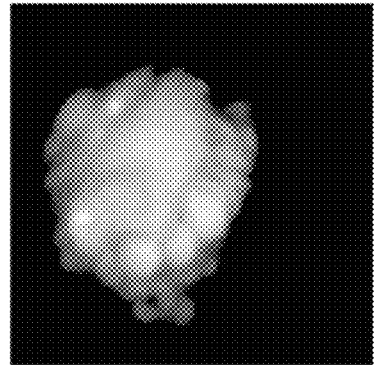 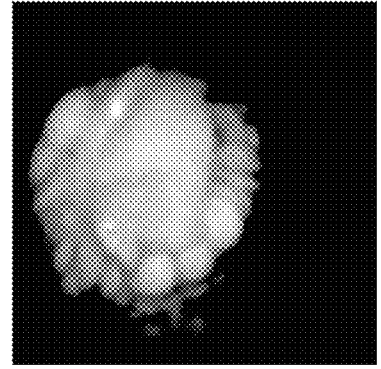
FIG. 10

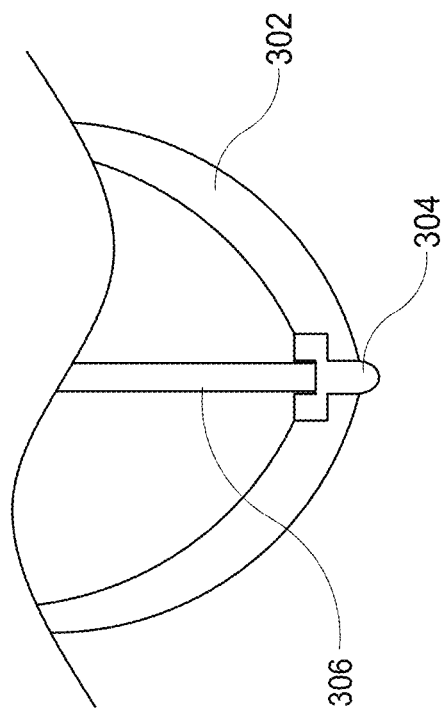
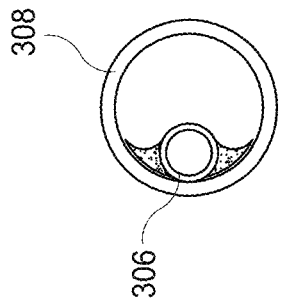
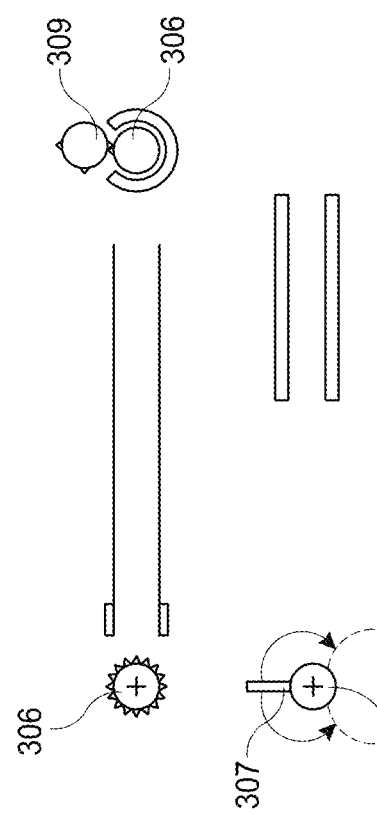
FIG. 12B
FIG. 12C
FIG. 12D

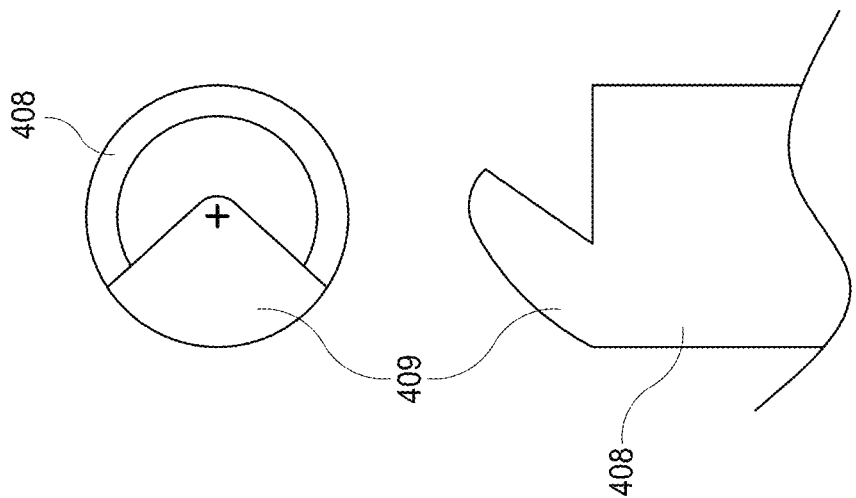
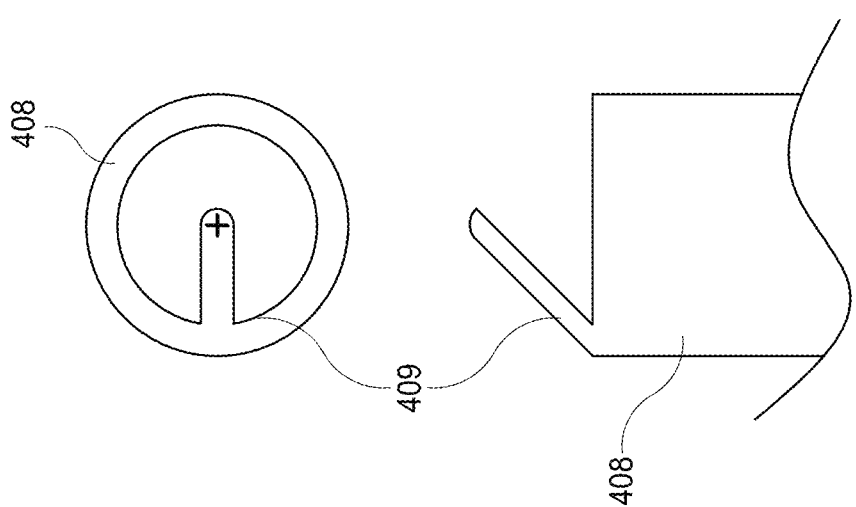
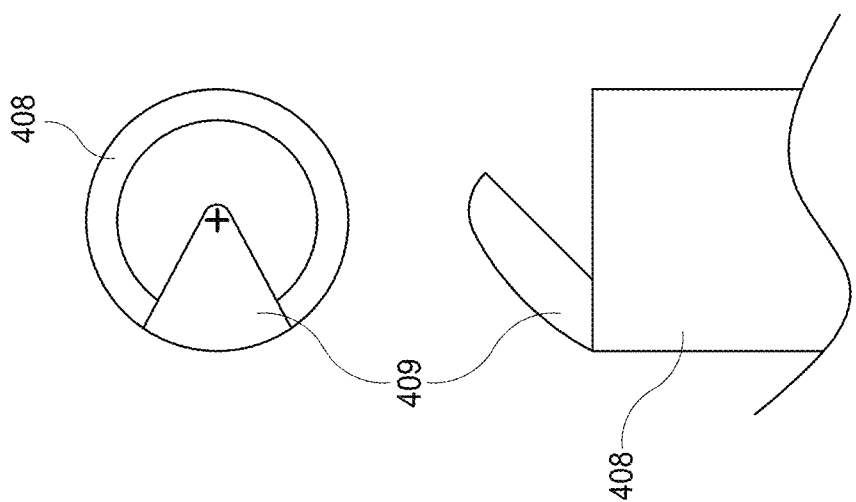
FIG. 17

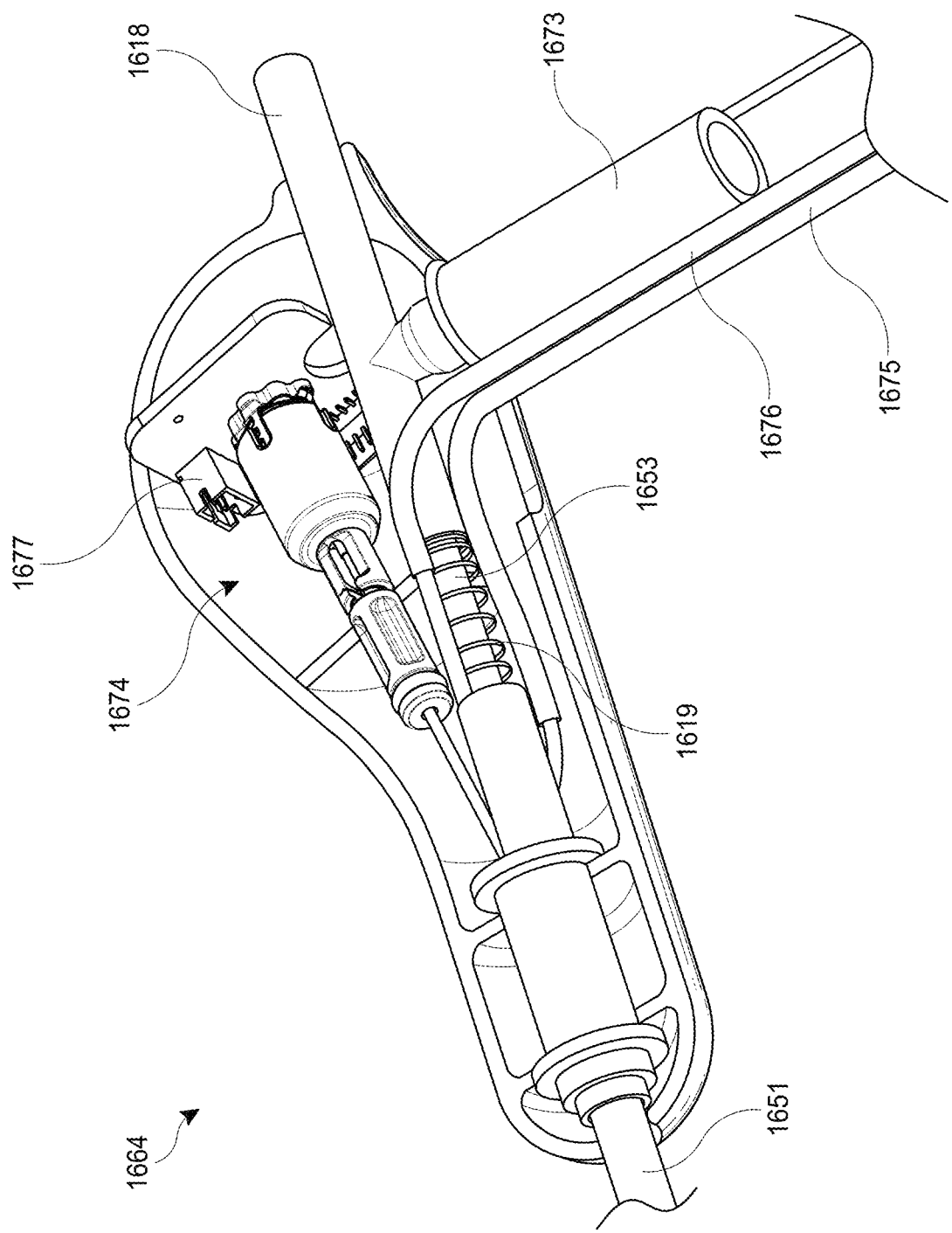

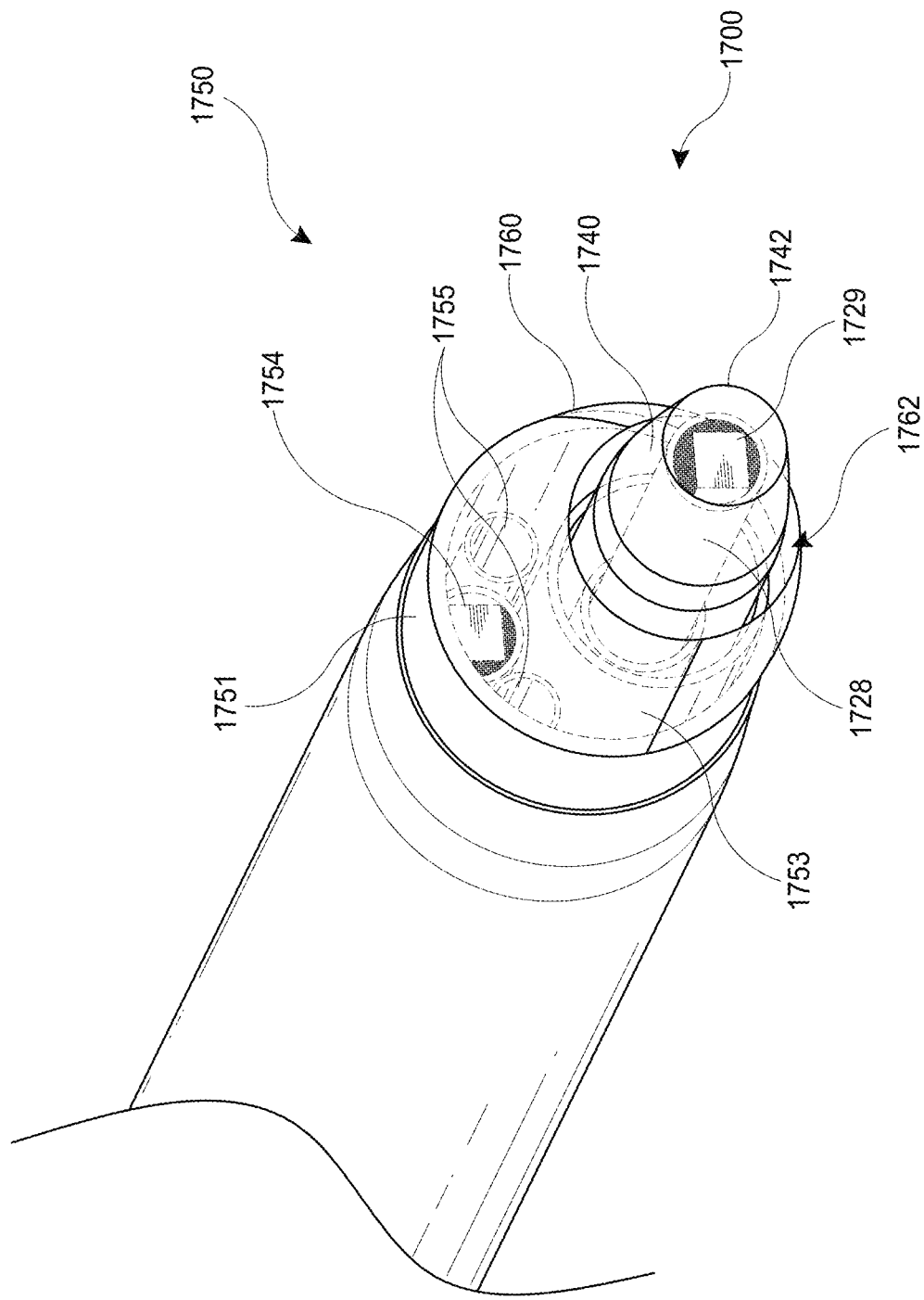

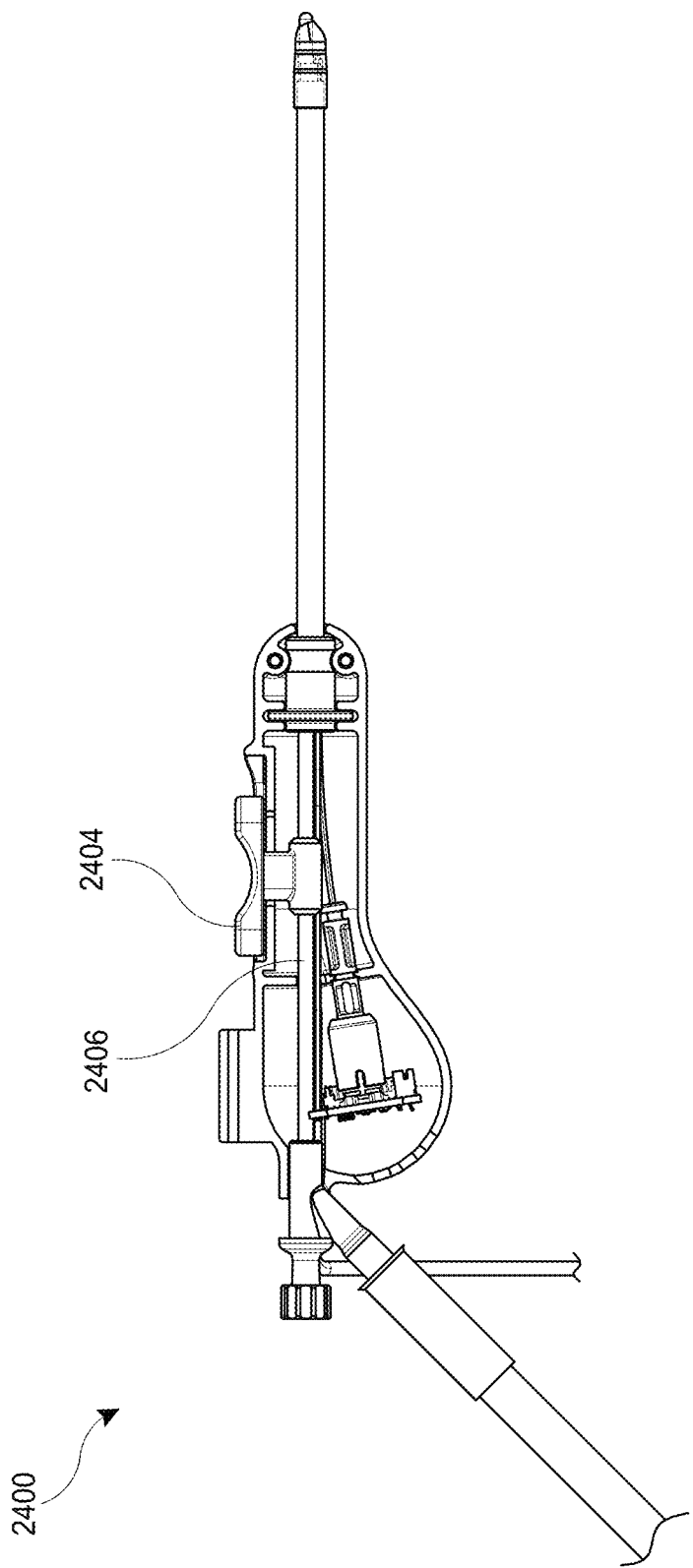

CLOT EVACUATION AND VISUALIZATION DEVICES AND METHODS OF USE

INCORPORATION BY REFERENCE

This application claims priority benefit of U.S. Provisional Patent Application No. 62/309,918, filed Mar. 17, 2016, and U.S. Provisional Patent Application No. 62/470,095, filed Mar. 10, 2017, each of which is incorporated herein by reference in its entirety for all purposes. Any and all applications related thereto by way of priority thereto or therefrom are hereby incorporated by reference in their entirety.

BACKGROUND OF THE INVENTION

Field of the Invention

This application describes embodiments of apparatuses, methods, and systems for the evacuation of clots, particularly for neurosurgical applications such as the treatment of intracranial hemorrhage (ICH).

Description of the Related Art

Intracranial hemorrhage (ICH) is bleeding that occurs inside the skull, a serious medical emergency that may crush delicate brain tissue, limit the brain's blood supply and cause potentially deadly brain herniation in which parts of the brain are squeezed past structures in the skull. ICH may occur when a blood vessel ruptures within the brain or between the skull and the brain. Hemorrhaged blood may collect into a blood clot, potentially impacting circulation in the brain, resulting in cell death. Therefore removing or reducing hemorrhaged blood and/or blood clots in the brain is crucial to patient recovery.

Removal of a blood clot may be performed via aspiration of the clot, such as with a catheter, or via other means such as a craniotomy. During a craniotomy, neurosurgeons open a significant portion of the skull to provide access for directly visualizing blood clots to distinguish from brain tissue and be able to safely remove the blood clots. However, such surgeries are high risk with a long recovery time. Therefore, there is a need for improved methods and tools to provide ease of navigation, visualization, and removal of blood clots.

SUMMARY OF THE INVENTION

Embodiments of the present disclosure relate to devices, methods, and systems for providing clot evacuation and visualization for use in neurosurgical applications, particularly for the evacuation of clots formed as a result of intracranial hemorrhage (ICH). Certain embodiments involve an integrated clot evacuation device having visualization. In some embodiments, the integrated clot evacuation devices comprise a visualization sensor and an elongated body having a proximal end and a distal end. The distal end of the elongated body may be dimensioned to pass through an opening into the body, such as a minimally invasive body opening. The device may include an integrated camera and light for visualizing the interior of the brain and the clot itself. In certain embodiments, the device may further comprise an integrated articulation mechanism that imparts steerability to at least one of the visualization sensor and the distal end of the elongated body. Further, the device may be configured to evacuate clots through aspiration and irrigation.

In certain embodiments, an integrated clot evacuation device, comprises:
 a handpiece;
 an elongate body, extending along a longitudinal axis between a proximal end affixed to the handle, and a distal end;
 a visualization element positioned along or within the elongate body configured to visualize tissue and/or blood clots; and
 a lumen extending along at least part of the length of the elongate tubular body, the lumen configured to provide aspiration and/or irrigation for the removal of clots through the lumen.

In certain embodiments, the integrated clot evacuation device further comprises an illumination element. The visualization element may be a hypotube positioned concentrically or non-concentrically within the elongate body. The visualization element may be configured to vibrate. In some embodiments, the elongate body may be configured to rotate relative to the visualization element. The visualization element may be retractable or extendable within the elongate body. The lumen may be configured to provide irrigation to the visualization element. In certain embodiments, the distal end of the elongate body may comprise a clear, conically shaped tip configured to provide visualization of tissues as the integrated clot evacuation device is moved to a clot. The conically shaped tip can be configured to open and allow the distal end of the tubular body and/or the visualization element to extend outward toward the tissue site. In embodiments, the integrated clot evacuation device may further comprise a tube extending the length of the elongate body, the tube configured to provide aspiration and irrigation. In certain embodiments, the integrated clot evacuation device may further comprise a source of infrared illumination. For example, the infrared light may be supplied in the form of an illumination fiber. The integrated clot evacuation device may comprise an ultrasonic transducer. In embodiments, the integrated clot evacuation device can comprise a glucose sensor.

In certain embodiments, the visualization element may be retractable or extendable within the elongate body and likewise the elongate body may be retractable and extendable with the visualization element remaining in position. The lumen may be configured to provide irrigation to the visualization element. In certain embodiments, an outer sleeving, overlapping the rigid tubular body, provides a second path for irrigation. In some embodiments the irrigation is directed toward the visualization element. The elongate body may comprise a perforated path for irrigation to help with the evacuation of clots. In some embodiments, the outer sleeving may also extend over the distal end of the elongate body providing a means for introducing the device through tissue with minimal disruption of tissue. In embodiments the outer sleeving can be retracted to allow visualization of tissue and a path for irrigation of the visual element.

In some embodiments, the visualization element may be configured to be retractable within an outer tubular body and/or a suction channel. In certain embodiments, irrigation may be directed to clean the lens of the visualization element by utilizing an arrangement of optics and irrigation elements configured to direct the irrigation. The elongate tubular body may be retractable or extendable relative to the visualization element. In particular embodiments, the integrated clot evacuation device may further comprise a second irrigation port in fluid communication with an outer sleeve, the outer sleeve overlapping the elongate tubular body and configured to provide irrigation to the visualization element. In embodiments, the elongate body may be perforated to allow irrigation from the overlapping outer sleeve to aid the suction and evacuation of the clot. The outer sleeve may extend and close over the distal end of the tubular body to provide for less disruptive insertion of the device into the soft tissue. In certain embodiments, the elongate tubular body may be rigid. In some embodiments, the elongate tubular body may be flexible.

In some embodiments, a method of evacuating a clot may comprise:
- delivering an integrated clot evacuation device to a location adjacent a clot within a brain of a patient, the integrated clot evacuation device comprising an elongate body extending along a longitudinal axis between a proximal end and a distal end, wherein the distal end is positioned adjacent the clot;
- visualizing tissue and/or the blood clot utilizing a visualization element integrated into the clot evacuation device and positioned along or within the elongate body; and
- removing the clot utilizing aspiration and/or irrigation through an opening at or near the distal end and through a lumen of the clot evacuation device.

In certain embodiments, the visualization element may vibrate while removing the clot. In certain embodiments, the elongate body comprises an outer tubular body that rotates relative to the visualization element while removing the clot. In some embodiments, the visualization element is retractable or extendable within the elongate body. Irrigation may be provided through the lumen to the visualization element. The distal end of the elongate body may comprises a clear, conically shaped tip, configured to provide visualization of tissues as the integrated clot evacuation device is moved into a clot.

In certain embodiments, an evacuation device includes an elongate body having a proximal end and a distal end, a visualization element located at or near the distal end of the elongate body for transmitting images received from inside of a patient, and an obturator. The elongate body includes one or more lumens, including an evacuation lumen extending along at least part of the length of the elongate body. The elongate body further includes a distal opening in fluid communication with the evacuation lumen at or near the distal end of the elongate body. The obturator is configured to be removably inserted in the evacuation lumen and to close off the distal opening.

In certain embodiments, a method of evacuating a clot, tissue, and/or fluid comprises delivering an evacuation device to the clot, tissue, and/or fluid with an obturator inserted into an evacuation lumen of the evacuation device, visualizing the clot, tissue, and/or fluid utilizing a visualization element positioned on or within the evacuation device, removing the obturator from the evacuation lumen of the evacuation device, and applying suction to the evacuation lumen of the evacuation device to evacuate at least a portion of the clot, tissue, and/or fluid.

In certain embodiments, a surgical device for creating an access path to an internal region of a body of a patient includes an outer tubular body having a proximal end and a distal end, a visualization element, one or more instruments for performing an operation, an introducer, and a shielding member. The visualization element is located within the outer tubular body and has a distal end positioned at or near the distal end of the outer tubular body for transmitting images received from inside the body of the patient. The one or more instruments are located within the outer tubular body and has a distal end positioned at or near the distal end of the outer tubular body for performing an operation within the body of the patient. The introducer has an elongate body with a proximal end and a distal end, the distal end of the introducer having an atraumatic tip. The introducer is sized and configured to be removably received within the outer tubular body. The shielding member is coupled to either the distal end of the outer tubular body or the distal end of the elongate body of the introducer. The shielding member has a proximal side and a distal side and is configured to at least partially close off the distal end of the outer tubular body such that the shielding member at least partially shields the distal end of the visualization element. The shielding member is configured to at least partially surround a portion of the distal end of the elongate body of the introducer such that the atraumatic tip may be positioned distally of the distal side of the shielding member.

In certain embodiments, a surgical device for creating an access path to an internal region of a body of a patient includes an outer tubular body, a visualization element, one or more instruments for performing an operation, an introducer, and a balloon. The outer tubular body has a proximal end and a distal end. The visualization element is located within the outer tubular body and has a distal end positioned at or near the distal end of the outer sheath for transmitting images received from inside the body of the patient. The one or more instruments for performing an operation within the body of the patient is located within the outer tubular body and has a distal end positioned at or near the distal end of the outer tubular body. The introducer has an elongate body with a proximal end and a distal end, the distal end having an atraumatic tip. The introducer is sized and configured to be removably received within the outer tubular body. The balloon is joined to the distal end of the elongate body of the introducer and has an interior surface and an exterior surface. The balloon has an inflated configuration and a deflated configuration. The introducer further includes a passage extending from its proximal end to an aperture in a sidewall of the distal end of its elongate body, the aperture being in fluid communication with an interior of the balloon defined by an air-tight seal between the interior surface of the balloon and the elongate body. The balloon is configured to be inflated after insertion of the introducer into the outer tubular body such that in its inflated configuration it at least partially closes off the distal end of the outer tubular body and in doing so at least partially shields the distal end of the visualization element. The balloon is configured in its inflated configuration to at least partially surround a portion of the distal end of the elongate body of the introducer such that at least a portion the atraumatic tip may be positioned distally of the balloon. The balloon is configured to be deflated prior to removal of the introducer from the outer tubular body.

In certain embodiments, a method of removing a clot formed as a result of intracranial hemorrhage from the brain, comprises placing an optical introducer through the skull of a patient to the location of the clot. The optical introducer includes an elongate tube having a proximal end and a distal end, wherein the distal end is covered by a transparent window. A visualization element is contained within the elongate tube to assist in placing the optical introducer to the location of the clot. The method further comprises guiding an outer cannula to the location of the clot using the optical introducer. The outer cannula is guided to the location of the clot either simultaneously with the optical introducer or subsequently delivered over the optical introducer. The method further comprises removing the optical introducer from the outer cannula, leaving the outer cannula in place within the skull, delivering a clot evacuation device through the outer cannula to the location of the clot, and removing the clot through the clot evacuation device.

In certain embodiments, a method of removing a clot formed as a result of intracranial hemorrhage from the brain comprises inserting a combined introducer and clot evacuation device through the skull of a patient to the location of the clot. The combined introducer and clot evacuation device includes an introducer having an elongate body. The elongate body of the introducer has a proximal end and a distal end, the distal end having an atraumatic tip. The clot evacuation device includes an outer tubular body having a proximal end and a distal end. One or more operational elements are disposed within the outer tubular body. The outer tubular body removably receives the introducer, such that the atraumatic tip of the introducer extends beyond the distal end of the outer tubular body. The clot evacuation device further includes a shielding member joined or joinable to either the distal end of the outer tubular body of the clot evacuation device or the distal end of the elongate body of the introducer. The shielding member at least partially closes off the distal end of the outer tubular body. During insertion of the combined introducer and clot evacuation device, the one or more operational elements are shielded by the shielding member and/or introducer from contacting bodily tissue. The method further comprises removing the introducer from the clot evacuation device, leaving the clot evacuation device in place within the skull, and employing the one or more operational elements of the clot evacuation device to remove the clot through the clot evacuation device.

In certain embodiments, a method of removing a clot formed as a result of intracranial hemorrhage from the brain comprises placing a clot evacuation device through the skull of a patient to the location of the clot. The clot evacuation device includes an outer tubular body having a proximal end and a distal end. One or more operational elements are disposed within the outer tubular body. A visualization element for transmitting images received from inside a skull of a patient is located in the outer tubular body. An atraumatic tip is removably attached to the distal end of the outer tubular body, wherein at least a portion of the atraumatic tip is at least partially transparent to allow for the visualization element to receive images through the atraumatic tip. The atraumatic tip is configured to prevent the one or more operational elements from contacting body tissue when the atraumatic tip is attached to the clot evacuation device. The method further comprises visualizing images from inside the skull of the patient while the clot evacuation device is being placed via the visualization element. The method further comprises guiding an outer cannula to the location of the clot using the clot evacuation device, wherein the outer cannula is guided to the location of the clot either simultaneously with the clot evacuation device or subsequently delivered over the outer tubular body. The method further comprises removing the clot evacuation device from the body, removing the atraumatic tip from the distal end of the outer tubular body of the clot evacuation device, and reinserting the clot evacuation device through the outer cannula to the location of the clot. The method further comprises employing the one or more operational elements of the clot evacuation device to remove the clot through the clot evacuation device.

In certain embodiments, a surgical device for creating an access path to an internal region of a body of a patient includes an outer tubular body having a proximal end and a distal end, a visualization element, an atraumatic tip removably attachable to the distal end of the outer tubular body, and one or more instruments for performing an operation within the body of the patient. The visualization element is located within the outer tubular body and has a distal end positioned at or near the distal end of the outer tubular body for transmitting images received from inside the body of the patient. The one or more instruments are located within the outer tubular body and has a distal end positioned at or near the distal end of the outer tubular body. At least a portion of the atraumatic tip is at least partially transparent to allow for the visualization element to receive images through the atraumatic tip. The atraumatic tip closes off the distal end of the outer tubular body to prevent the one or more instruments from contacting body tissue when the atraumatic tip is attached to the surgical device. The atraumatic tip forms an atraumatic distal end on the surgical device such that the surgical device may be atraumatically inserted into the body of the patient to a location where the operation is to be performed.

In certain embodiments, a method of performing a visually guided minimally invasive operation within the body of a patient comprises attaching a shielding member to an endoscope. The endoscope has an elongate body having a proximal end and a distal end, a visualization element for transmitting images received from inside the body, and a working channel extending through the elongate body from the proximal end to the distal end. The working channel of the endoscope is configured to removably receive one or more operational instruments for operating within the body. The shielding member is at least partially transparent and has a proximal side and a distal side. The shielding member is configured to removably attach to the distal end of the elongate body of the endoscope. The shielding member comprises a hole extending from its proximal side to its distal side for receiving an introducer. The method further comprises inserting an introducer through the working channel of the endoscope either before or after the shielding member is attached. The introducer has an elongate body having a proximal end and a distal end, the distal end of the introducer having an atraumatic tip. The introducer is configured to be removably received within the working channel of the endoscope such that the atraumatic tip extends distally of the distal end of the endoscope. The method further comprises positioning the introducer within the endoscope such that at least a portion of the elongate body of the introducer passes from the proximal side of the shielding member to the distal side of the shielding member and such that at least a portion of the atraumatic tip is positioned distally of the shielding member. The method further comprises placing the endoscope into the body of the patient to a location where the operation is to be performed while visualizing images from inside the body of the patient via the visualization element of the endoscope. The shielding member shields the visualization element of the endoscope such that the visualization element is prevented from contacting body tissue during use. The visualization element receives images from inside the body through the at least partially transparent portion of the shielding member. The method further comprises removing the introducer from the endoscope while the endoscope remains in place within the body, inserting the one or more operational instruments through the working channel such that they extend to or through the hole in the shielding member, and employing the one or more operational instruments to perform the operation while visualizing images from inside the body via the visualization element of the endoscope. The method further comprises removing the operational instruments from the working channel of the endoscope and removing the endoscope from the body either simultaneously with the operational instruments or subsequently to the removal of the operational instruments from the working channel of the endoscope.

In certain embodiments, a kit for adapting an endoscope to perform a visually guided minimally invasive operation within the body of a patient includes a shielding member and an introducer. The shielding member is configured to be removably attached to the distal end of an endoscope having a proximal end and the distal end, a working channel extending from the proximal end to the distal end for receiving one or more operational instruments for performing an operation in the body, and a visualization element for transmitting images received from inside the body. The shielding member is configured to shield the visualization element of the endoscope in an attached configuration such that the visualization element is prevented from contacting body tissue during use. A portion of the shielding member is at least partially transparent at a location configured to allow visualization by the visualization element of the endoscope through the partially transparent portion of the shielding member in the attached configuration. The shielding member has a proximal side, a distal side, and a hole extending from its proximal side to its distal side for receiving an introducer. The introducer is configured to be removably inserted through the working channel of the endoscope. The introducer has an elongate body having a proximal end and a distal end, the distal end of the introducer having an atraumatic tip. The introducer is configured to be removably received within the working channel of the endoscope such that the atraumatic tip extends distally of the distal end of the endoscope. The introducer is configured to be removably received within the hole of the shielding member in the attached configuration such that at least a portion of the elongate body of the introducer passes from the proximal side of the shielding member to the distal side of the shielding member and such that at least a portion of the atraumatic tip is positioned distally of the shielding member.

Additional embodiments of clot evacuation devices (with or without integrated visualization), introducers, trocars, and other devices, and their methods of use, are described below.

BRIEF DESCRIPTION OF THE DRAWINGS

Other features and advantages of the embodiments described herein will be apparent from the following detailed description of the invention, taken in conjunction with the accompanying drawings of which:

FIG. 1 illustrates an embodiment of a clot evacuation system.

FIGS. 3A-F illustrate views of embodiments of the clot evacuation device illustrated in FIG. 2A.

FIGS. 5A-M illustrate views and descriptions of embodiments of a tubular portion of a clot evacuation device.

FIGS. 8A-B illustrate images with or without rotational image stabilization.

FIG. 10 is a comparison of pictures taken with and without a non-powered plate and mask.

FIGS. 12A-D illustrate various embodiments of a clot evacuation device. FIGS. 12A and 12B are close up views of an embodiment of the distal tip of a clot evacuation device comprising a conically-shaped transparent distal bulb. FIG. 12C schematically illustrates the rotational ability of an inner hypotube. FIG. 12D illustrates a cross section of an elongated body of a clot evacuation device.

FIG. 17 illustrates various embodiments of a clot evacuation device.

FIGS. 24A-G show an optical introducer and/or clot evacuation device. FIG. 24A shows a close up view of the distal end of an optical introducer inserted through an outer sheath. FIG. 24B shows a close up view of the distal end of a clot evacuation device inserted through an outer sheath. FIG. 24C shows a cross-sectional schematic of the operational components within the elongate body of the clot evacuation device of FIG. 24B. FIG. 24D shows a handpiece of a clot evacuation device with a portion of the housing removed. FIG. 24E shows a perspective view of a user's hand holding a clot evacuation device. FIG. 24F shows a perspective view of a clot evacuation device with a peel-away sheath. FIG. 24G schematically illustrates the coupling of navigation system components to a clot evacuation device.

FIGS. 25A-C show a close up view of the distal end of a clot evacuation device with a windshield and an insertable introducer. FIG. 25A shows the clot evacuation device with an optical introducer inserted. FIG. 25B shows the clot evacuation device with an introducer inserted. FIG. 25C shows the clot evacuation device without an inserted introducer.

FIG. 26A shows the clot evacuation device with an introducer inserted. FIG. 26B shows the clot evacuation device without an inserted introducer. FIG. 26C shows a cross sectional view from the distal end. FIG. 26D shows a perspective view of the clot evacuation device with the windshield removed. FIG. 26E shows a close up of an irrigation hypotube configured to clean the lens of the clot evacuation device's visualization device. FIGS. 26F-I show various examples of the windshield and atraumatic tip.

FIG. 27A shows a close up view of the distal end of the clot evacuation device with an optical introducer inserted. FIG. 27B shows a close up view of the distal end of the clot evacuation device with an introducer inserted. FIG. 27C shows a close up view of a distal end of the clot evacuation device without an inserted introducer. FIGS. 27D and 27E show another example of a clot evacuation device and insertable introducer with a balloon shielding member. FIG. 27D is a close up view of the distal end of the clot evacuation device. FIG. 27E is a side cross-sectional view of the clot evacuation device.

FIG. 30 shows an example of a clot evacuation device.

DETAILED DESCRIPTION OF THE PREFERRED EMBODIMENTS

Figure 2A:
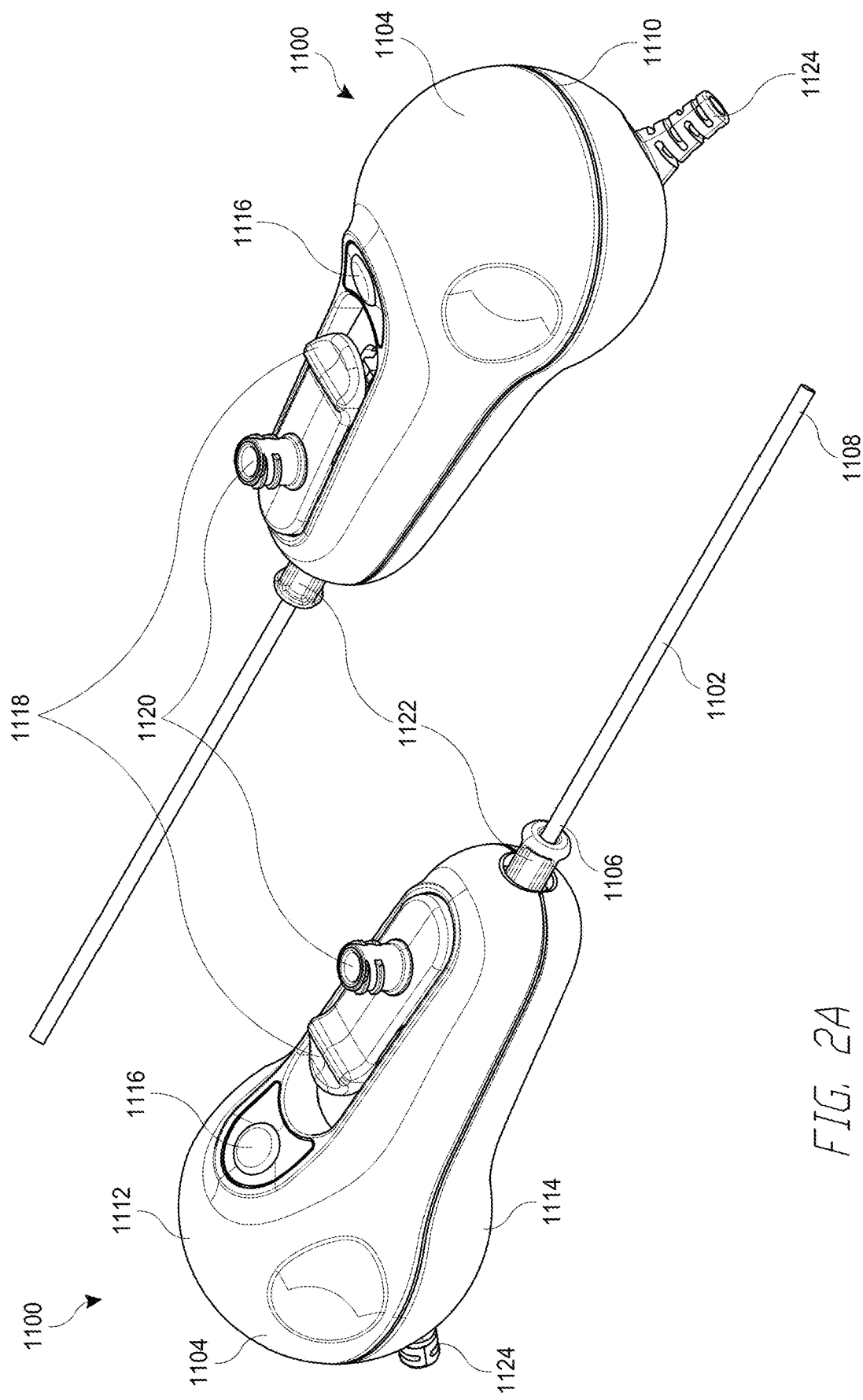
FIGS. 2A-C illustrate various embodiments of a clot evacuation device.

Embodiments of the present disclosure relate to devices, methods, and systems providing a clot evacuation device and visualization (for example an integrated clot evacuation device having visualization) for use in neurosurgical applications, particularly for the evacuation of clots formed as a result of intracranial hemorrhage (ICH). The clot evacuation devices disclosed herein may be used as general evacuation devices for other applications as well, particularly neurovascular applications, in addition to or instead of clot evacuation. For example, the evacuation devices can be used to aspirate/evacuate blood, tissue, fluid, particulate, debris, and/or other material from the body. Before these embodiments are described in greater detail, it is to be understood that this application is not limited to particular embodiments described, as such may, of course, vary. It is also to be understood that the terminology used herein is for the purpose of describing particular embodiments only, and is not intended to be limiting, since the scope of the present disclosure will be limited only by the claims as presented herein or as added or amended in the future. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the terms "about," "around," and "approximately." These terms are used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Also provided are kits for use in practicing the subject methods, where the kits may include one or more of the devices described herein the specification, and/or components of the subject systems. In embodiments, the components within the package are pre-sterilized. Further details regarding pre-sterilization of packaging may be found in U.S. Pat. No. 8,584,853, filed Feb. 16, 2012, and hereby incorporated by reference into this specification in its entirety.

FIG. 1 illustrates an embodiment of a system 2 for the visualization and evacuation of a clot, such as described above in relation to ICH. In some embodiments, a clot evacuation system 2 comprises: an integrated clot evacuation device 4 (described in much greater detail below), a controller 6, and a cable 8 that provides electrical communication between the controller 6 and the integrated clot evacuation device 4. By integrated, one of skill in the art will understand that the clot evacuation device may provide visualization and evacuation integrated into a single device.

In certain embodiments, the controller 6 may comprise a housing having a memory port such as an SD card slot 10 (and/or optionally a USB) and a camera button 12. The camera button 12 may activate the system to collect and/or store a still or moving image. The controller 6 may further comprise a power button 14, a mode switch button 16, and brightness controls 18. The controller 6 can further comprise a display such as a screen 19 for displaying still images and/or video.

Activating the mode switch button 16 may switch the system between different modes such as a procedure mode in which video and/or still images are collected and displayed in real-time on the video screen 19 and a consultation mode, in which a clinician may selectively display stored images and video on the video screen 19 for analysis. For example, while in procedure mode, the system could display video or images from the visualization sensor in real-time. By real-time, it is meant that the screen 19 can show video of the interior of a tissue site as it is being explored by the clinician. The video and/or images can further be stored automatically by the system for replay at a later time. For another example, while in consultation mode, the screen 19 may conveniently display specific images or videos that have previously been acquired by the system, so that the clinician can easily analyze the collected images/data, and discuss the images and data with a patient. In some embodiments, the clinician may be able to annotate the images via a touch screen or other suitable means.

In certain embodiments, the screen 19 may be any type of image plane suitable for visualizing an image, such as the screen on an iPad, a camera, a computer monitor, cellular telephone or a display carried by a head worn support such as eyeglasses or other heads up display. In certain embodiments, the cable may be avoided by configuring the device and display to communicate wirelessly.

In some embodiments, it may be desirable to remove the cord and provide instead a wireless communication link between the probe and the monitor and possibly also to a centralized medical records storage and/or evaluation location. Local transmission such as to the monitor within a medical suite may be accomplished via a local area network such as, for example, a "WiFi" network based on IEEE 802.11 wireless local area networking standards, Bluetooth wireless personal area networking standard, or the low power consumption ANT wireless protocol. Transceiver chips and associated circuitry are well understood in the art, and may be located within the hand piece housing of the integrated clot evacuation device 4, which is discussed below.

In certain embodiments, the clot evacuation device 4 of FIG. 1 may be used in conjunction with a neuro-navigational system and/or other medical navigation system. To support the placement of the clot evacuation device, an access device may be used. The access device has attributes that enable precise positioning and immobilization of the clot evacuation device at a specific angle or range of angles with respect to the skull. The access device can be a part of a stereotaxis frame, or it can be frameless and therefore directly secured to the skull. Examples of such frameless devices include but are not limited to the "Navigus System for Frameless Access" and the NAVIGATION™ products made by Image-Guided Neurologics, Inc. located in Melbourne, Fla., or the Stealth Station™ Intraoperative Guiding system (Medtronic Sofamor Danek, Memphis, Tenn.). Using a stereotaxis frame or a frameless access device, the clot evacuation device may be placed on the scalp surface, on the skull surface, inside the skull, or positioned above the skull. For frameless stereotaxy, users can choose between anatomic landmarks (ALs) or surface fiducial markers (FMs) for their match points to define an alignment of the head in the physical and radiographic image space. To further facilitate positioning of the clot evacuation device inside the head, fiducial markers may be placed on the clot evacuation device or handle assembly that includes the clot evacuation device. In some embodiments, navigation may be performed using detection devices such as motion sensors, accelerometers, and/or gyros.

In certain embodiments, during clot evacuation of a target site in the brain, patient recovery status may be monitored using one or more sensing methods, such as but not limited to monitoring of oxygen levels or saturation, rate of carbon dioxide production, heart rate, intracranial pressure and/or blood pressure. Also, the sensing element's measure could be used to modulate the intensity, frequency and/or duty cycle of components of the clot evacuation device. Such a feedback process is also known as a closed loop control system. Some embodiments may also include the use of a disposable patient interface (DPI), a sterile, compliant conductive gel/oil pack which interfaces between the ultrasound transducer and the patient.

FIG. 2A illustrates front and back perspective views of an embodiment of an integrated clot evacuation device 1100 that may be utilized in the clot evacuation system described above, comprising an elongated body 1102 and a handpiece 1104. The elongated body 1102 may have a length that is at least around 1.5 times longer than its width or diameter, at least around 2 times longer than its width or diameter, at least around 4 times longer than its width or diameter, at least around 10 times or longer than its width or diameter, at least around 20 times longer than its width or diameter, at least around 30 times longer than its width or diameter, at least around 50 times longer than its width or diameter, or longer than 50 times the width or diameter. The length of the elongated body 1102 may vary, and in some instances may be at least around 2 cm long, at least around 4 cm long, at least around 6 cm long, at around least 8 cm long, at least around 10 cm long, at least around 15 cm long, at least around 20 cm long, at least around 25 cm, at least around 50 cm, or longer than 50 cm. The elongated body 1102 may have the same outer cross-sectional dimensions (e.g., diameter) along the entire length. Alternatively, the cross-sectional diameter may vary along the length of the elongated body 1102. In certain embodiments, elongated body 1102 is a tubular elongated body and the outer diameter of the tubular elongated body is approximately 0.1 to 10 mm, approximately 0.5 mm to 6 mm, approximately 1 mm to 4 mm, approximately 1.5 mm to 3 mm, approximately 2 mm to 2.5 m, or approximately 2.1 mm. In certain embodiments, the elongated body 1102 has the diameter of a 14 gauge needle, having an outer diameter (OD) of about 2.1 mm and an inner diameter (ID) of about 1.6 mm.

In certain embodiments, and as described elsewhere in the specification, the elongated body 1102 may have a proximal end 1106 and a distal end 1108. The term "proximal end", as used herein, refers to the end of the elongated body 1102 that is nearer the user (such as a physician operating the device in a clot evacuation procedure), and the term "distal end", as used herein, refers to the end of the elongated body that is nearer the internal target tissue of the subject during use. The elongated body 1102 is, in some instances, a structure of sufficient rigidity to allow the distal end to be pushed through tissue when sufficient force is applied to the proximal end of the elongated body 1102. As such, in certain embodiments the elongated body 1102 is not pliant or flexible, at least not to any significant extent. In other embodiments, the elongated body 1102 is pliant and flexible, allowing the elongated body 1102 to twist and bend around tissues.

In certain embodiments, the distal end 1108 will be open-ended to provide visualization, illumination, irrigation, and/or aspiration through the open end. The distal end 1108 may be blunted to prevent tissue damage. The elongated body 1102 may be used to traverse through tissues of the brain to reach a target of interest, such as a clot. The device may provide visualization of tissues through the open end of the elongated body and display these images on a separate screen such as depicted above in FIG. 1.

In certain embodiments, as is known in the art, any portion of the clot evacuation device, such as the outer portion of the elongated body and/or the inner hypotube may be made of metal, polymer, or a combination of both, in a variety of configurations including but not limited to tubular, oval, rectangular, or combinations of all. A pre-shaped feature of the distal end of the elongated body can be achieved using a shape memory alloy such as nickel titanium (NiTI) or shape memory polymers (SMPs), also called "smart" materials that can switch between two shapes, from a fixed (temporary) shape to a predetermined permanent shape. Also, any combination of metal, shape memory metal, shape memory polymers or conventional polymers may be utilized to achieve the desirable deflection characteristics. Shape memory polymers may include, but are not limited to, polyurethanes or polystyrenes. Such memory materials are beneficial when there is a need for a device that needs to deflect to access desirable treatment areas that are located in spaces beyond the external shaft. In certain embodiments, the elongated body is made from a material that is flexible but resists torsion, thereby allowing the elongated body to flex while in use.

As depicted in FIG. 2A, in embodiments, the handpiece 1104 may have a rounded "clamshell" shape comprising a seam 1110 connecting a clamshell top 1112 and a clamshell bottom 1114. In some embodiments, the clamshell top 1112 and bottom 1114 and can be manufactured in two pieces and then attached together at the seam 1110. The rounded clamshell shape provides a comfortable and ergonomic handle for a user to hold while using the device. In certain embodiments and as will be described in greater detail later, the handpiece may comprise an image capture control such as a button 1116 configured to capture a desired image. In further embodiments, the image capture control may comprise a switch, dial, or other suitable mechanism. The handpiece 1104 may further comprise a retraction control 1118 that retracts or extends a portion of the elongated body 1102. The retraction control 1118 will be described in greater detail in relation to FIGS. 2B-C and later Figures. In certain embodiments, the handpiece 1104 may have a bayoneted design.

In certain embodiments, the control 1116 may selectively activate the acquisition of an image and/or video. The control 1116 may thus be configured to selectively start video recording, stop video recording, and/or capture a still image either during video recording or while video recording is off. In embodiments, these activities may be activated via voice and/or buttons on a tablet. In certain embodiments, a secondary tablet/phone/screen could be kept in a sterile draped bag.

In embodiments, the handpiece 1104 may comprise a luer connection 1120, configured to connect to any fluid source as described herein this section or elsewhere in this specification, such as sterile saline. The luer connection 1120 may be in fluid communication with a lumen extending throughout the length of the elongated body 1102, allowing for the delivery of fluid or agents to the tissue site.

The junction between the handpiece 1104 and the elongated body 1102 may include a hub 1122 that connects the handpiece 1104 to the elongated body 1102. In some embodiments, the hub 1122 may be detachable, allowing the elongated body to be detached from the handpiece 1104. In other embodiments, the elongated body is permanently attached to the handpiece 1104 via the hub 1122 to provide an integrated assembly. The handpiece 1104 may further comprise a strain relief node 1124, configured to attach to an electrical cable (not shown in FIG. 2A). The strain relief node 1124 can serve to reduce strain on electrical wiring that may be in electrical communication with the handpiece 1104.

In some embodiments, the clot evacuation device 1100 is configured as an integrated assembly for one time use. The clot evacuation device 1100 may be pre-sterilized, thus the combination of integration and pre-sterilization allows the clot evacuation device 1100 to be ready for use upon removal from the packaging. Following use, it may be disposed. Thus, the handpiece 1104, elongated body 1102, and other components, such as the cable, may be all one single unit. By one single unit, it is meant that the various portions described above may be attached together as one single piece not intended for disassembly by the user. In some embodiments, the various portions of the single unit are inseparable without destruction of one or more components. In some embodiments, the display, as described herein this section or elsewhere in the specification, may also be incorporated and sterilized as part of a single unit clot evacuation device.

With respect to imaging a clot, methods include positioning a distal end of the elongated body 1102 in viewing relationship to the target tissue (for example a clot and/or brain tissue), and utilizing viewing and/or imaging components integrated into the clot evacuation device to view the target tissue. By viewing relationship is meant that the distal end is positioned within 40 mm, such as within 10 mm, including within 5 mm of the target of interest. Positioning the distal end of the clot evacuation device in relation to the desired target tissue may be accomplished using any convenient approach, including direct linear advance from a percutaneous access point to the target tissue. Following positioning of the distal end of the clot evacuation device in viewing relationship to the target tissue, the target is imaged through use of illumination elements and visualization sensors (such as described elsewhere in the specification) to obtain image data. Image data obtained according to the methods of the invention is output to a user in the form of an image, e.g., using a monitor or other convenient medium as a display means. In certain embodiments, the image is a still image, while in other embodiments the image may be a video.

In system embodiments involving a burr hole or other aperture in the skull to gain access to the clot site, an endoscope-assisted micro-neurosurgery device frequently known as a trocar may be used in any known manner in combination with the embodiments of the device and system disclosed herein this section or elsewhere in the specification. The clot evacuation devices disclosed herein this section or elsewhere in the specification may be used within any channel of a trocar, such as those described below. A trocar is used to help manage and control several devices that are often used in neurosurgical procedures involving burr holes. Examples of such commercial devices include, but are not limited to: MINOP Trocars from Aesculap, B. Braun (Melsungen, Germany) and Channel Trocars from Medtronic Inc., (Minneapolis, Minn.). Most conventional trocars have either three or four channels. For example, a three-channeled trocar, has an elongated tube having a distal end and a proximal handle, two small channels (irrigation channel and overflow channel) and one larger channel to allow a visualization device and/or therapeutic device to be introduced there through. Four-channeled trocars, may have an elongated tube having a distal end and proximal handle, with two small channels (irrigation channel and overflow channel) and two larger channels (for a visualization device such as a scope or an ultrasound diagnostic device, and another channel for a therapy device). In other examples, four-channeled trocars allow neurosurgery procedures such as ventriculostomy, biopsies, and removal of cysts, blood clots and other obstructions to be performed under direct visualization simultaneously with an endoscope or diagnostic device placed in the visualization channel. Three-channeled trocars require a visualization device to be placed into the working channel first to assess the therapy field, and then removed so that the therapeutic device can be introduced through the same channel to perform the therapeutic procedure. Trocars are usually made of metal but also can be made of polymer, and may have a variable length anywhere between 100-400 mm.

Figure 2B:
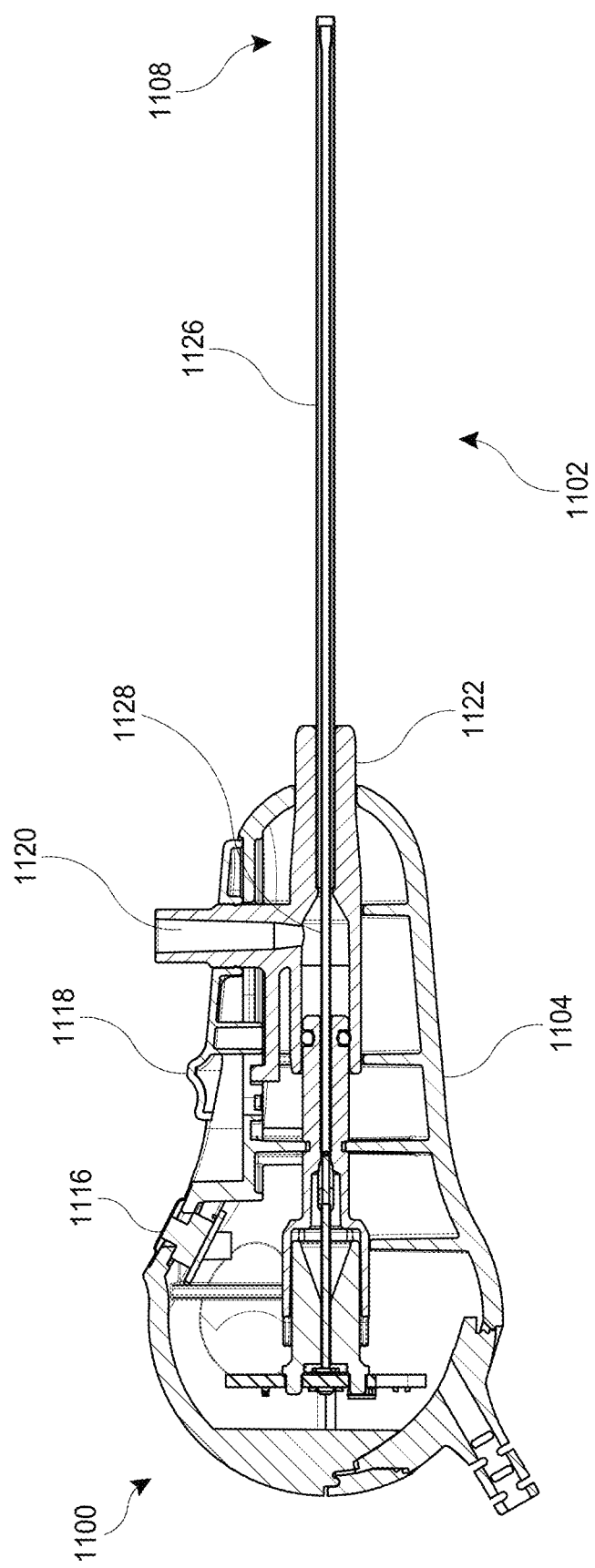

FIG. 2B illustrates a cross-sectional side view of an embodiment of the clot evacuation device 1100 depicted in FIG. 2A. As in FIG. 2A, the clot evacuation device 1100 comprises a number of components such as an image capture trigger 1116, retraction control 1118, luer 1120, elongated body 1102, handpiece 1104, and hub 1122.

Figure 2C:
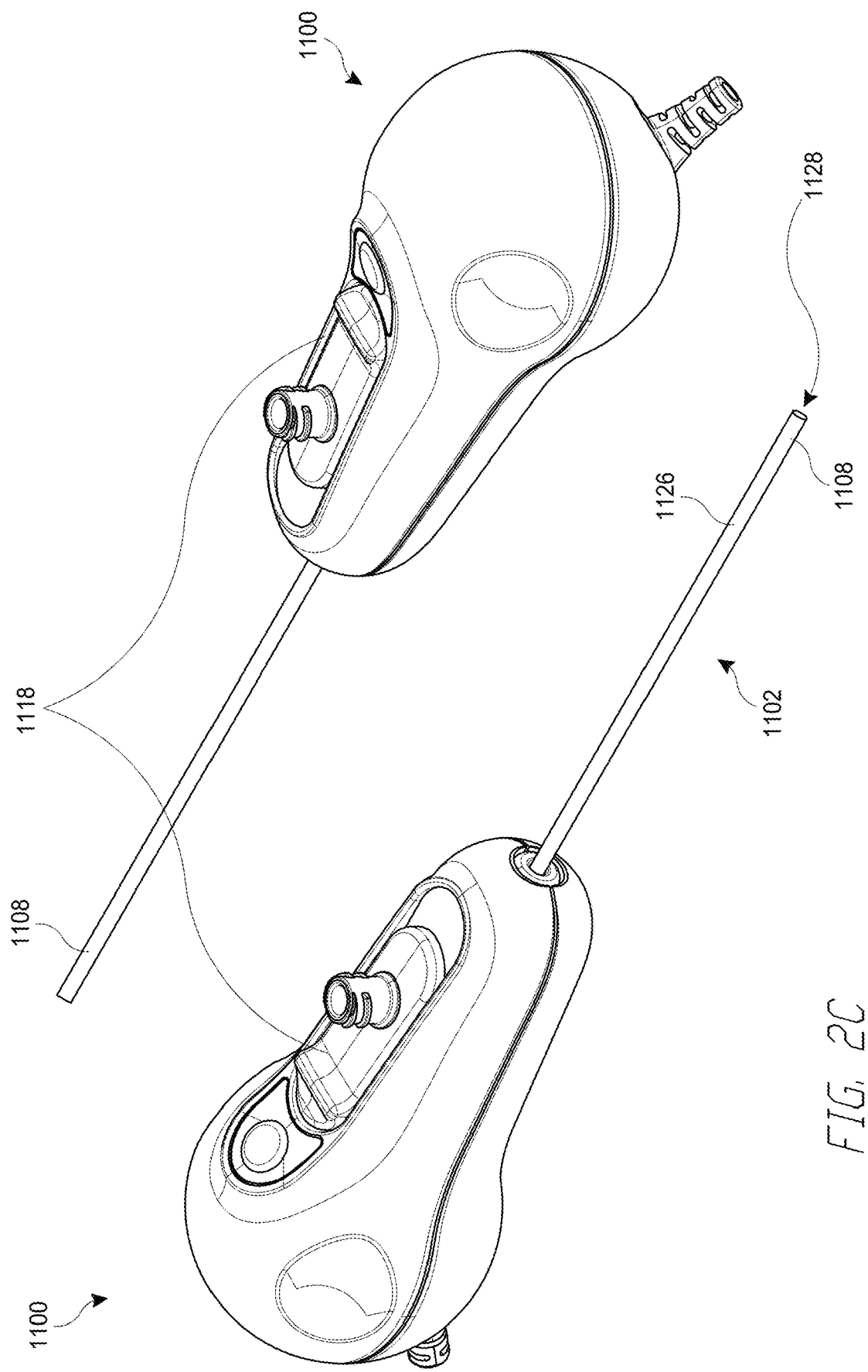

Referring now to FIG. 2C, in some embodiments the handpiece 1104 may comprise a retraction control 1118. The retraction control 1118 can serve to retract the outer tubular body 1126 of FIG. 3A, relative to the hypotube 1128 (described in greater detail below), thus allowing the hypotube 1128 to extend beyond the front opening of the outer tubular body 1126 at the distal end 1108.

Figure 3A:
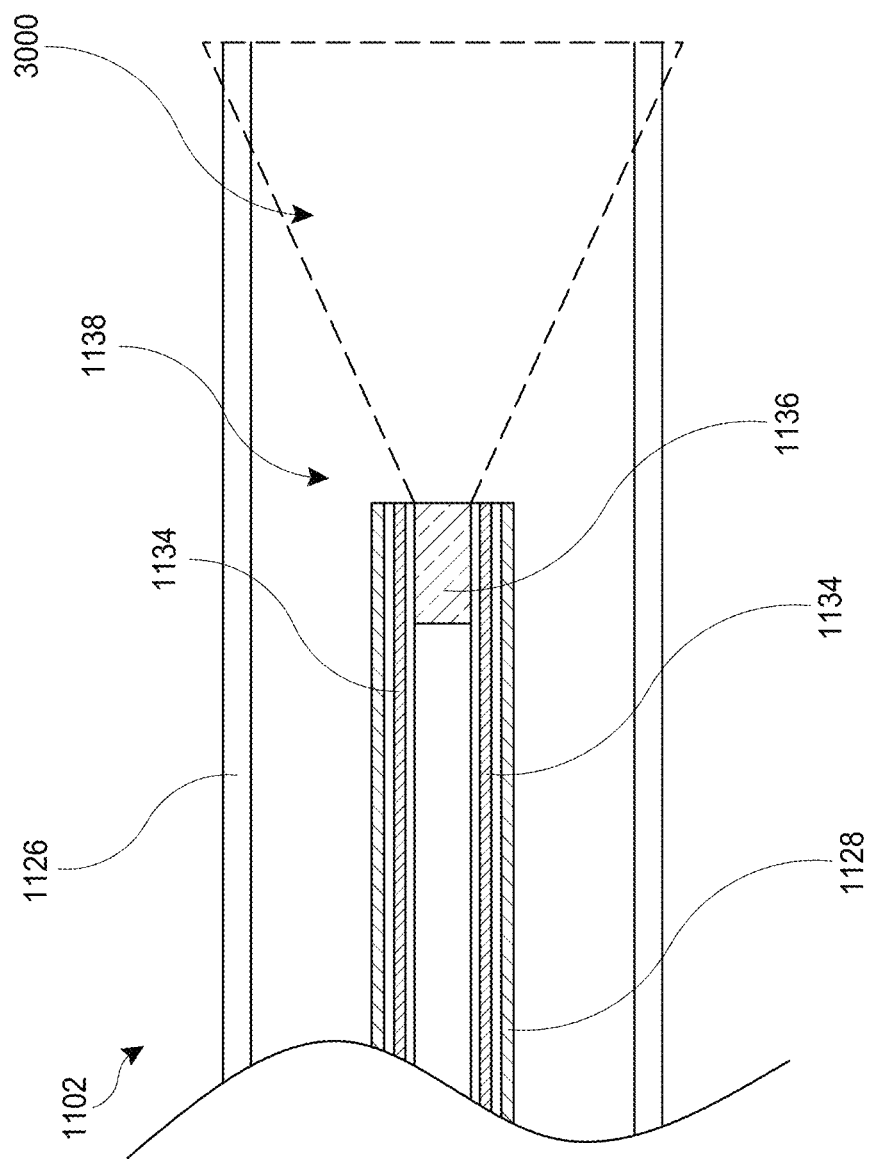

FIG. 3A shows a side cross section of an embodiment of the distal end 1108 of the elongated body of FIGS. 2A-2C with additional detail not shown in FIGS. 2A-2C. The elongated body 1102 comprises an outer tubular body 1126 which may be in the form of an elongated tube. The dimensions of the outer tubular body 1126 can vary, but preferably are approximately 3.7 mm in diameter. Visualization is provided by an inner hypotube 1128 extending concentrically through the outer tubular body. This inner hypotube 1128 can act to transmit an image of a tissue site to a camera located in the handpiece 1104, or alternatively there may be a camera located at the distal tip of the inner hypotube 1128. The inner hypotube 1128 may also contain illumination elements 1134, such as illumination fibers, to illuminate a target tissue. In some embodiments, the outer tubular body 1126 may be slid forward beyond the inner hypotube 1128 or retracted to extend the inner hypotube 1128 beyond the outer tubular body 1126. When the outer tubular body 1126 is slid into the forward position, as depicted in FIG. 3A, the visualization elements (for example, the camera, lens, and related components) in the inner hypotube 1128 may provide a field of view 3000, schematically depicted in FIG. 3A, down the "tunnel" of the interior of the hypotube 1128. Such a position can separate the soft tissue from the distal optics 1136 (such as a lens) and also allow enough distance so the tissue at the distal tip is in focus (see FIG. 3A).

In certain embodiments, the elongated body 1102 may comprise a deflection which may be lateral or sideways. The distal end of the hypotube 1128 may extend laterally away from the outer tubular body 1126. The degree of deflection or distance can be moved and adjusted as desired by moving the inner hypotube 1128 further in any direction. In certain embodiments, the handpiece 1104 can be rotated by 360 degrees, so that rotating the distal end 1108 of the elongate body 1102 will cause the distal portion to access an area within much larger space. The distal end 1108 can be moved up and down within the patient's head, thereby deflecting the distal end 1108 to a wide range of space well beyond its original position.

In some embodiments, the distal end of the visualization element may comprise a distal lens 1136 configured to facilitate the imaging of an internal tissue site. The distal lens 1136, or any other lens, may develop defects and imperfections during manufacturing, leading to a distortion in the image. These distortions may be unique to individual lenses and, thus, in the case of the embodiments disclosed herein this application, may be unique to an individual clot evacuation device 1100. Thus, to enhance image quality, the device 1100 as depicted in FIG. 2A, may include an automatic optical correction in the form of a unique algorithm. In some embodiments, the algorithm may be stored in a chip or other suitable means within the handpiece 1104.

In certain embodiments, the automatic optical correction may serve to improve the image quality generated by the clot evacuation device 1100. The Abbe number, also known as the V-number or constringence of a transparent material, is a measure of the material's dispersion (variation of refractive index with wavelength) in relation to the refractive index, with high values of V indicating low dispersion (low chromatic aberration). Low chromatic aberration is desired to optimize image quality, but achieving low chromatic aberration normally increases manufacturing cost. In some embodiments, chromatic aberrations in the clot evacuation device may be corrected via the aforementioned software algorithm at the time of clinical use, which allows economies during manufacturing. For example, the optical correction may allow for visualization performance from the device with less expensive lenses that rivals the performance of visualization devices that use far more expensive lenses with minimal imperfections.

In certain embodiments, the optical correction may be generated by comparing a captured image to a known definition pattern and generating an algorithm that corrects chromatic aberrations and image distortion specific to each individual tissue visualization device. In some embodiments, the optical correction may be unique to an individual tissue visualization device. In particular embodiments, additional information regarding the tissue visualization device may be stored, such as the X,Y position of the center of the lens, the image circle size, and unique characteristic of the LED so as to provide a consistent initial light level. The aforementioned characteristics of the clot evacuation device and additional characteristics described elsewhere in the specification may be determined during manufacturing and stored in computer memory such as electrically erasable programmable read-only memory (EEPROM). In embodiments, the entirety of the handpiece 1104 and the elongated body 1102 may be an integrated unit. In certain embodiments, the handpiece 1104 further comprises a retraction control 1118, configured to retract the elongated body 1102 so as to expose the distal lens 1136 of the optical hypotube 1128. In some embodiments, the handpiece 1104 may further comprise a luer 1120, configured to conduct fluid to the internal tissue site via the lumen.

In embodiments, to generate the algorithm at the point of manufacture, the distal optic 1136 is focused on a known definition pattern. A computer can then compare the captured image to the known pattern and create an algorithm that restores the captured image to the true definition pattern. As described above, that algorithm may then be stored in a chip in the handpiece 1104.

When the handpiece 1104 is connected to a displayer 6 at the clinical site, as described previously in relation to FIG. 1, the algorithm serves as the basis for the displayer 6 to correct the captured image such that aberrations in the optical system are removed. Each individual clot evacuation device 1100 will have unique aberrations, so each handpiece 1104 will carry a unique algorithm designed to correct that system.

In certain embodiments, the elongated body 1102 may be dimensioned to be slidably moved through the internal passageway of an access device or move directly through tissue without the use of an additional access device. In embodiments, the elongated body 1102 may have a length that is 1.5 times or longer than its width, such as 2 times or longer than its width, including 5 or even 10 times or longer than its width, e.g., 20 times longer than its width, 30 times longer than its width, or longer. At least the distal end of the device may have a longest cross-sectional dimension that is 10 mm or less, such as 8 mm or less and including 7 mm or less, where in certain embodiments the longest cross-sectional dimension has a length ranging from 5 to 10 mm, such as 6 to 9 mm, and including 6 to 8 mm.

In some embodiments, the hypotube 1128 may be biased against the inner diameter of the outer tubular body 1126. For example, the outer tubular body 1126 may comprise dimples on either the outer tubular body 1126 or the hypotube 1128 that would bias the OD of the hypotube 1128 against the ID of the elongated body 1102.

In particular embodiments, the outer tubular body 1126 is not retractable/extendible; instead, the outer tubular body 1126 and the inner hypotube 1128 have a fixed length. For example, the inner hypotube 1128 may be the same length as the outer tubular body 1126 or may be shorter, so that the inner hypotube 1128 is offset inside the outer tubular body 1126. Alternatively, the inner hypotube 1128 may be biased against a side of the outer tubular body 1126.

In embodiments, the distal end 1108 of the elongated body 1102 may comprise a deflected tip to allow for a mechanical means of altering the direction of view of the hypotube 1128 (such as about 5-6 degrees). In some embodiments, the direction of view may be at least about 3 degrees, at least about 6 degrees, at least about 12 degrees, at least about 15 degrees, at least about 20 degrees, at least about 30 degrees, at least about 45 degrees, or greater than 45 degrees off the central longitudinal axis of the hypotube 1128. Wide angle field of view can be accomplished with a lens, or by rotating the fiber optic if the distal end is deflected off axis.

In some embodiments, surrounding the inner hypotube 1128 is a lumen 1138, as shown in FIG. 3A, which may be used to provide aspiration to remove a clot and/or provide irrigation to clean a distal lens and/or break up a clot. In some embodiments, irrigation may also or alternatively be provided along the lumen 1138, or through an outer sleeve around the outer tubular body. Alternatively, irrigation may be provided along a separate channel within the outer tubular body 1102. In certain embodiments, the device may use any of the irrigation modes described herein this section or elsewhere in the specification to clean the distal lens 1136.

In certain embodiments, the clot evacuation device may further include an irrigator and aspirator configured to flush an internal target tissue site and/or a component of the device, such as a lens of the visualization sensor. As such, the elongated body 1102 may further include one or more lumens that run at least the substantial length of the device, e.g., for performing a variety of different functions, as summarized herein this section or elsewhere in the specification. In certain embodiments where it is desired to flush (i.e., wash) the target tissue site at the distal end of the elongated body 1102 (e.g. to remove ablated tissue from the location, etc.), the elongated body 1102 may include both irrigation lumens and aspiration lumens. Thus, the clot evacuation device can comprise an irrigation lumen extending axially through the elongated body. During use, the irrigation lumen(s) may be operatively connected to a fluid source (e.g., a physiologically acceptable fluid, such as saline) at the proximal end of the device, where the fluid source is configured to introduce fluid into the lumen under positive pressure, e.g., at a pressure ranging from 0 psi to 60 psi, so that fluid is conveyed along the irrigation lumen and out the distal end. While the dimensions of the irrigation lumen may vary, in certain embodiments the longest cross-sectional dimension of the irrigation lumen ranges from 0.5 mm to 5 mm, such as 0.5 mm to 3 mm, including 0.5 mm to 1.5 mm.

During use, the aspiration lumen (e.g., lumen 1138) may be operatively connected to a source of negative pressure (e.g., a vacuum source) at the proximal end of the device. For example, means to generate suction may include: a vacuum pump, hospital wall supply, hand operated syringe, and/or foot operated contraption. While the dimensions of the aspiration lumen may vary, in certain embodiments the longest cross-sectional dimension of the aspiration lumen ranges from 1 mm to 7 mm, such as 1 mm to 6 mm, including 1 mm to 5 mm. In some embodiments, the aspirator comprises a port having a cross-sectional area that is 33% or more, such as 50% or more, including 66% or more, of the cross-sectional area of the distal end of the elongated body. Rather than use wall suction, the device may alternatively use a big syringe that an assistant operates. In some embodiments, a battery powered vacuum pump may be used and/or a foot operated pump integrated into a waste chamber.

In some instances, the negative pressure source is configured to draw fluid and/or tissue from the target tissue site at the distal end into the aspiration lumen under negative pressure, e.g., at a negative pressure ranging from 300 to 600 mmHg, such as 550 mmHg, so that fluid and/or tissue is removed from the tissue site and conveyed along the aspiration lumen and out the proximal end, e.g., into a waste reservoir. In certain embodiments, the irrigation lumen and aspiration lumen may be separate lumens, while in other embodiments, the irrigation lumen and the aspiration functions can be accomplished in a single lumen.

In certain embodiments, the suction should be increased beyond the wall suction described above. For example, wall suction may be used for pulling the clot material through the channels and tubing of the device but use higher hand or pump driven suction for getting the clot into the device or for a boost for a clogged channel/tubing. In certain embodiments, various controls may be used for irrigation and suction. For example, a control may be located on the handpiece 1104, the cord, the tablet (physical button, soft button, voice activated) and/or on a foot peddle. In certain embodiments, a blood pressure cuff may be used to generate suction.

Figure 3B:
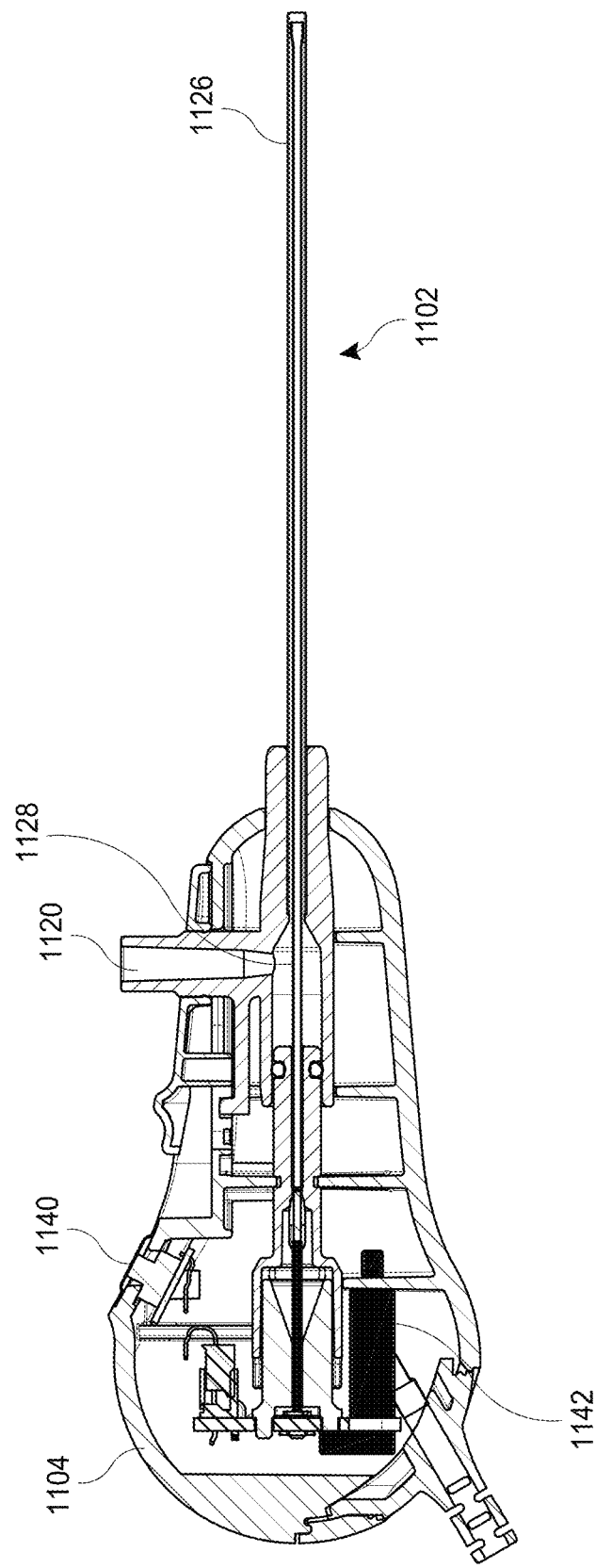

However, a common issue that may occur during aspiration of clots is that the clot becomes lodged in the lumen 1138, thereby preventing/limiting further irrigation and aspiration. To address these potential issues, in some embodiments, as depicted and described in FIG. 3B, the inner hypotube 1128 comprising the visualization elements (such as the visualization sensor and lens) may be vibrated to break up and remove clots that may be lodged in the lumen 1138. The handpiece 1104, as depicted in FIG. 3B, above in FIG. 1, and/or in further detail below, may further comprise a vibration/oscillation actuator 1140 and/or vibration/oscillation plate or motor 1142 capable of vibrating the inner hypotube 1128. In embodiments, the inner hypotube 1128 may be constructed to be vibration resistant, to prevent damage during vibration. As will be understood by one of skill in the art, any port (such as a suction port 1122) described herein this section or elsewhere in the specification may be used for aspiration, irrigation, or both. As illustrated in FIG. 3B, the outer tubular body 1126 can be extended beyond the distal end of the inner hypotube 1128 with visualization device and can be retracted to effectively extend the visualization device beyond the outer tubular body 1126.

Figures 3C, 3D:
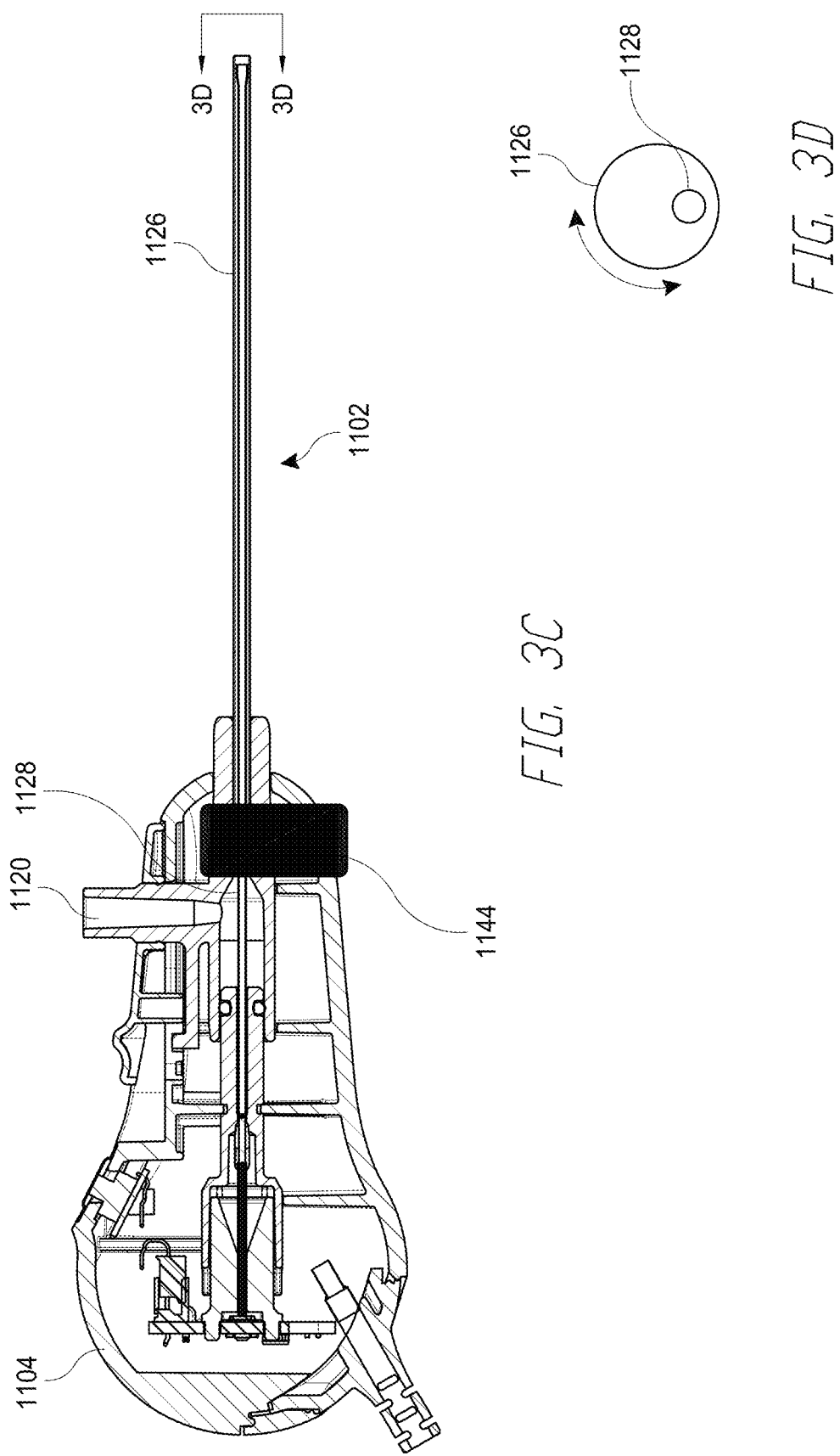

In some embodiments, as depicted and described in FIG. 3C, the outer tubular body 1126 and/or the inner hypotube 1128 may be rotatable relative to one another to further aid in dislodging clots. The handpiece 1104 can include integrated means to rotate the outer tubular body 1126. These means may comprise an internal motor and/or an external thumb wheel 1144 that can be manually turned by the user. FIG. 3D schematically depicts in a cross-section taken along the elongate body 1102, viewed along the direction indicated by arrows 3D-3D in FIG. 3C, the rotation of the outer tubular body 1126 relative to the inner hypotube 1128. The inner hypotube 1128 may remain in random locations within the outer tubular body 1126 as the outer tubular body 1126 is rotated, thereby acting as a scraper to aid in removing clots that have become lodged in the lumen. The outer tubular body 1126 may be inserted through an external protective sheath to protect body tissue during rotation. In some embodiments, the inner hypotube 1128 may be configured to be rotatable in addition to or alternatively to the outer tubular body 1126.

Figure 3E:
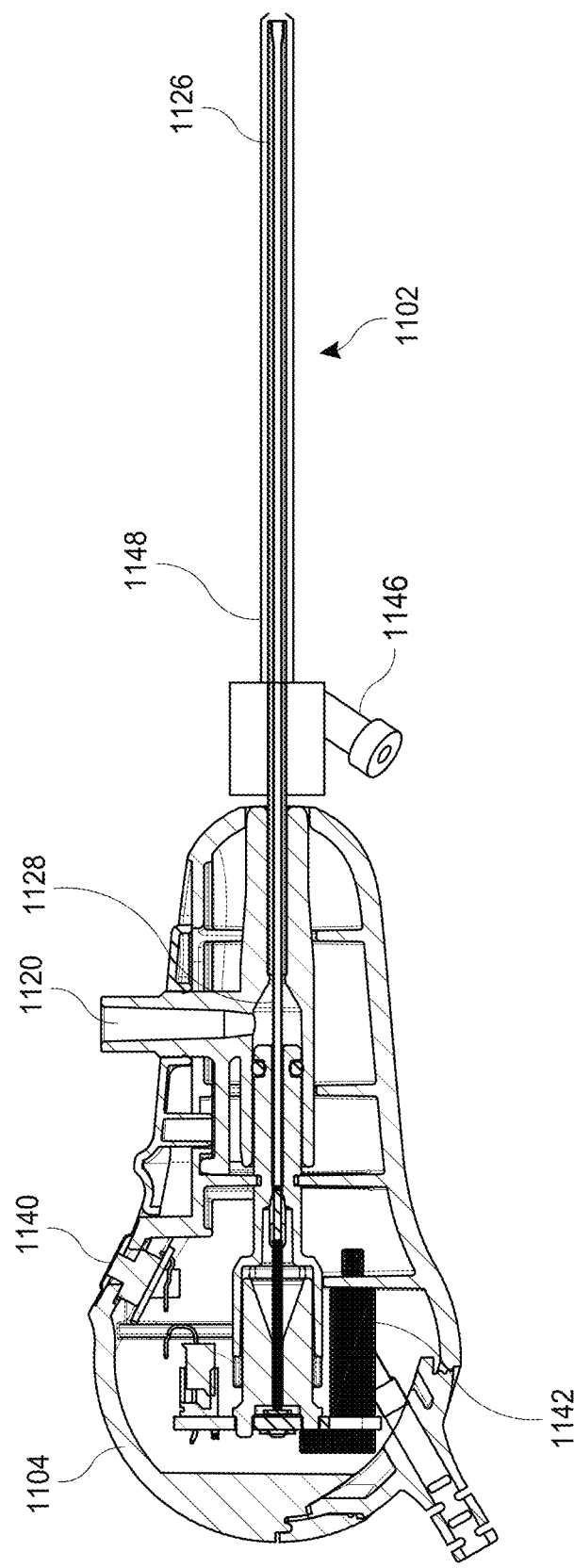

In certain embodiments, as depicted in FIG. 3E, the clot evacuation device 1100 may further comprise a second port 1146 for irrigation. The irrigation port 1146 may further be connected to an outer sleeve 1148 overlapping the outer tubular body 1126, as described above, to provide a path for irrigation between the outer diameter of the outer tubular body 1126 and the inner diameter of the sleeve 1148. The outer sleeve 1148 may comprise rigid or semi-rigid tubing. In embodiments, the outer tubular body 1126 may be perforated to aid in removing clot obstructions, without necessarily introducing a significant amount of fluid into the surgical site. The spacing of the perforations may be varied such that there are more perforations towards the distal end of the outer tubular body 1126 and less towards the proximal end. Further, the distal end of the clot evacuation device 1100 may be shaped, such as shown in FIG. 3E, to direct fluid onto the optical elements to clear the lens and/or to provide external irrigation to a clot. The outer sleeve 1148 may extend beyond the distal tip of the clot evacuation device 1100 and may comprise a tapered or beveled distal end to provide further blunting. Further, as described elsewhere in the specification, the distal end of the outer sleeve 1148 with irrigation elements may be retracted or extended. The distal end of the outer sleeve 1148 with irrigation elements when extended may act as an introducer into soft tissue with minimal disruption of brain tissue. Retraction of the distal end of the outer sleeve 1148 with irrigation elements can clear the end of the outer tubular body 1126 to open the suction lumen. The use of features which assist in breaking up clots that may be lodged within the aspiration lumen, can help the user avoid having to remove the device to clear the clots in mid-procedure, requiring the user to reintroduce the device and relocate the target tissue.

As described above, in certain embodiments, the elongated body 1102 may further include one or more infusion lumens 1138 that run at least the substantial length of the device, e.g., for performing a variety of different functions. In certain embodiments where it is desired to flush (i.e., wash) the location of the target tissue at the distal end 1108 of the elongated body 1102 and remove excess fluid, the elongated body 1102 may include both an irrigation and aspiration lumen. During use, the irrigation lumen may be operatively connected to a fluid source (e.g., physiologically acceptable fluid, such as saline) at the proximal end of the device, where the fluid source is configured to introduce fluid into the lumen under positive pressure, e.g., at a pressure ranging from 0 to 500 mm Hg, so that fluid is conveyed along the irrigation lumen and out the distal end.

While the dimensions of the irrigating lumen may vary, in certain embodiments the longest cross-sectional dimension of the irrigation lumen ranges from 1 to 3 mm. During use, the aspiration lumen is operatively connected to a source of negative pressure (e.g., vacuum source) at the proximal end of the device, where the negative pressure source is configured to draw fluid from the tissue location at the distal end into the irrigation lumen under positive pressure, e.g., at a pressure ranging from 50 to 600 mm Hg, so that fluid is removed from the tissue site and conveyed along the irrigation lumen and out the proximal end, e.g., into a waste reservoir. While the dimensions of the aspiration lumen may vary, in certain embodiments the longest cross-sectional dimension of the aspiration lumen ranges from about 1 to 10 mm, about 1 to 4 mm, about 1 to 3 mm, or less than 1 mm. Alternatively, a single lumen may be provided, through which irrigation and/or aspiration may be accomplished. In embodiments, the product packaging may include a single port stopcock as a means to control fluid flow. In particular embodiments, the stopcock or suitable valve may be directly integrated into the device. In further embodiments, more than one port or stopcock may be used, such as two ports and two stopcocks, three ports and three stopcocks, and so on. In some embodiments, a three-way stopcock may be provided so a clinician can 'toggle' between infusion and aspiration, or infusion of a first and second fluid, without connecting and reconnecting tubes.

Returning to FIG. 3A, the elongated body 1102 may comprise an outer tubular body 1126 which may be similar to a hypodermic needle such as a 14-gauge needle with the sharpened tip removed. However, in certain embodiments (not shown), the distal end of the elongated body 1102 may comprise a sharpened tip. The visualization element can be in the form of an inner hypotube 1128 extending concentrically through the outer tubular body 1126. The hypotube 1128 may act to transmit an image of a tissue site to a visualization sensor such as those described herein this section and elsewhere in the specification. In some embodiments, the distal tip of the hypotube 1128 may comprise a visualization sensor.

In certain embodiments, as depicted in FIG. 3F, visualization sensors 1150 or any other type of sensor described herein this section of elsewhere in the specification (such as a glucose sensor) may be positioned as shown in the figure. For example, two sensors 1150 may be positioned on the back of an elongate body of the hypotube 1128 or other visualization body, facing forward and backward (left panel), facing the side (i.e. perpendicular to the longitudinal axis of the elongate body) and forward (middle panel), and/or angled to face forward and to the side (right panel), with image integration in some examples. For example, the images from each sensor 1150 shown in the right panel can be stitched together to form a larger image with a wider field of view. As described elsewhere herein, the hypotube 1128 may be capable of rotational, vibrational/oscillating, and/or translational movement.

Visualization sensors of interest are those that include a photosensitive component, e.g., array of photosensitive elements that convert light into electrons, coupled to an integrated circuit. The integrated circuit may be configured to obtain and integrate the signals from the photosensitive array and output image data, which image data may in turn be conveyed to an extra-corporeal display configured to receive the data and display it to a user. The visualization sensors of these embodiments may be viewed as integrated circuit image sensors.

The integrated circuit component of these sensors may include a variety of different types of functionalities, including but not limited to: image signal processing, memory, and data transmission circuitry to transmit data from the visualization sensor to an extra-corporeal location, etc. The miniature visualization sensors may further include a lens component made up of one or more lenses positioned relative to the photosensitive component so as to focus images on the photosensitive component. Where desired, the one or more lenses may be present in a housing. Specific types of miniature visualization sensors of interest include complementary metal-oxide-semiconductor (CMOS) sensors and charge-coupled device (CCD) sensors. The sensors may have any convenient configuration, including circular, square, rectangular, etc. Visualization sensors of interest may have a longest cross-sectional dimension that varies depending on the particular embodiment, where in some instances the longest cross sectional dimension (e.g., diameter) is 10.0 mm or less, such as 6.0 mm or less, including 3.0 mm or less.

Visualization sensors of interest may be either frontside or backside illumination sensors, and have sufficiently small dimensions while maintaining sufficient functionality to be integrated at the proximal end of the elongated bodies within the handpiece of the devices of the invention. Aspects of these sensors are further described in one or more the following U.S. patents, the disclosures of which are herein incorporated by reference in their entireties: U.S. Pat. Nos. 7,388,242; 7,368,772; 7,355,228; 7,345,330; 7,344,910; 7,268,335; 7,209,601; 7,196,314; 7,193,198; 7,161,130; and 7,154,137.

The distal end of the elongated body may be configured for front viewing and/or side-viewing, as desired. In yet other embodiments, the elongated body may be configured to provide image data from both the front and the side, e.g., where the primary viewing axis from the distal end of the waveguide extends at an angle that is greater than about 2 or 5 degrees or 10 or 15 degrees or more relative to the longitudinal axis of the elongated body, described in greater detail below.

Depending on the particular device embodiment, as described above, the elongated body may or may not include one or more lumens that extend at least partially along its length. When present, the lumens may vary in diameter and may be employed for a variety of different purposes, such as irrigation, aspiration, electrical isolation (for example of conductive members, such as wires), as a mechanical guide, etc., as reviewed in greater detail below. When present, such lumens may have a longest cross section that varies, ranging in some in stances from 0.5 to 5.0 mm, such as 1.0 to 4.5 mm, including 1.0 to 4.0 mm. The lumens may have any convenient cross-sectional shape, including but not limited to circular, square, rectangular, triangular, semi-circular, trapezoidal, irregular, etc., as desired. These lumens may be provided for a variety of different functions, including as irrigation and/or aspiration lumens, as described in greater detail below.

In certain embodiments, as described above in relation to FIGS. 2-3E, clot evacuation devices may include one or more illumination elements configured to illuminate a target tissue location so that the location can be visualized with a visualization sensor, e.g., as described above. A variety of different types of light sources may be employed as illumination elements, so long as their dimensions are such that they can be positioned at or carry light to the distal end of the elongated body. The light sources may be integrated with a given component (e.g., elongated body) such that they are configured relative to the component such that the light source element cannot be removed from the remainder of the component without significantly compromising the structure of the component. As such, the integrated illumination element of these embodiments is not readily removable from the remainder of the component, such that the illumination element and remainder of the component form an inter-related whole. The light sources may be light emitting diodes configured to emit light of the desired wavelength range, or optical conveyance elements, e.g., optical fibers, configured to convey light of the desired wavelength range from a location other than the distal end of the elongated body, e.g., a location at the proximal end of the elongated body within the handpiece, to the distal end of the elongated body.

In certain embodiments, as known in the art, an imaging camera may be provided on the distal end of the clot evacuation device in combination with ultrasound. Such an electronic imaging camera may have a light emitting source provided by light emitting diodes (LAD) or by light delivered via fiber optics from an external source. The principles of operation are identical to endoscopes, but in this case the camera is incorporated in a single device together with the ultrasound device. Examples of such suitable cameras include but are not limited to devices from MediGus. Ltd, Omer, Israel; Omni Vision, Santa Clara, Calif.; Clear Image Technology, Elyria, Ohio. Further details may be found in U.S. Pat. Pub. No. 2012/0330196 A1, entitled "Methods and Apparatus for Removing Blood Clots and Tissue from the Patient's Head" filed Sep. 7, 2012, and which is hereby incorporated by reference in its entirety.

As with the visualization sensors, the light sources may include a conductive element, e.g., wire, or an optical fiber or bundle, which runs the length of the elongated body to provide for power and control of the light sources from a location outside the body, e.g., an extracorporeal control device.

Where desired, the light sources may include a diffusion element to provide for uniform illumination of the target tissue site. Any convenient diffusion element may be employed, including but not limited to a translucent cover or layer (fabricated from any convenient translucent material) through which light from the light source passes and is thus diffused. In those embodiments of the invention where the system includes two or more illumination elements, the illumination elements may emit light of the same wavelength or they may be spectrally distinct light sources, where by "spectrally distinct" is meant that the light sources emit light at wavelengths that do not substantially overlap, such as white light and infra-red light. In certain embodiments, an illumination configuration as described in U.S. Pat Pub. Nos. US20100121139A1 and US20100121142A1 (the entire disclosures of which are herein incorporated by reference) is present in the device.

In some embodiments, devices of the embodiments described herein may include a linear mechanical actuator for linearly translating a distal end element of the device, such as a tubular body which surrounds a visualization element relative to the visualization element. By "linearly translating" is meant moving the element along a substantially straight path. As used herein, the term "linear" also encompasses movement in a non-straight (i.e., curved) path.

In some embodiments, an integrated articulation mechanism that imparts steerability to the distal end of the elongated body and/or distal end of the visualization element is also present in the device. By "steerability" is meant the ability to maneuver or orient the visualization element, tissue modifier and/or distal end of the elongated body as desired during a procedure, e.g., by using controls positioned at the proximal end of the device. In these embodiments, the devices include a steerability mechanism (or one or more elements located at the distal end of the elongated body) which renders the desired distal end component maneuverable as desired through proximal end control. As such, the term "steerability", as used herein, refers to a mechanism that provides a user steering functionality, such as the ability to change direction in a desired manner, such as by deflecting the primary viewing axis left, right, up or down relative to the initial axial direction.

The steering functionality can be provided by a variety of different mechanisms. Examples of suitable mechanisms include, but are not limited to one or more axially moveable pull or push wires, tubes, plates, meshes or combinations thereof, made from appropriate materials, such as shape memory materials, music wire, etc. For example, one active deflection mechanism includes providing a plurality of transverse slots spaced apart axially along a first side of the outer tubular body 1126 within the distal segment. A second side of the outer tubular body 1126 within the distal segment, opposite from (i.e., 180° from) the first side acts as an axially non-compressible spine, while the first side may be compressed axially causing a lateral deflection concave in the direction of the first side. Axial compression (or elongation) of the first side relative to the second side, to induce or remove curvature, may be accomplished by an axially movable control wire. The distal end of the control wire may be secured to the outer tubular body 1126 within the distal segment 1108, preferably at the distal end of the distal segment. The control wire extends proximally throughout the length of the outer tubular body 1126, to a proximal deflection control. Manipulation of the control to retract the control wire proximally will collapse the transverse slots, shortening the axial length of the first side relative to the second side, thereby deflecting the distal segment.

In some instances, the distal end of the elongated body is provided with a distinct, additional capability that allows it to be independently rotated about its longitudinal axis when a significant portion of the operating handle is maintained in a fixed position, as discussed in greater detail below.

The extent of distal primary viewing axis articulations of the invention may vary, such as from at least about 5, 10, 25, or 35 degrees or more from the primary viewing axis. The visualization element may be configured for rotating about its axis so that the full range of angles is accessible on either side of the axis of the probe, essentially multiplying the effective viewing angle e.g., as described in greater detail below. Articulation mechanisms of interest are further described in published PCT Application Publication Nos. WO 2009029639; WO 2008/094444; WO 2008/094439 and WO 2008/094436; the entire disclosures of which are herein incorporated by reference. Specific articulation configurations of interest are further described in connection with the figures, below.

In some embodiments, the distal end of the elongated body 1102 is rotatable about its longitudinal axis when a significant portion of the operating handle is maintained in a fixed position. As such, at least the distal end 1108 of the elongated body 1102 can turn by some degree while the handle attached to the proximal end of the elongated body 1102 stays in a fixed position. The degree of rotation in a given device may vary, and may range from 0 to 360, such as 0 to 270, including 0 to 180 degrees.

As described herein this section and elsewhere in the specification, in certain embodiments, the device may be disposable or reusable. As such, devices of the invention may be entirely reusable (e.g., be multi-use devices) or be entirely disposable (e.g., where all components of the device are single-use). In some instances, the device can be entirely reposable (e.g., where all components can be reused a limited number of times). Each of the components of the device may individually be single-use, of limited reusability, or indefinitely reusable, resulting in an overall device or system comprised of components having differing usability parameters.

As described herein this section and elsewhere in the specification, in certain embodiments, devices of the invention may be fabricated using any convenient materials or combination thereof, including but not limited to: metallic materials such as tungsten, stainless steel alloys, platinum or its alloys, titanium or its alloys, molybdenum or its alloys, and nickel or its alloys, etc.; polymeric materials, such as polytetrafluoroethylene, polyimide, PEEK, and the like; ceramics, such as alumina (e.g., STEATITE™ alumina, MAECOR™ alumina), etc. In some embodiments, materials that provide both structural as well as light piping properties may be used.

As summarized above, some embodiments of the invention include visualization sensors and illumination elements. In certain embodiments these visualization sensors are positioned within a handle at the proximal end of the device. The system may include one or more visualization sensors at the proximal end of the device and one or more illumination elements that are located among the distal and/or proximal ends of the elongated body. In particular embodiments, one or more visualization sensors, such as those described in this section or elsewhere in the specification, may be located in the distal end of the device such as within the distal end of the elongated body. In some embodiments, one or more visualization sensors may be located at various locations within the elongated body, such as at approximately one-quarter the length of the elongated body from the distal end, one-half, or three quarters the length of the elongated body from the distal end. In certain embodiments, the visualization sensors may be miniaturized such that they do not substantially increase the outer diameter of the elongated body.

Similarly, in embodiments, one or more illumination elements may be located at the distal and/or proximal end of the elongated body. Embodiments of the systems also include those systems where one illumination element is located at the distal and/or proximal end of the elongated body and another illumination element is located at the distal and/or proximal end of the access device. Furthermore, embodiments of the systems include those systems where one or more illumination elements are located at the proximal end of the device and light is propagated via wave guides such as a fiber optic bundle towards the distal end of the device. A longest cross section dimension for the elongated body is generally 20 mm or less, 10 mm or less, 6 mm or less, such as 5 mm or less, including 4 mm or less, and even 3 mm or less.

Figure 4:
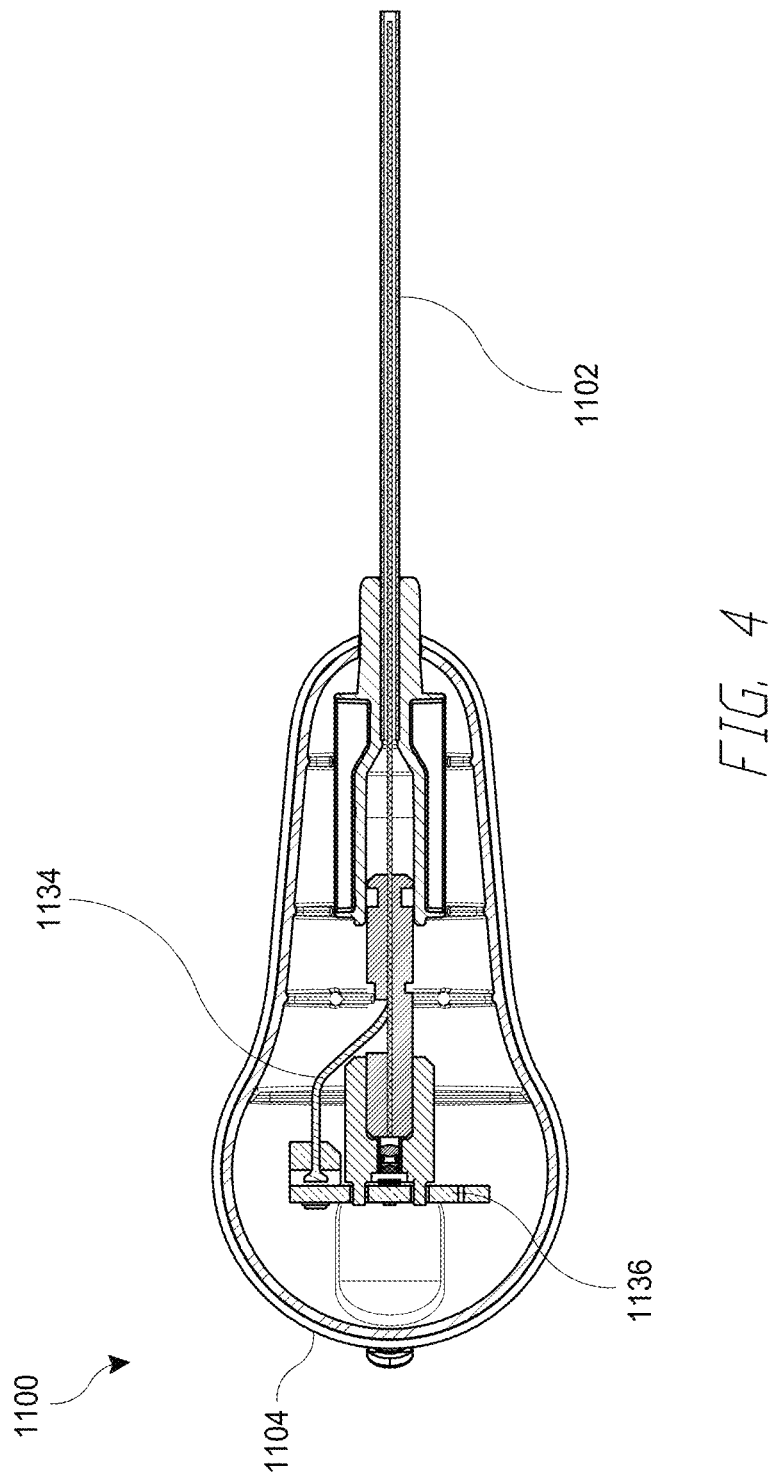
FIG. 4 illustrates a cross-sectional top view of an embodiment of a clot evacuation device.

FIG. 4 depicts a cross-sectional top view of an embodiment of the clot evacuation device 1100. The handpiece 1104 comprises an illumination element 1134 and a visualization sensor support 1136, described in greater detail below. Similar to illumination elements or apparatuses described elsewhere in this specification, the illumination element 1134 may extend down the length of the elongated body 1102 and convey light down the elongated body 1102 to an interior tissue site to allow for visualization of the target tissue. In some embodiments, the illumination element 1134 comprises a bundle or bundles of illumination fibers.

Figure 5A:
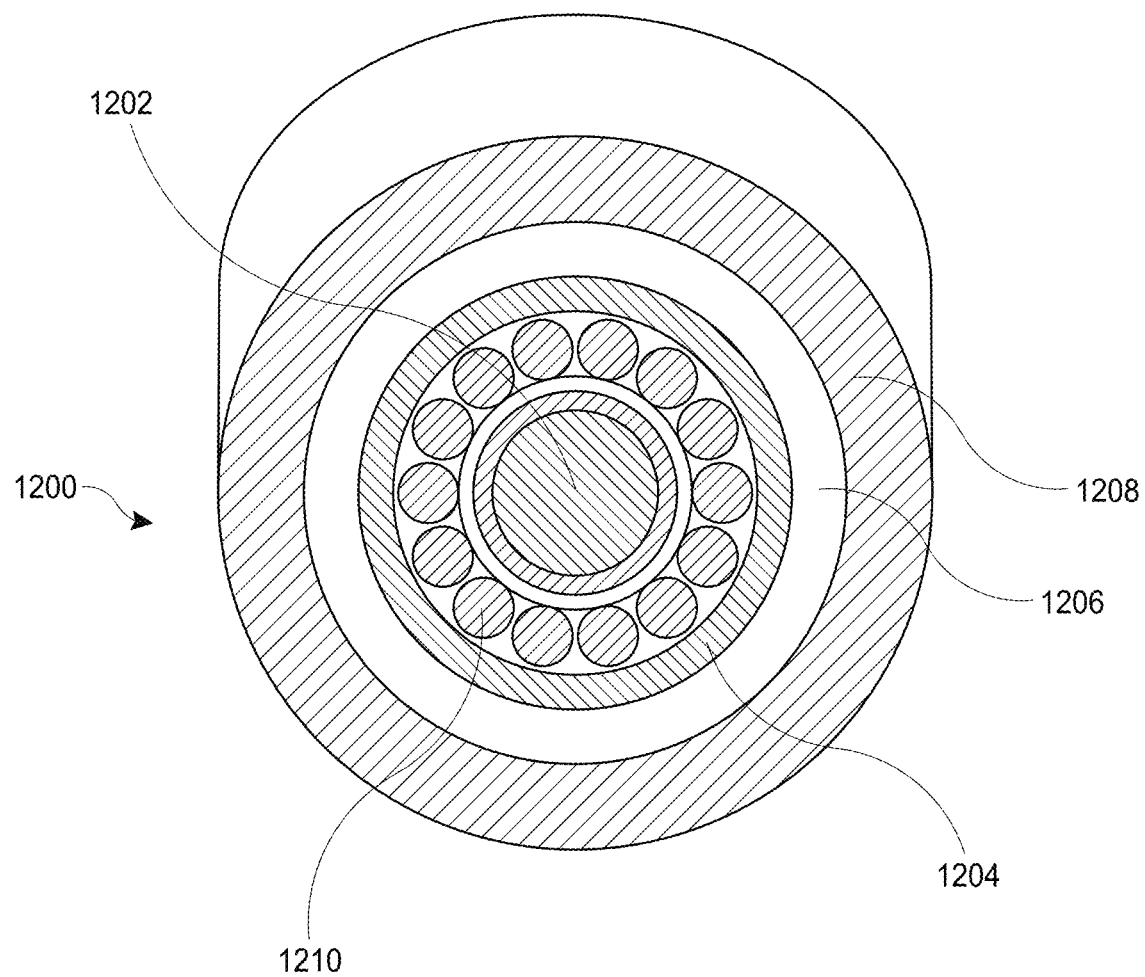
Figure 5G:
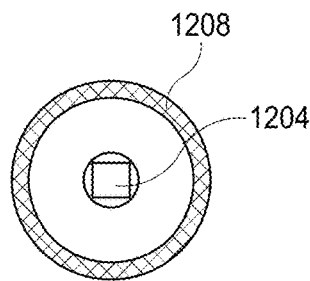
Figure 5H:
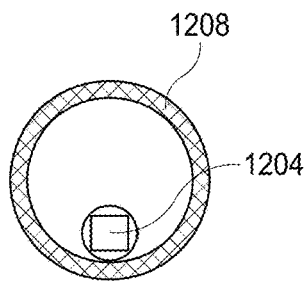

FIG. 5A illustrates cross sectional views of an embodiment of a clot evacuation device down the length of the elongated body 1200, similar to the elongated bodies depicted in FIGS. 1-4. In certain embodiments, the hypotube 1204 may comprise an image guide 1202 (which may be enclosed in one or more layers of tubing), at least one illumination fiber or fiber bundle 1210, an infusion lumen 1206, and outer tubular body 1208. As will be understood by one skilled in the art, the use of the term "illumination fiber" here encompasses an illumination fiber or fiber bundle. As described elsewhere in the specification, the illumination fibers or fiber bundles may be configured to transmit a wavelength of light suitable for illuminating a target tissue for visualization; however, the illumination fibers may also be configured to transmit UV and/or infrared light to a tissue site. For example, if there are 14 total illumination fibers or fiber bundles, then 7 may be configured to deliver light suitable for visualization while another 7 may be suitable for delivering UV light. However, any suitable combination may be used. For example, most of the illumination fibers may be UV, half of the illumination fibers, or less than half. In particular embodiments, the number of illumination fibers may be increased or decreased from the number depicted in FIG. 5. For example, there may be one fiber, at least two fibers, at least 5 fibers, at least 10 fibers, at least 14 fibers, at least 20 fibers, at least 25 fibers, at least 50 fibers, or more than 50 fibers. In certain embodiments, the illumination fibers may be configured to output multiple wavelengths of light suitable for imaging an internal tissue site.

The wavelength of light delivered via illumination fibers 1210 [which can be at least 4, 8, 12 or more fibers or bundles of fibers, and which may be arranged in an annular configuration surrounding the image guide 1202 as shown in FIG. 5A but described in detail below] may be selected for various wavelength specific applications. For example, wavelengths in the UV and/or infrared range can be utilized to permit visual differentiation of tissue types such as to distinguish nervous tissue from surrounding tissue and/or minimally vascularized nervous tissue. Blood vessels may appear to have a first color (such as red) while nerve tissue may appear to have a second color (such as blue). The wavelength may also be optimized to distinguish nervous tissue from blood.

Another wavelength specific application involves directing a preselected wavelength to a target impregnated with a drug or drug precursor. Upon delivery of the preselected wavelength to the target, drug is released, or the precursor is converted into a drug which is then released. The target may be an implanted mass or device, or an infused carrier medium such as any or a combination of a liquid, gel, or beads.

The UV light may include Ultraviolet A, long wave, or black light, abbreviated "UVA" and having a wavelength of 400 nm-315 nm; Near UV light, abbreviated "NUV" and having a wavelength of 400 nm-300 nm; Ultraviolet B or medium wave, abbreviated "UVB" and having a wavelength of 315 nm-280 nm; Middle UV light, abbreviated "MUV" and having a wavelength of 300 nm-200 nm; Ultraviolet C, short wave, or germicidal, abbreviated "UVC" and having a wavelength of 280 nm-100 nm; Far UV light, abbreviated "FUV" and having a wavelength of 200 nm-122 nm; Vacuum UV light, abbreviated "VUV" and having a wavelength of 200 nm-400 nm; Low UV light, abbreviated "LUV" and having a wavelength of 100 nm-88 nm; Super UV light, abbreviated "SUV" and having a wavelength of 150 nm-10 nm; and Extreme UV light, abbreviated "EUV" and having a wavelength of 121 nm-10 nm. In some embodiments, the catheters may include an element that emits visible light. Visible light may include violet light having a wavelength of 380-450 nm; blue light having a wavelength of 450-475 nm; cyan light having a wavelength of 476-495 nm; green light having a wavelength of 495-570 nm; yellow light having a wavelength of 570-590 nm; orange light having a wavelength of 590-620 nm; and red light having a wavelength of 620-750 nm. In some embodiments, the catheter includes an element that emits light having a wavelength between about 300 nm and 500 nm. In particular, the catheter may include an element that emits light having a wavelength associated with blue light (e.g., light having a wavelength between about 450-475 nm). Wavelength selection information and characterization and other details related to infrared endoscopy are found in U.S. Pat. No. 6,178,346; US Patent Application Publication No. 2005/0014995, and US Patent Application Publication No. 2005/0020914, each of which is hereby incorporated by reference in its entirety.

In certain embodiments, the outer diameter of the hypotube 1204 may range from approximately 0.1 mm to 0.3 mm, approximately 0.5 mm to 2.5 mm, or approximately 1 mm to 2 mm. In certain embodiments, the outer diameter of the hypotube 1204 is approximately 1.27 mm. In some embodiments, the inner diameter of the outer tubular body 1208 ranges from approximately 0.1 mm to 10 mm, approximately 0.2 mm to 8 mm, approximately 0.5 mm to 6 mm, approximately 1 mm to 5 mm, approximately 1.2 mm to 4 mm, or approximately 1.4 mm to 3 mm. In certain embodiments, the inner diameter of the outer tubular body 1208 is approximately 1.6 mm.

In some embodiments, the image guide 1202 allows for the viewing of an image of the tissue site by the visualization sensor in the handpiece. In particular embodiments, the image guide may be a fiber optic or other suitable medium to allow for imaging of the tissue site by a visualization sensor as described herein this section or elsewhere in the specification. The fiber optic bundle may have at least about 6K, or at least about 10K or at least about 15K or at least about 30K fibers or more, depending upon the desired performance. In some embodiments, the image fiber may be a 6.6 k fiber bundle or a 10 k fiber bundle.

FIGS. 5B-5F describe and depict embodiments of the distal end of a clot evacuation device, similar to the devices depicted in FIGS. 1-5A. However, in these embodiments, the visualization element may be positioned in a different location than as described in FIG. 2. The hypotube 1204 may be a visualization channel 1205 in the outer tubular body 1208. For example, in these embodiments, the visualization channel 1205 is merged with the outer tubular body 1208 and runs along the length of the elongate body. In certain embodiments, additional channels 1207 may also run along the outer tubular body 1208 to provide irrigation for flushing in the form of a saline "jet." In some embodiments, such as shown in FIGS. 5B and 5C, the visualization channel 1205 comprising optical elements, such as a hypotube 1204, is merged with the outer tubular body and positioned on the inner surface of the outer tubular body 1208. In some embodiments, such as shown in FIG. 5D, the visualization channel 1205 is merged with the outer tubular body 1208, but positioned outside of the diameter of the outer tubular body 1208. In some embodiments, such as shown in FIG. 5E, the visualization channel 1205 is merged with the outer tubular body 1208, but positioned internally between the inner and outer diameters of the outer tubular body 1208. As shown in FIG. 5F, retraction of the visualization element (e.g., hypotube 1204) into the visualization channel 1205 can position the distal end of the visualization element near a "fluid jet" (e.g., saline jet) for washing fluid across the surface of the visualization element. The jet may be angled downward via a post-molding machine operation. While these concepts can restrict the size of the working channel (e.g. visualization channel 1205 disposed on the inner surface of the outer tubular body 1208) or make the cross-section of the outer tubular body 1208, which translates through tissue, non-circular or asymmetric (e.g., visualization channel 1205 disposed on the outer surface of the outer tubular body 1208), the impacts of these configurations can be mitigated. For example, the working channel of the outer tubular body 1204 can be used for evacuation and/or irrigation, eliminating the need to insert any additional instruments through the working channel.

Figure 5I:
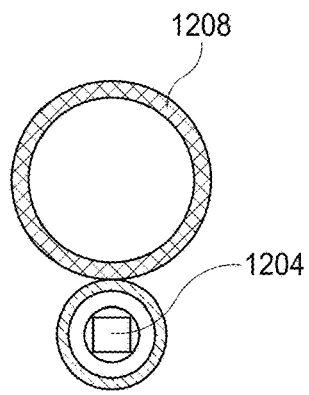
Figure 5J:
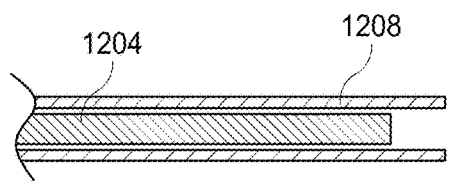
Figure 5K:
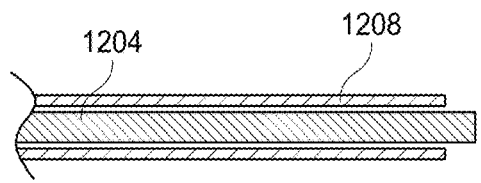
Figure 5L:
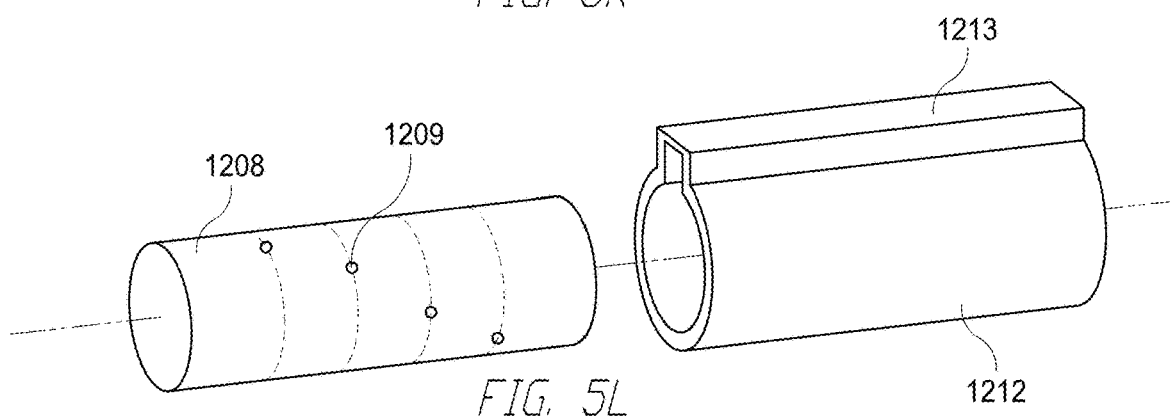
Figure 5M:
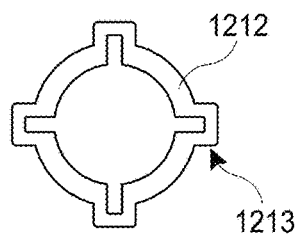

FIGS. 5G-5M describe and depict embodiments of the clot evacuation device, similar to the devices depicted in FIGS. 1-5B. For example, the hypotube 1204, comprising visualization elements (e.g., imaging, illumination, non-visible wavelengths such as IR, UV, etc.), may be positioned in the center of the outer tubular body 1208 (FIG. 5G), against an inner wall of the outer tubular body 1208 (FIG. 5H), or positioned outside of the outer tubular body 1208 (FIG. 5I). In certain embodiments, as described above and as schematically depicted in FIG. 5J, the hypotube 1204 may be retracted to interact with a cleaning station to wipe, irrigate, and/or blot the lens or to view tissue in "tunnel vision" if soft tissue is interfering with the visualization. In a "normal" un-retracted position, the hypotube 1204 may extend to be flush with the outer tubular body 1208 or may extend distally beyond the outer tubular body 1208, as schematically depicted in FIG. 5K. In certain embodiments, as described elsewhere in the specification, an outer sleeve 1212 may be applied around the outer tubular body 1208 to provide irrigation to a target tissue and/or tissue clot and/or to the lens for cleaning. The outer tubular body 1208 may comprise irrigation inlets 1209 longitudinally and/or circumferentially spaced about the elongate body. The outer sleeve 1212 may comprise one or more irrigation channels 1213, as shown in FIGS. 5L and 5M for directing irrigation fluid over the various irrigation inlets 1209. The outer sleeve 1212 can be rotated about the outer tubular body 1208 to supply different irrigation channel(s) 1213 with fluid.

Figure 6A:
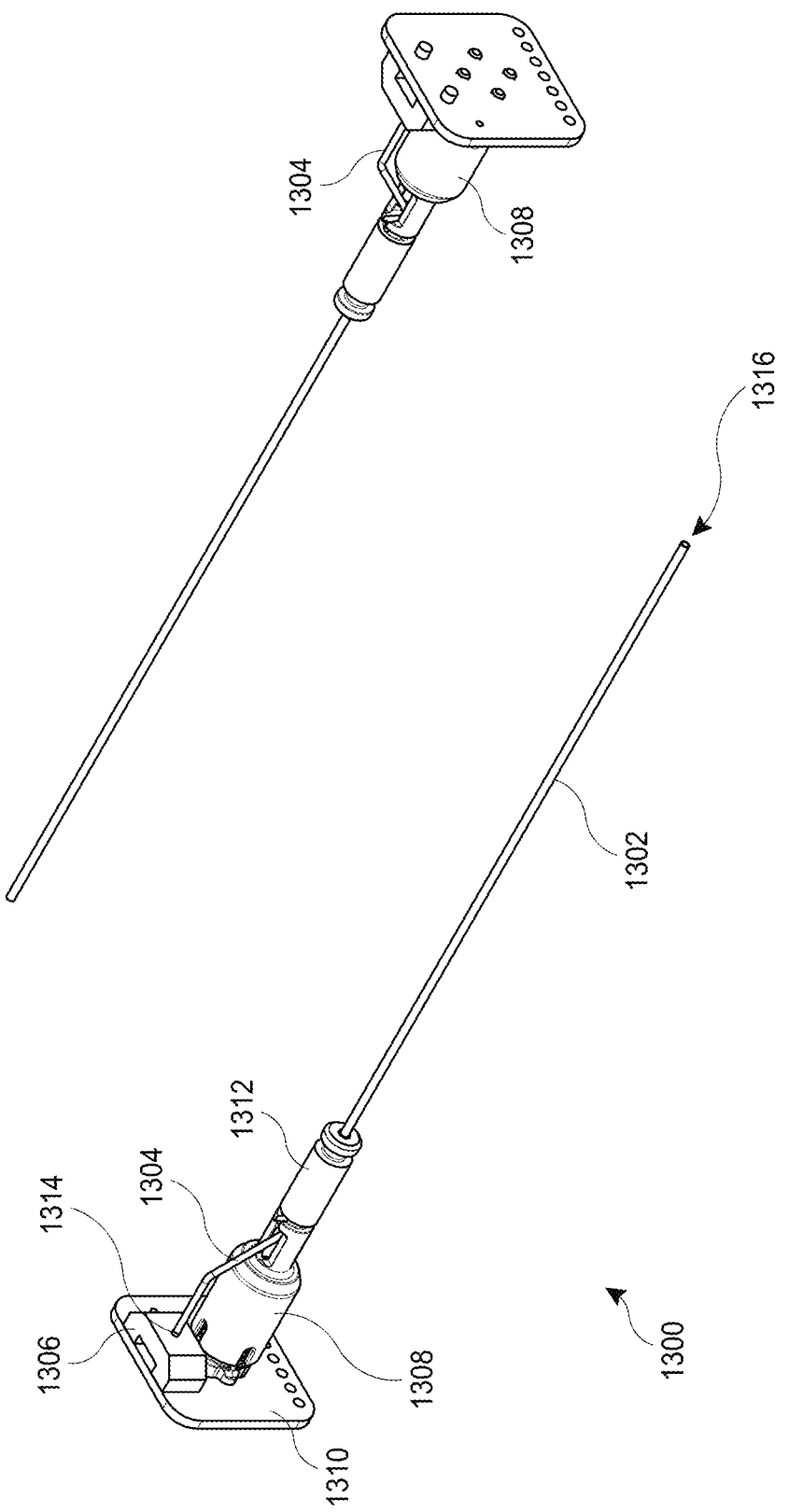
FIGS. 6A-C illustrate embodiments of a clot evacuation device with the outer housing removed.
Figure 6B:
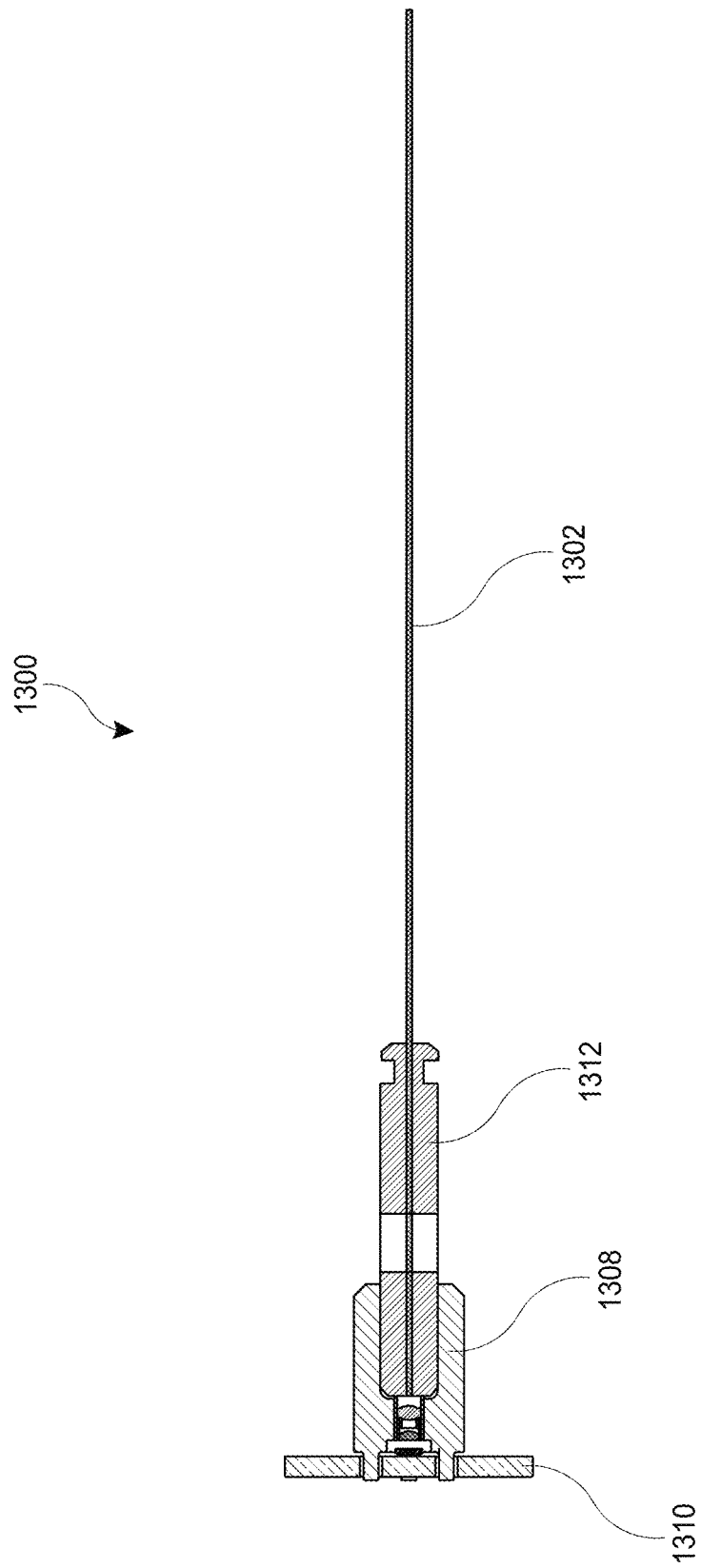
Figure 6C:
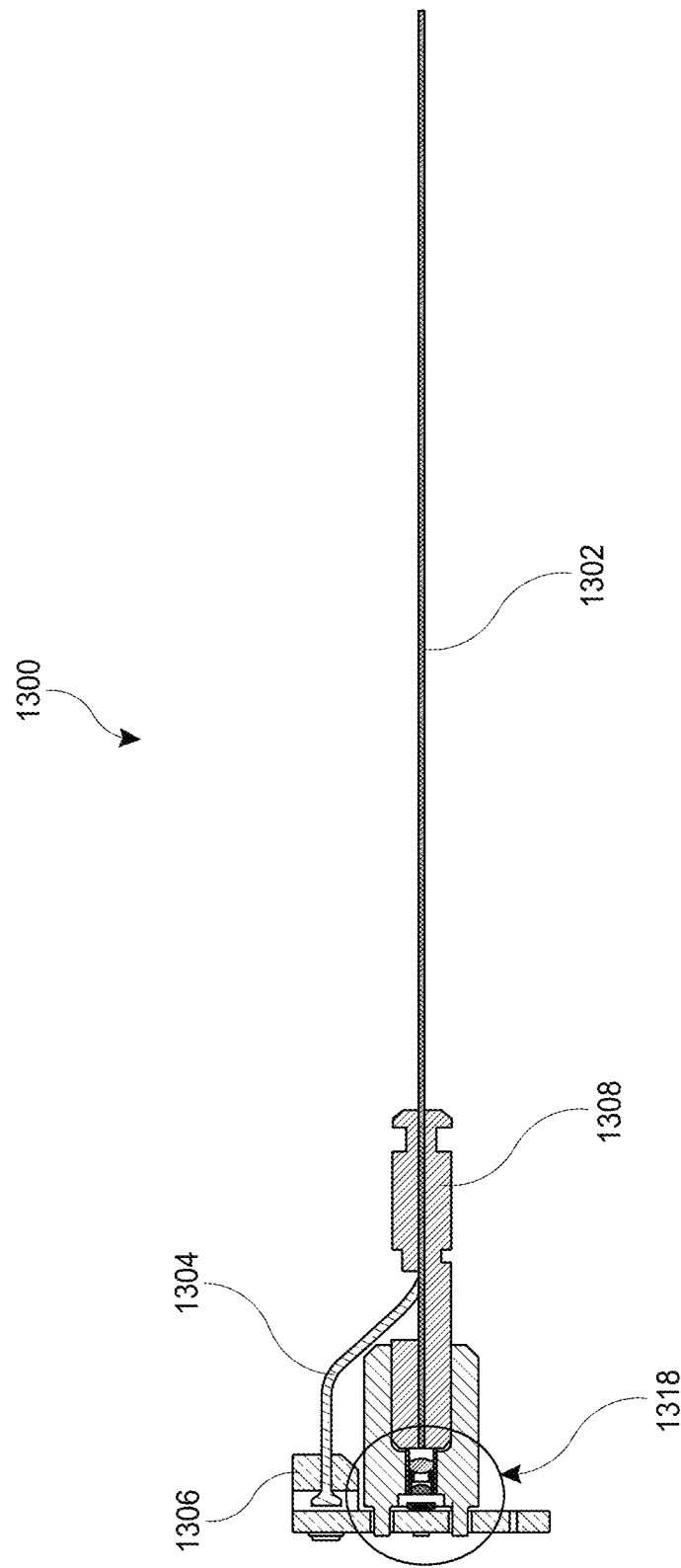

FIGS. 6A-C illustrate embodiments of the elongated body and inner components of a clot evacuation device 1300, similar to the embodiments depicted herein this section or elsewhere in the specification. In these particular figures, the outer shell of the handpiece is removed to better view the interior of the device. In certain embodiments, the clot evacuation device comprises an elongated body 1302, an illumination element 1304 (in some embodiments the illumination element 1304 may be replaced by an electrical cable, such as when an LED is positioned at the distal end of the elongate body 1302), light source housing 1306, a printed circuit board 1310, a proximal lens housing 1308, a ferrule 1314, a nosepiece 1312, and a distal lens 1316.

FIG. 6B illustrates a top view of the visualization complex (without illumination elements) of clot evacuation device 1300 of FIG. 6A, while FIG. 6C illustrates a side view. The components in these figure are similar to the components illustrated in FIG. 6A, however in FIG. 6C, the visualization complex is identified as 1318. The visualization complex 1318 and surrounding components can be viewed in more detail in FIG. 7.

Figure 7:
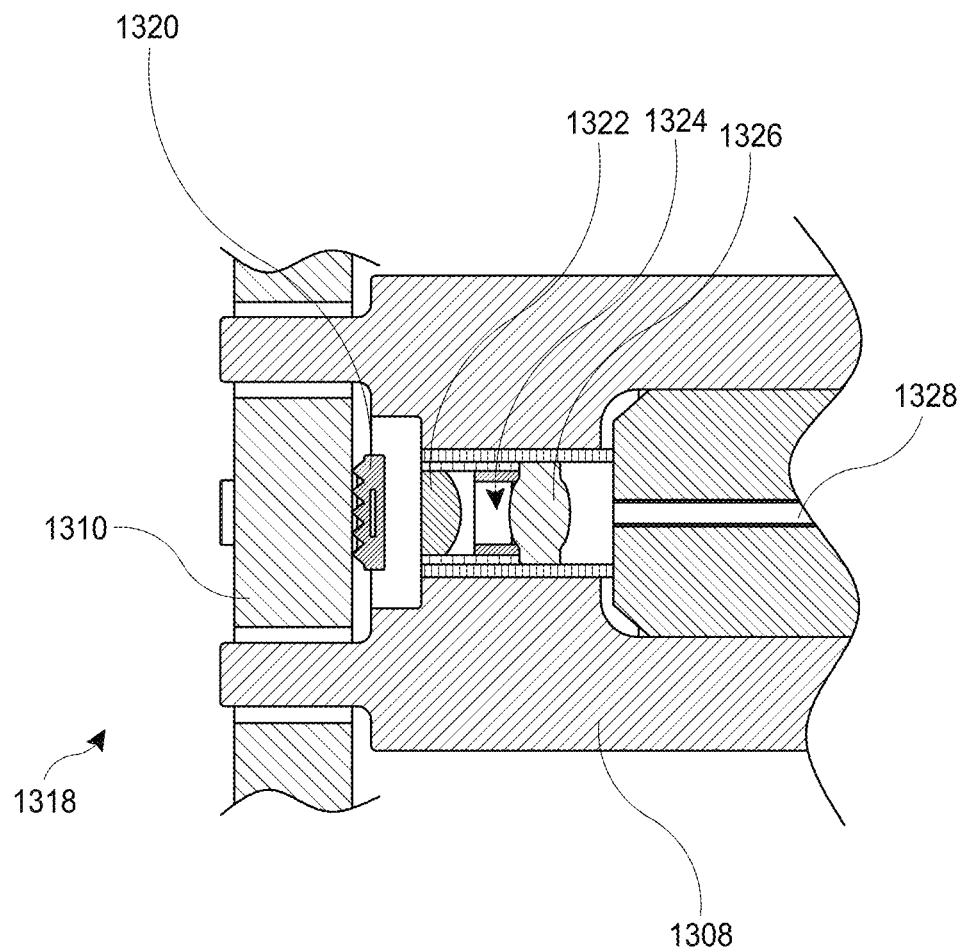
FIG. 7 illustrates a cross-sectional side view of an embodiment of the lens housing depicted in FIG. 6A-C.

FIG. 7 illustrates a cross-sectional side view of an embodiment of the visualization complex of FIG. 6C. In some embodiments, the visualization complex 1318 may comprise a visualization sensor 1320 such as those visualization sensors described herein this section or elsewhere in the specification. In certain embodiments, the visualization sensor 1320 may be a CMOS sensor as described herein this section or elsewhere in the specification. However, as described elsewhere in the specification, a visualization sensor 1320 may be located at the distal tip of the inner hypotube.

In certain embodiments, the visualization complex 1318 can comprise a first lens 1322, an optical aperture 1324, and a second lens 1326. In some embodiments, the aperture may have a diameter of at least about 0.1 mm, at least about 0.2 mm, at least about 0.3 mm, at least about 0.5 mm, or more than 0.5 mm. Preferably, the aperture may be approximately 0.222 mm. To support the lenses, the visualization complex 1318 may comprise a proximal lens housing 1308 as described previously, wherein the proximal lens housing 1308 may serve to secure the lenses 1322 and 1326 in the proper location and orientation. The visualization complex 1318 may further comprise an image guide 1328, similar to the image guide described previously in relation to FIG. 5A.

As illustrated in FIG. 1 and FIG. 8A, one consequence of the integrated visualization device of the present invention is that rotation of the visualization device 4 about the central longitudinal axis to achieve the enlarged field of view will simultaneously cause a rotation of the apparent inferior-superior orientation as seen by the clinician on the display such as video screen 19 of FIG. 1 or image 1501 of FIG. 8A. It may therefore be desirable to compensate such that a patient reference direction such as superior will always appear on the top of the screen 19, regardless of the rotational orientation of the visualization device 4, such as depicted in image 1503 of FIG. 8B.

This may be accomplished by including one or more sensors or switches carried by the clot evacuation device 4, that are capable of generating a signal indicative of the rotational orientation of the visualization sensor 1132. The signal can be transmitted via wire or wireless protocol to the controller 6 for processing and correction of the rotational orientation of the image on screen 19 or other display, to stabilize the image.

Suitable sensors may include simple tilt or orientation sensors such as mercury switches, or other systems capable of determining rotational orientation relative to an absolute reference direction such as up and down. Alternatively, the rotational orientation image correction system may comprise a 3-axis accelerometer with associated circuitry such as a small accelerometer constructed with MEMS (micro-electro mechanical systems) technology using capacitance measurement to determine the amount of acceleration, available from Freescale Semiconductor, Inc., of Austin, Tex. and other companies.

As an alternative or in addition to the accelerometer, the visualization device may carry a gyroscope such as a three-axis gyroscope. The output of the gyroscope may be the rate of change of roll angle, pitch angle and yaw angle and rotational rate measurements provided by the gyroscope can be combined with measurements made by the accelerometer to provide a full six degree-of-freedom description of the sensor 1132's motion and position, although that may not be necessary to simply correct for rotational orientation. A control may be provided on the handpiece 4 or controller 6, allowing the clinician to select what reference orientation (e.g., patient superior, inferior, true up or down, etc. or true sensor view such that the image on the screen rotates with the sensor) they would like to have appearing at the top of the screen regardless of sensor orientation. In certain embodiments, markers such as an arrow or line may be projected onto the image to further identify different orientations and/or directions In some embodiments, the hypotube may be sheathed in heat shrink tubing. For example, the outer tubular body as described elsewhere in the specification, may be constructed from a heat-sensitive material. Thus, to construct the elongated body as described elsewhere in the specification, the hypotube and other components may be extended down an over-sized outer tubular body which is then shrunk down to the diameter of the hypotube via means such as heat, UV, chemical, or other means. In contrast, traditional endoscopes and some endoscopes described elsewhere in the specification house the optics in a rigid stainless steel tube. However, housing the optics within a stainless steel tube may require forcing many optical and illumination fibers down a very tight ID and then applying an adhesive such as epoxy. Such a process is difficult and costly.

In certain embodiments, a desired direction of view may be reached by positioning a prism at the distal end of the elongated body. Such a prism may provide a direction of view such as disclosed elsewhere in the specification, for example: providing a direction of view 30 degrees from the axis of the elongated body. In some embodiments, the angle may be much smaller, such as between 0-15 degrees. In further embodiments the angle may range from 15-45 degrees. In some embodiments, the angle may be at least 45 degrees, at least 60 degrees, at least 75 degrees or at least 90 degrees or more.

In some embodiments, the elongated body may be in a shape that is non-circular. For example, the entirety of the elongated body may be oval or elliptical in shape. In some embodiments, only the distal end of the elongated body is oval-shaped while the remainder of the elongated body is circular. An oval shaped elongated body advantageously allows for additional space for the deflected distal tip. In certain embodiments, the major axis of the ellipse is approximately 1.1 times as long as the minor axis. In some embodiments, the major axis is at least 1.2 times, 1.3 times, 1.5 times, 1.75 times, 2 times, 3 times, 4 times, 5 times, or more than 5 times as long as the minor axis.

In particular embodiments, the distal tip of the elongated body may be constructed from elastic material to allow the distal tip to flex distally. Further, the deflected portion of the distal tip may be very short, allowing the deflected portion to stay within the outer perimeter confines of the elongated body.

In certain embodiments, the distal end of the elongated body may be rotated with respect to the hypotube. For example, the elongated body may comprise a sharpened distal point which may be under the hypotube, over the top of the hypotube, or on a side of the hypotube. In certain embodiments, the hypotube may act as a shield to prevent the sharpened distal point from damaging the surrounding tissue in any orientation. In certain embodiments, the hypotube may comprise a shield at the distal tip, the shield acting to protect the surrounding tissue from the sharpened distal tip of the elongated body. Upon rotation of the hypotube, the shield may be moved from the sharpened distal tip of the elongated body, allowing for further penetration through tissue.

Figure 9A:
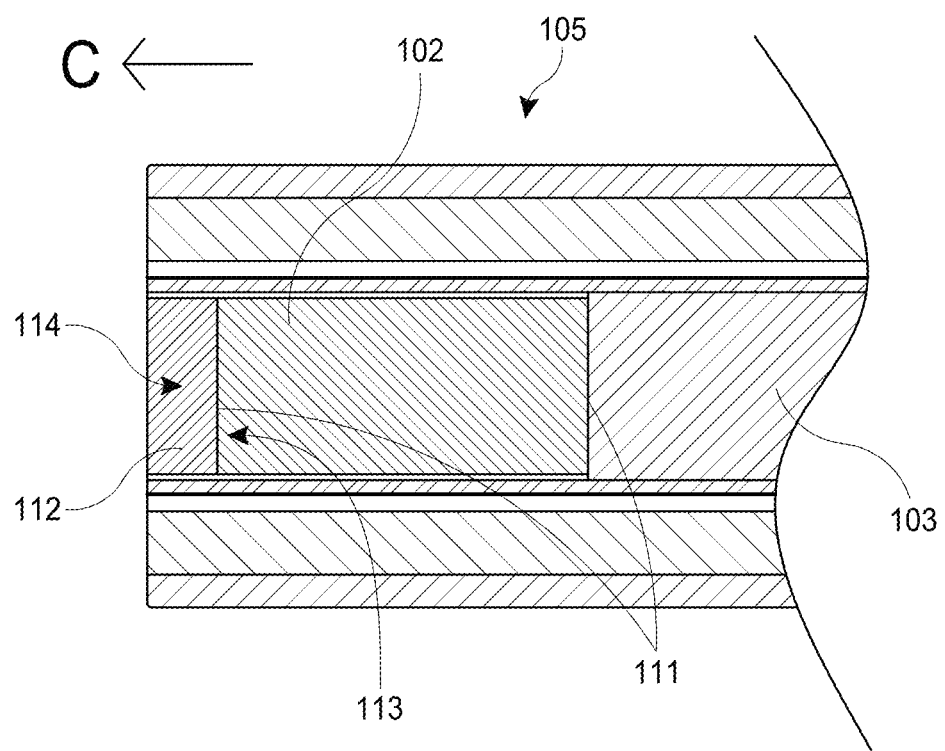
FIGS. 9A-C illustrate various side and front views of embodiments of a clot evacuation device.

FIG. 9A illustrates an embodiment of the distal end of a clot evacuation device, similar to the clot evacuation devices depicted in FIGS. 1-8B. Here, the arrow "C" indicates the distal direction towards the tissue site. The distal end of the elongated member 105 comprises an optical fiber 103, similar to the hypotubes and optical elements described elsewhere in the specification. Distal lens 102 may comprise any type of lens described herein this section or elsewhere in the specification, including a GRIN (Gradient-index) lens. The lens may have a diameter of between about 100-700 microns, about 200-600 microns, about 400-500 microns, or about 465 microns.

In certain embodiments, as depicted in FIG. 9A, the distal end of the clot evacuation device may include a circular transparent plate 112, such as a glass plate or other suitable transparent material. In the embodiment depicted in FIG. 9A, the plate is non-powered, however in some embodiments the plate may be powered to have magnification levels of about 2×, 4×, 10×, 20×, 100×, or greater than 100×. The plate may be flat on both sides of the plate, rounded on both sides of the plate, or rounded on one side and flat on the other side. In certain embodiments, the plate 112 may have a diameter of between about 100-700 microns, about 200-600 microns, about 400-500 microns, or about 465 microns. In certain embodiments, an adhesive 111 adheres the plate to the distal lens 102, and the distal lens 2 is adhered to the optical fiber 103 by another adhesive 111.

In embodiments, and as depicted in FIG. 19A, the plate 112 may include a mask 113 on the proximal side of the plate 112, surrounding a transparent window 114. However, in certain embodiments, the mask 113 may be on the distal side of the plate 112. By placing the mask 113 on the proximal side of the plate 112, potentially toxic mask materials are prevented from interacting with tissue. The mask 113 may comprise any suitable material that limits transmission of light such as a chrome coating. However, any suitable evaporative coating may be used such as different metallic materials.

The window 114 encompasses an area of the plate not covered by the mask 113, thereby allowing light to pass through the window 114. As described in more detail in relation to FIG. 12 below, the mask may be applied in an annular region of the plate 112, thereby creating a rounded window 114.

In particular embodiments, the mask 113 acts to limit the transmission of light through the plate 112. For example, the mask may restrict the gathering of all the angles of light reflecting from the object being viewed (e.g. tissue site). The overlap of light rays on the image is therefore very small and the result is a sharper image over a wider depth of field. Although this may reduce the brightness of the image, the image is much sharper. In certain embodiments, the material of the mask allows at most about 0% transmission of light through the material, about 2%, about 4%, about 5% or about 10%. Further, the mask preferably absorbs light rather than reflects light to limit stray light from affecting the sharpness of the image. In embodiments, the material of the mask may reflect at most about 0% of the light impacting the surface, about 5%, about 10%, about 20%, about 25%, or about 30%. In certain embodiments, the reflectivity at 400 nm of light may be 12%, at 500 nm-20%, at 600 nm-27%, at 700 nm-33%.

The circular plate 112 may be sized to have the same diameter as the lens 102, however, in embodiments the plate 112 may be smaller than the lens 102, such as at least about: 10% of the size of the lens 102, 25%, 50%, 75%, or 90%. When the plate 112 is smaller than the lens 102, light may potentially leak through the plate 112 into the lens 102, thus in these scenarios an opaque adhesive or cover may be applied to the distal end of the lens 102 to limit the passage of light into the lens 102. In certain embodiments, the plate 112 may be non-circular such as rectangular or polygonal. As with the circular plate, the non-circular plate may be about: 10% of the size of the lens, 25%, 50%, 75%, or 90%. As with the smaller rounded plate, the non-covered regions of the lens 102 may be coated in an opaque adhesive to limit the transmission of light.

In certain embodiments, rather than using a transparent plate 112 with a mask 113, the plate 112 may be replaced with any suitable material comprising an aperture. For example a metal plate with a window may be used, or an opaque polymeric material.

Commonly in the field of imaging, when using a GRIN lenses such as those described herein this section or elsewhere in the specification, an optical mask such as described above in relation to the plate, would normally be placed between two GRIN lenses or at the focus point of the lens. However, here the mask is positioned between a non-powered plate and a powered lens. Further, although the mask may be placed in the focal point of the lens, here the mask need not be located at the focal point.

Figure 9B:
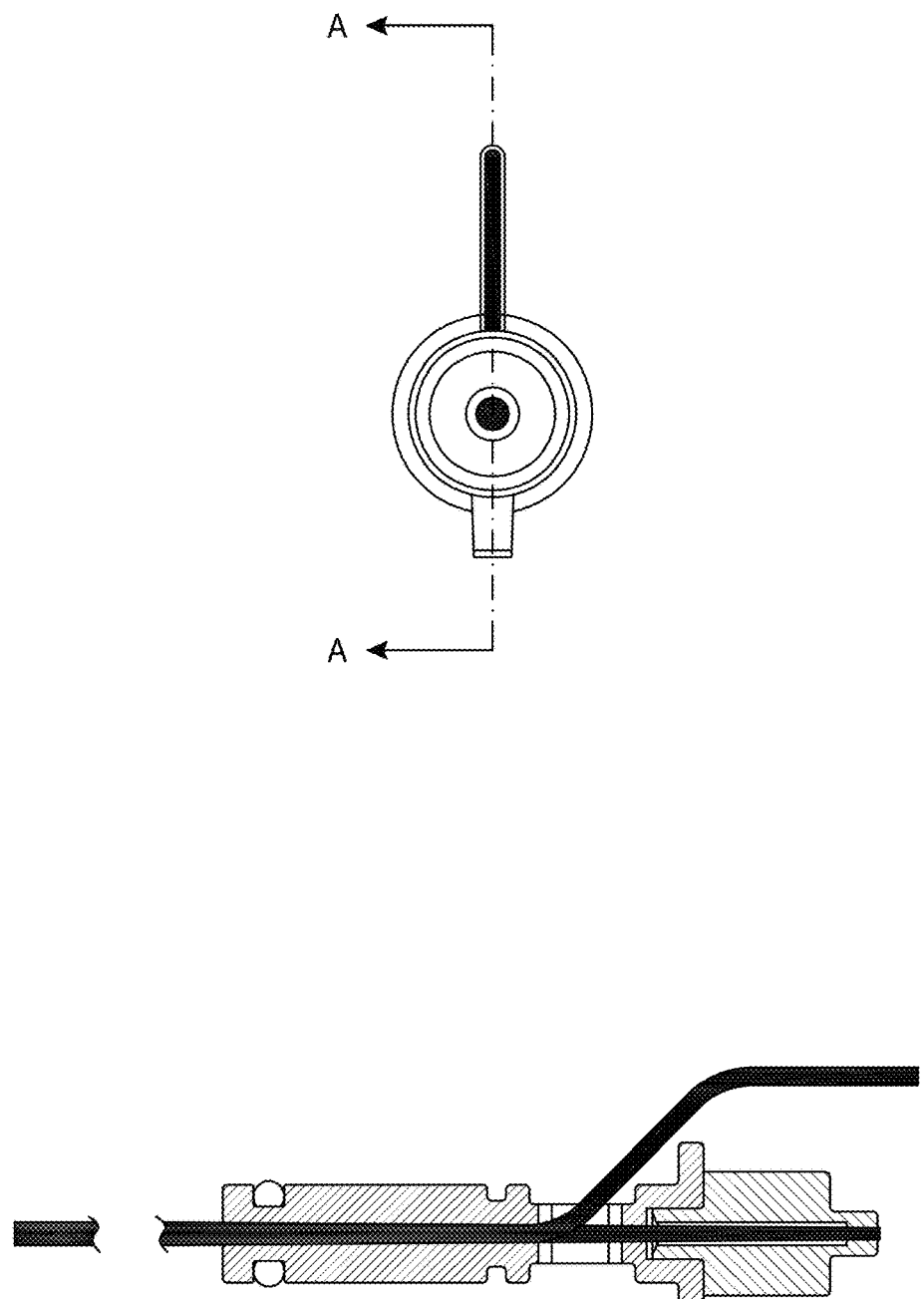

FIG. 9B illustrates a side and front view of embodiments of the clot evacuation device, similar to the embodiments depicted above. In further embodiments, a CMOS/CCD sensor may be located at the distal tip of the visualization device rather than a proximal location. With a distally mounted sensor, distally located LEDs may be utilized with or without a short light pipe rather than relying on illumination fibers to transmit the light from a proximal led.

Figure 9C:
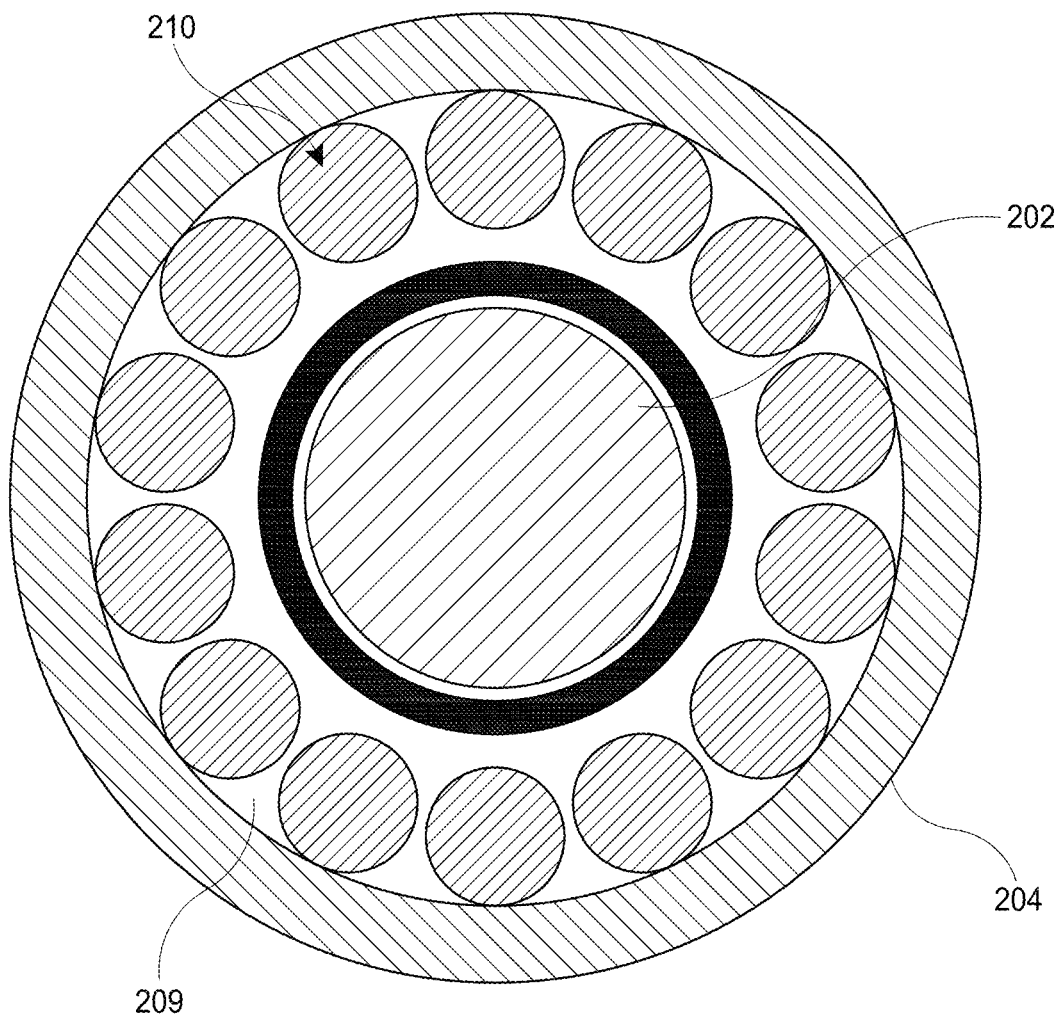

FIG. 9C illustrates a view along the elongate member of the visualization device, such as is depicted in FIG. 5A. Illumination fibers 210 are secured within epoxy 209 around a central optical element and/or image guide 202. In certain embodiments, the illumination fibers 210 can also be bunched to one side of the tubular body 204 with the imaging lens and fiber on the opposite side (the drawing has them around the circumference but may also be asymmetric).

FIG. 10 compares pictures of the interior of a red pepper imaged with a visualization device comprising the plate described above (right) and a visualization device without the plate (left). As can be viewed in the image, the addition of the plate dramatically improves the sharpness of the image.

Figure 11:
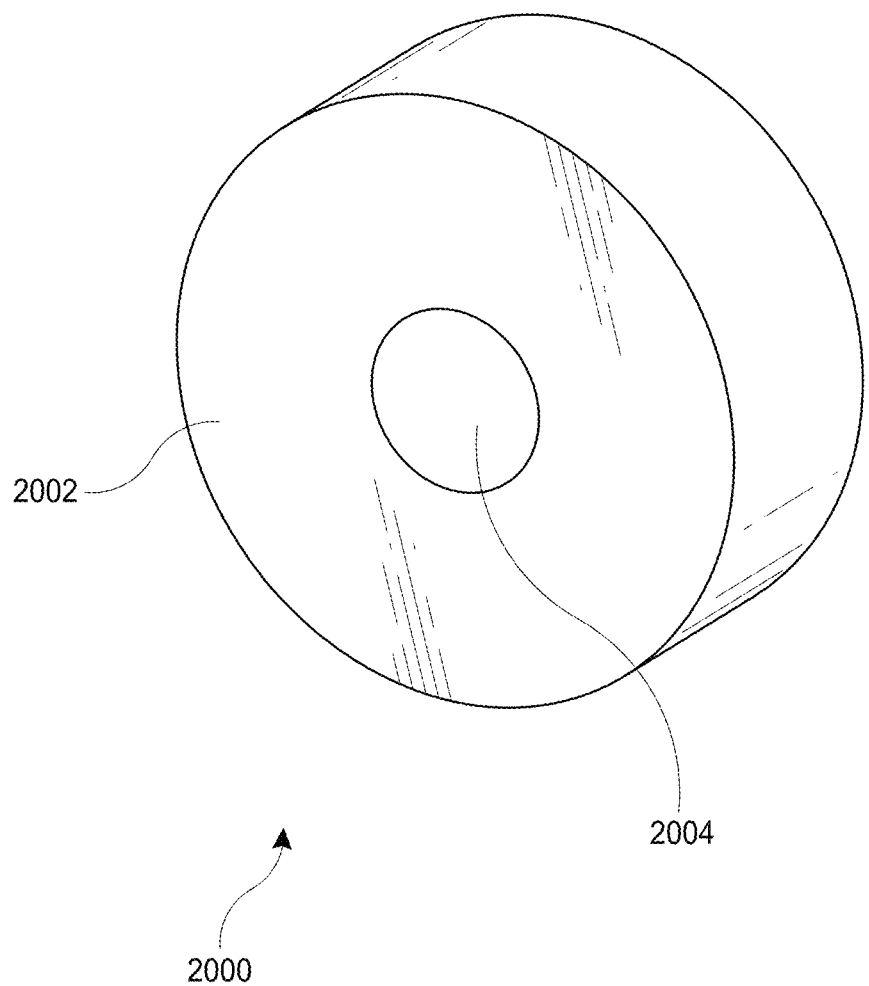
FIG. 11 is a close up view of an embodiment of a non-powered plate with an optical mask.

FIG. 11 depicts a plate 2000 such as the plate described above in relation to FIGS. 9A-C. Here the mask 2002 is annular and surrounds a transparent window 2004 that allows the passage of light. Although here the mask 2002 and window 2004 are depicted as annular, in other embodiments the mask 2002 and window 2004 may be rectangular, triangular, octagonal, or in the form of other suitable polygons. In certain embodiments the mask 2002 may cover at most: about 25% of the surface of a single side of the plate, about 50%, about 60%, about 70%, about 80%, about 90%, or about 95% of the surface area of one side of the plate 2000. In some embodiments, as described above, the plate 2000 may have a diameter of about 0.5 mm or any diameter described above, however, the window 2004 may have any suitable diameter corresponding to the percentages described above, for example the window 2004 may have a diameter of between about 50-200 microns, 75-150 microns, or about 100-125 microns. For example, the diameter may be 90 microns, 130 microns, or 150 microns.

In certain embodiments, the ratio between the diameter of the active area of the imaging element/imaging fiber to the diameter of the window 2004 may be approximately at least: about 2×, about 3×, about 4×, about 5×, about 6×, about 8×, about 10×, or more than 10×. In certain embodiments where the window 2004 is non-circular, the ratio of the area of the window 2004 to the active area of the imaging element or imaging fiber may be at least about 5×, about 10×, about 15×, or about 20×.

In certain embodiments, the distal end of the hypotube may be flared to accommodate a larger sensor than would ideally fit into the diameter of a standard hypotube. This flare could simply be a larger diameter cross-section, a square cross section or something to match what is within. The axial length of this flare would be to accommodate the length of the sensor plus routing of illumination fiber around the sensor and would have a transition zone back to the circular cross section of the normal hypotube. In embodiments, such an arrangement provides a lumen between the inner diameter of the outer tubular body and the outer diameter of the inner hypotube that can provide an exit/entrance when the inner hypotube's flared section is distally extended past the end of the outer hypotube. In certain embodiments, this may be accomplished with a non-circular cross-section. The distal end of the outer tubular body may also be flared with or without a gap to provide a lumen between the hypotube's outer diameter and the elongate member's inner diameter such as described above. In some embodiments, dimples may be provided on the outer tubular body to direct the bias the inner hypotube. The inner hypotube may also be bent or biased against the outer tubular body. Biasing against the outer tubular body may also provide blunting of the edges of the outer tubular body.

Figure 12A:
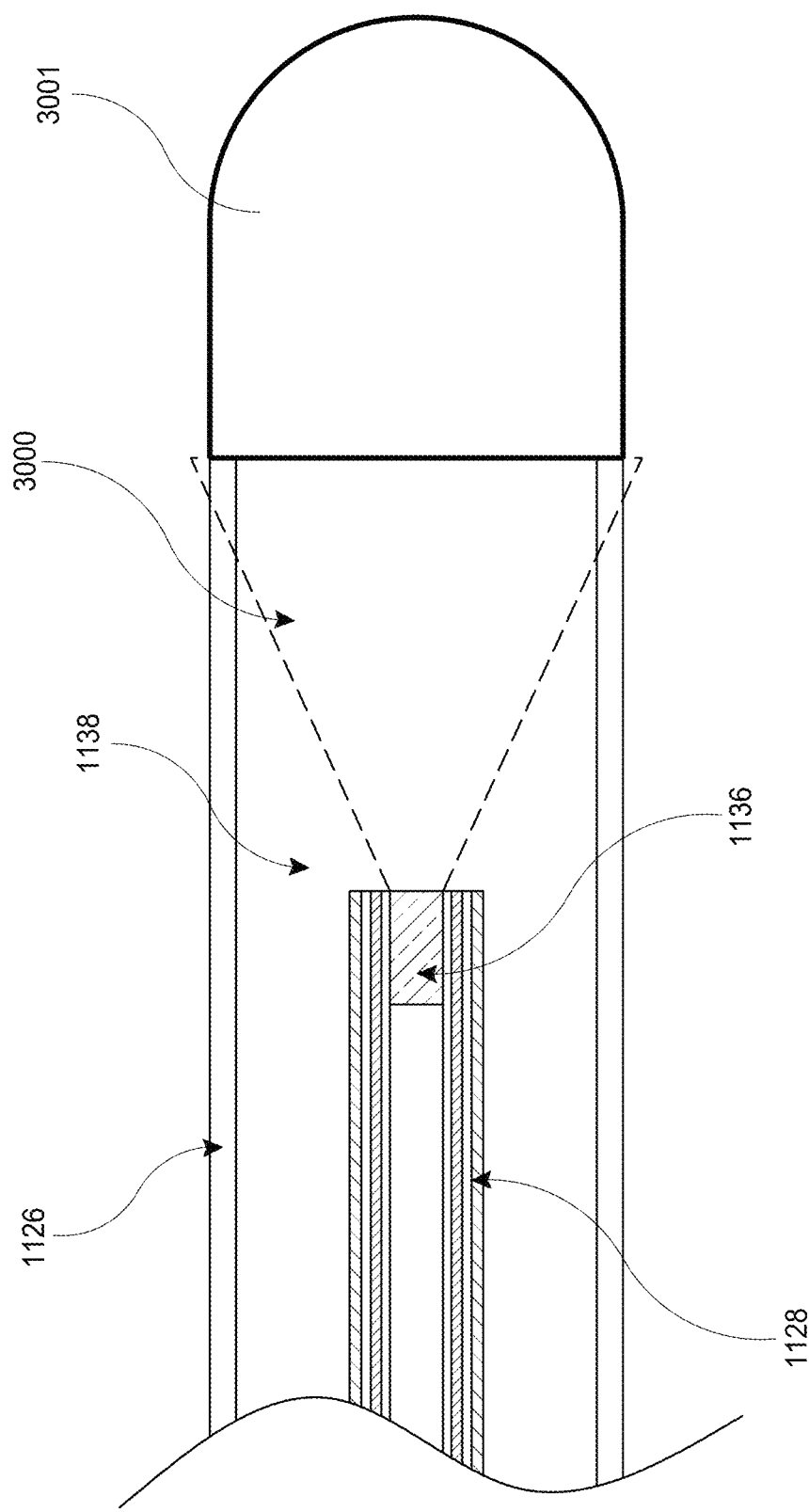

FIG. 12A depicts an embodiment of a clot evacuation device, similar to the clot evacuation devices depicted above in relation to FIGS. 1-3D. Here, the distal end or the elongate member incorporates an Optical Trocar concept, a transparent bulb that allows visualization through a clear and conically shaped distal end or window 3001 (also known as an obturator or introducer). The conically shaped distal end may be part of a larger optical trocar through which the clot evacuation device passes, or as described below may be a conically shaped distal end attached to the distal end of the clot evacuation device. In some embodiments, the distal end 3001 may be removably attached to a clot evacuation device, in which case the clot evacuation device can be inserted with the distal end 3001 attached to place an outer cannula, removed to detach the distal end 3001, and reinserted without the distal end 3001 to operate the clot evacuation device, as described elsewhere herein. In some embodiments, the distal end 3001 may be configured to open (e.g., like a petal or like jaws) to allow operation of the clot evacuation device through the opening, as described elsewhere herein. Such an arrangement with a transparent distal end 3001 provides visualization while the clot evacuation device is traversing the brain tissue to reach the clot. For example, a clear and conically shaped distal end 3001 may allow visualization of the transition from the white brain matter to the red clot to ensure that the clot evacuation device does not injure or tear brain matter while navigating through the brain. In embodiments involving an outer trocar, a second separate device could then be used for aspiration/visualization. For example, the distal end 3001 can be attached or integrated to a separate introducer device from the clot evacuation device. The introducer may be used to place an outer cannula or trocar, removed, and replaced by a separate clot evacuation device within the outer cannula or trocar for performing the clot evacuation procedure, as described elsewhere herein.

In certain embodiments, similar to the above concept, the visualization components of the integrated clot evacuation device may be integrated/bonded into the conical distal window of the transparent tip. In embodiments, the distal window may be configured to open like a petal and allow device components, such as the inner hypotube or outer tubular body to extend forward and/or retract. In some embodiments, as described above, the optical trocar may contain a separate clot evacuation device such as described above, but with only visualization components, for visualization during insertion, that is then removed from the clear trocar once the targeted site is reached. The trocar would then be removed from the cannula/portal, leaving the portal intact to the target site. Next, a second or the same integrated clot evacuation device (with integrated suction) would then be inserted down the inner diameter of the cannula for aspiration/visualization of the clot. The trocar-with-visualization may also incorporate additional features such as: illumination fibers (visible light or UV or IR or some other useful wavelengths), an ultrasonic transducer (to "see" through the tissue), a glucose sensor, or some other kind of sensor that would have clinical benefit during the traversing tissue step.

In certain embodiments, visualization may be incorporated into the cross-section of a cannula/portal with optional enhancements such as those described above (extra illumination, extra sensors, etc.). The distal end of the cannula may be flat or angled. If angled, the bevel tipped "point" of the cannula could hold the visualization elements and provide better visualization during the traversing step as it would be the most distal element. In further embodiments, a second separate aspiration device could be used for removing the clot or alternatively an integrated aspiration/visualization device could be used providing two different views of the clot site.

In certain embodiments, a navigation probe configured to be inserted within the conically-shaped transparent distal end. A locking member may also be provided operatively retain the navigation probe within the obturator. Further details regarding a navigation probe may be found in U.S. Pat. Pub. 2014/0171873, hereby incorporated by reference in its entirety.

As is known in the art, in embodiments, there are a number of variables that play in the selection of the angle that defines the taper of tip portion of an obturator. These variables include the size of an outer diameter D1 of obturator, the desired length that distal tip portion extends from body portion, and the desired offset for distal tip. However, to insure that the distal tip is determinable regardless of which size diameter D1 of obturator is used, the taper angle may be selectively adjusted. For embodiments that utilize a navigation probe that positions a distal end at a set position within the obturator to maintain an identical offset length between the distal end of navigation probe and distal tip in different diameter D1 sized obturators, the taper angle will need to be increased, as diameter D1 increases to achieve atraumatic dilation, as well as a determinable distal tip location.

In embodiments, the transparent obturator distal tip is configured to be radiused such that tip member is rounded, and neither blunt, nor sharp. More specifically, the tip may be configured so as not to have any flat portions which during insertion can stretch or even tear the delicate tissues such as the vessels, fiber tracts and fascicles found in the brain. Further, because the tip is closed, damage of such delicate tissues and fascicles are also avoided. In embodiments, the tip is configured with a 0.5 mm radius. The configuration of the tip is designed to gently displace and move the tissue into which it is inserted; i.e., atraumatically dilate the tissue to allow for introduction in to an intra-fascilar and para-fascilar manner, as opposed to cutting tissue as the clot evacuation device is inserted into the tissue.

FIG. 12B depicts an embodiment of the distal end 302 of the clot evacuation device 300, with a window 304 positioned within the access device or trocar to allow for visualization while the clot evacuation device 300 is navigating through the brain or other tissues. The clear window 304 may allow color differentiation during insertion, such as between red blood clots and white brain matter. The inner hypotube 306 (e.g., visualization device comprising optical elements) may be removed from the introducer once the target is reached. In some embodiments, the distal end 302 may be removably attached to a clot evacuation device, in which case the clot evacuation device can be inserted with the distal end 302 attached to place an outer cannula, removed to detach the distal end 302, and reinserted without the distal end 302 to operate the clot evacuation device, as described elsewhere herein. In some embodiments, the distal end 302 may be configured to open (e.g., like a petal or like jaws) to allow operation of the clot evacuation device through the opening, as described elsewhere herein. In other embodiments, the distal end 302 is attached or integrated to a separate introducer device, which may be used to place an outer cannula or trocar, removed, and replaced by a separate clot evacuation device within the outer cannula or troar for performing the clot evacuation procedure, as described elsewhere herein. FIG. 12C depicts rotation of the inner hypotube or optical elements such as is described elsewhere in the specification. The circumference of the inner hyoptube 306 may comprise notches which can be turned by a motor or actuation element (e.g., gear 309) in the proximal end of the device. Alternatively, the proximal end of the inner hypotube 306 may comprise a lever 307, which can be manually turned to rotate the inner hypotube 306. FIG. 12D depicts an example of a cross section of the clot evacuation device comprising an inner hypotube 306 positioned along an inner surface of the outer tubular body.

Figure 13:
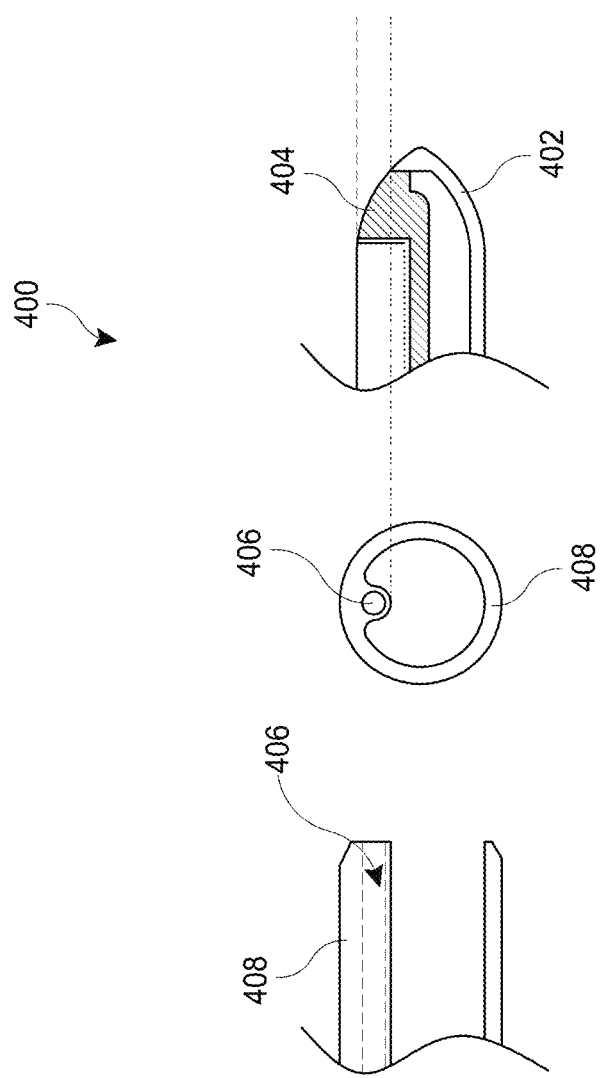
FIG. 13 illustrates embodiments of the distal tip of a clot evacuation device with a conically-shaped transparent distal portion.

FIG. 13 schematically depicts an embodiment of the distal tip of a clot evacuation device 400, similar to the devices depicted above. In embodiments as shown in FIG. 13, a conically shaped transparent distal end 402 (or obturator) may extend beyond the distal end of the cannula or outer tubular body 408 or retract within the outer tubular body 408. In embodiments, the visualization elements similar to the inner hypotube described elsewhere in the specification, are positioned in a visualization channel 406 against the outer tubular body 408 to allow for visualization beyond the conically-shaped transparent distal end 402. The lumen of the outer tubular body 408 can comprise the main clot evacuation lumen as described elsewhere herein. The conically-shaped distal end 402 may comprise a transparent window portion or insert 404 that is movable with respect to the geometry of the distal end 402. The window portion 404 may be moved (e.g., rotated) between an inward position (facing right in FIG. 13, not shown) and an outward position (facing left in FIG. 13, shown). The outer diameter of the distal end 402 may be greater when the window portion 404 is positioned in the outward position than when the window portion 404 is positioned in the inward position. In use, in one embodiment a separate obturator having the distal end 402 may be slidably inserted through the lumen of the outer tubular body 408 (e.g., the evacuation lumen) of a cannula, with the window portion 404 positioned in the inward position. When in the inward position, the distal end 402 may comprise an outer circumference that mates with the inner circumference of the outer tubular body 408, including an inwardly protruding visualization channel 406, such that the distal end 402, including window portion 404, may be together slidably inserted through the lumen.

Once the distal end 402 is inserted to a length such that a proximal ledge of the moveable window portion 404 distally surpasses the distal end of the visualization channel 406, the moveable window portion 404 can be moved to the outward position. In some embodiments, the distal end 402 may not be insertable into the outer tubular body 408 with the window portion 404 in the outward position (i.e. the distal end 402 with moveable window 404 may not have sufficient clearance with respect to the visualization channel 406). When the window portion 404 is positioned in the outward position, the window portion 404 together with the rest of the distal end 402 may form a conically-shaped tip that closes off the open end of the outer tubular body 408, including the visualization channel 406. The window portion 404, when positioned in the outward position, may cover or shield the visualization channel 406, such that visualization elements within the visualization channel 406 may operate through a transparent portion of the moveable window portion 404 to provide visualization. The moveable window portion 404 may be returned to the inward position for removing the distal end 402 from the outer tubular body 408. The distal end 402 with window portion 404 may be removed by sliding the distal end 404 proximally through the lumen of the outer tubular body 408. Once removed, evacuation or other operations may be performed through the lumen. In some embodiments, the moveable window portion 404 may be a separate component from the distal end 402. In other embodiments, the moveable window portion 404 may be attached to the distal end 402 in a manner that allows the moveable window portion 404 to move between inward and outward positions. The leading edges of the outer tubular body 408 may also be tapered so as to allow the clot evacuation device 400 to pass through tissue.

Figure 14:
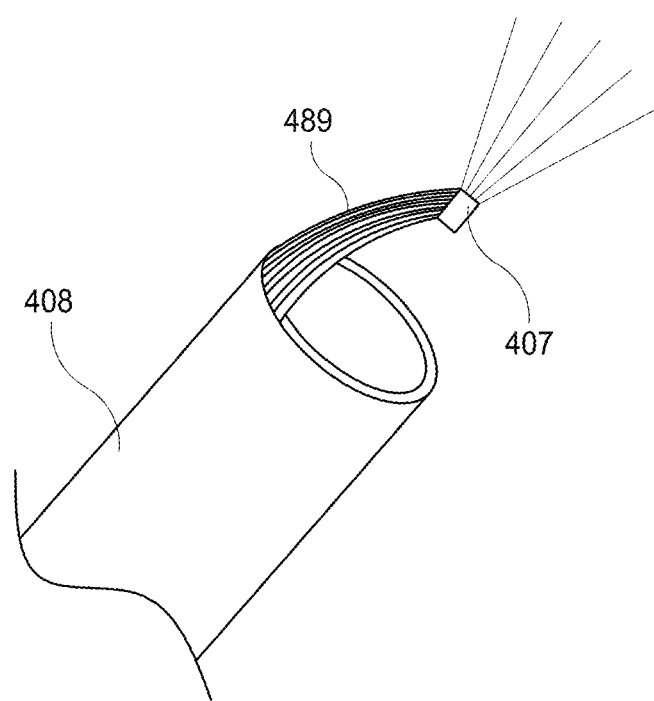
FIG. 14 illustrates an embodiment of a clot evacuation device.

FIGS. 14-22 depict further views and descriptions of embodiments of the clot evacuation device. FIG. 14 depicts an embodiment of the clot evacuation device that allows visualization during insertion and suction steps, with a camera 407 or optics positioned at or near the central axis of an elongate outer tubular body 408. The camera 407 may be positioned on a distal structure 409 (e.g. a scoop structure) that extends distally from a distal opening in the outer tubular body 408, this structure curving radially inward toward the central axis of the outer tubular body 408. The edge of this structure 409 may form or be used as a scoop for clot removal during rotation. The distal structure 409 may be integrally formed with the elongate outer tubular body 408, or may be separately attached.

Figure 15:
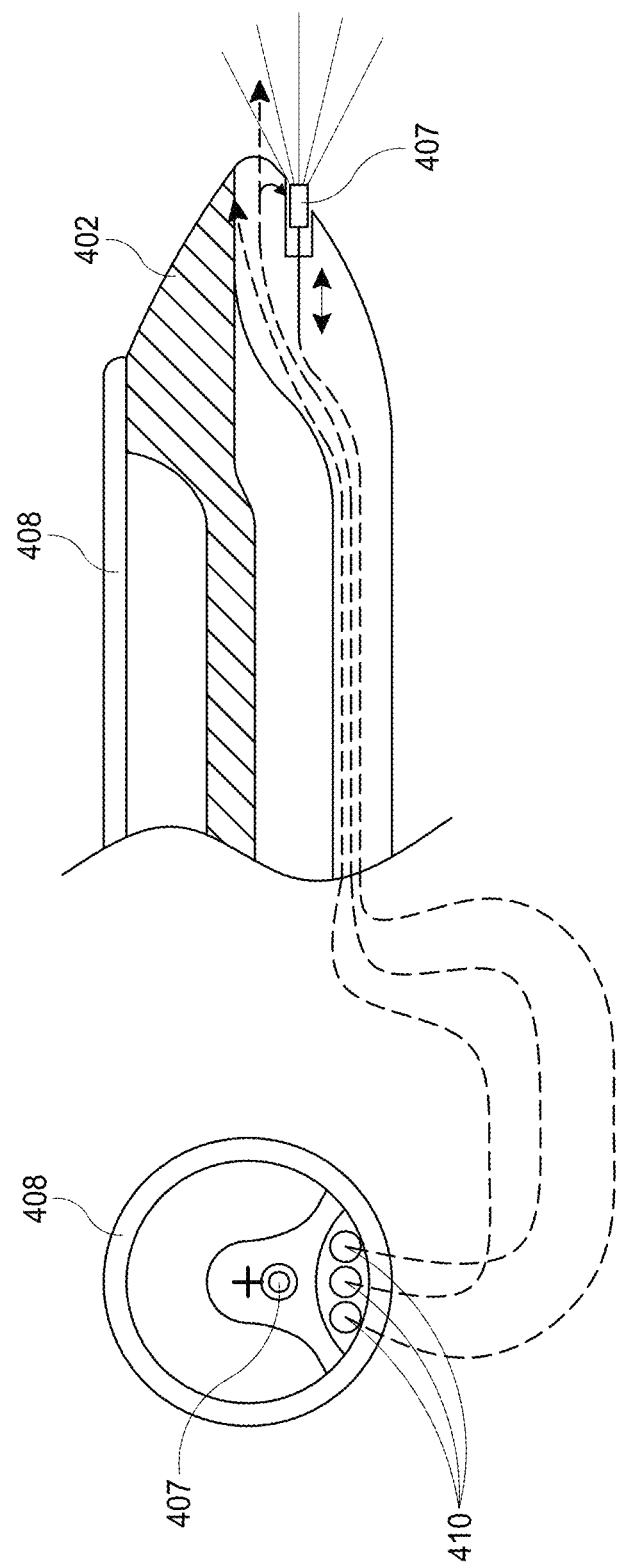
FIG. 15 illustrates an embodiment of a clot evacuation device with an insertable obturator.

FIG. 15 depicts partial cross-sectional views of a device similar to that of FIG. 14, showing the camera 407 positioned at or near the central axis (schematically indicated as "+") of the outer tubular body 408. In FIG. 15, the camera 407 is not located on the central axis of the outer tubular body 408, but is slightly offset. An obturator 402 may be used to close the distal end of the device during insertion. The camera 407 may be able to translate axially (schematically depicted by the double arrow) for tunnel visualization or to an inner cleaning position, described further below. One or more lumens 410 may be provided within or alongside the outer tubular body 408 to provide illumination, irrigation, and optics clearing fluid for the camera 407 (as schematically depicted by the arrows).

Figure 16:
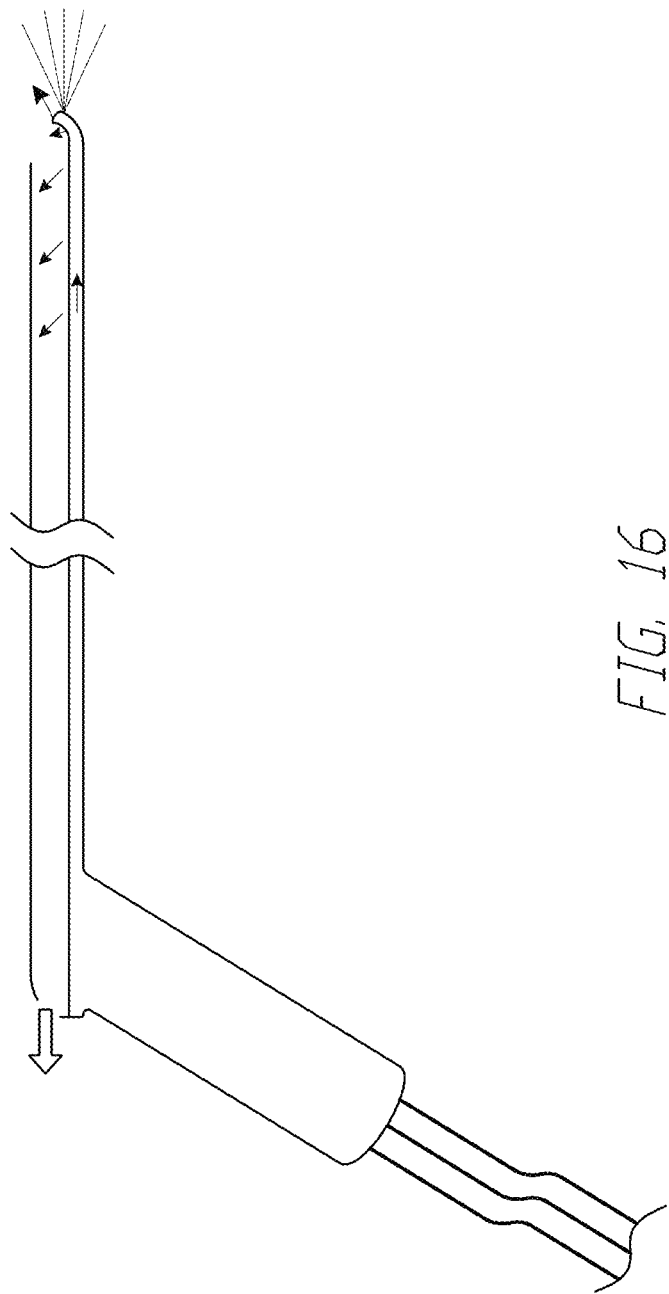
FIG. 16 illustrates an embodiment of a clot evacuation device.

FIG. 16 schematically depicts an embodiment of the clot evacuation device with a bayonneted handle that may allow for better ergonomics. An exterior portion of the device may have length markings to show depth into the anatomy. An obturator such as shown in FIG. 15 can be removed from a proximal portion of the handle, with a cover, plug, or seal to cover a proximal opening. Suction tubing can be attached to a proximal portion of the handle to provide a linear or "straight shot" removal pathway. The proximal end may include conduits for irrigation, suction, and/or electrical/data connections. Irrigation is schematically depicted by arrows. Depending on the overall size of the device, the handle could be used to form a portal or could be used within a larger portal in conjunction with a microscope and/or other instruments.

FIG. 17 illustrates variations of the distal end of the device compared to FIG. 14, showing different variations in the distal structure 409 that positions the camera at or near the central axis.

Figure 18:
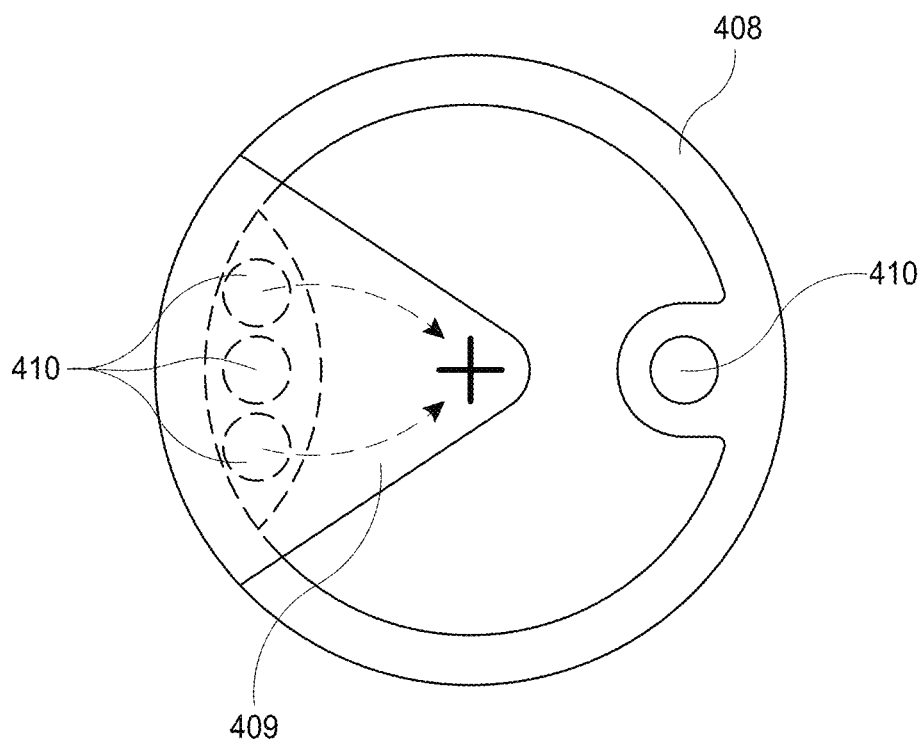
FIG. 18 illustrates an embodiment of a clot evacuation device.

FIG. 18 depicts an embodiment with multiple lumens 410 in the side wall of the elongate outer tubular body 408, with the camera positioned at the central axis. For example, as illustrated three lumens 410 may be provided on one side of the elongate tubular body, to accommodate a first sensor (cable and fiber), a second sensor (position 2) and irrigation. A fourth lumen 410 may be positioned opposite the three lumens, which may be utilized for a second sensor (position 1).

Figure 19:
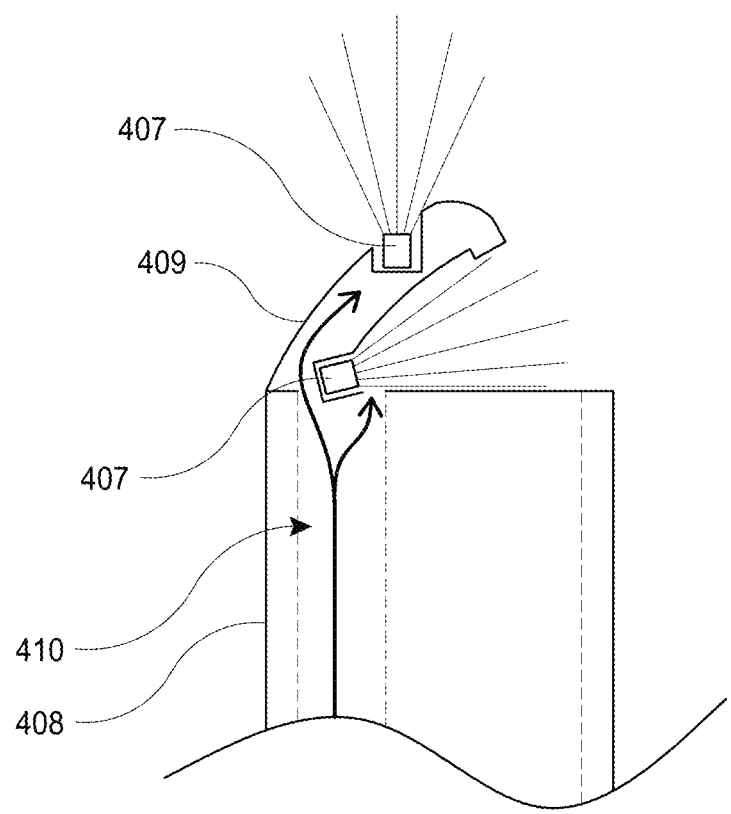
FIG. 19 illustrates an embodiment of a clot evacuation device.

FIG. 19 shows an additional embodiment where a second camera 407 may be located within an inner diameter of the elongate outer tubular body 408. For example, a first camera 407 as described above may be positioned on a distal structure 409 at or near the central axis of the elongate tubular body 408 to provide visualization of objects in front of the distal tip. A second camera 407 located within the inner diameter, or at least proximal to the distal structure 409, may provide visualization of the clot around the distal tip and side walls of the device. The clot evacuation device can comprise one or more lumens 410 for providing irrigation to clean the cameras 407 (one lumen 410 may split into two or there may be two separate lumens 410)

Figure 20:
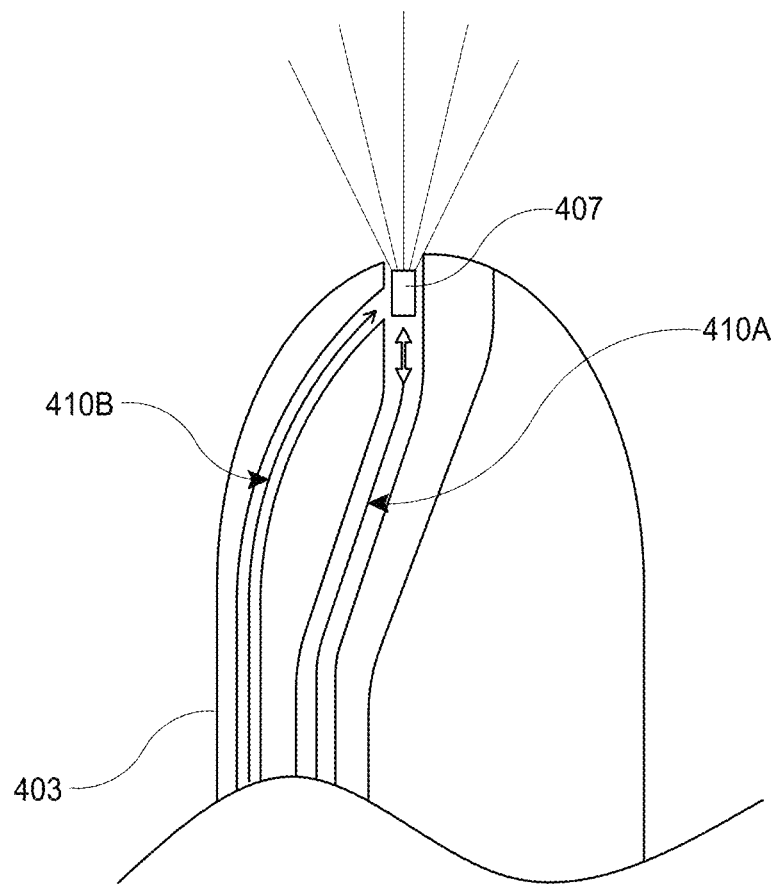
FIG. 20 illustrates an embodiment of a clot evacuation device.

FIG. 20 depicts an embodiment of a clot evacuation device with multiple channels 410 for visualization elements, clot evacuation, and lens irrigation for cleaning. For example, a first channel 410A may be provided to house the optics or camera 407 to provide visualization in front of the device. This first channel 410A may encroach onto the main clot evacuation lumen (e.g. opening to a side of the front portion of the clot evacuation device, such as the front right side in FIG. 20) in order to more centrally position the optics. A second channel 410B may be provided for irrigation to provide cleaning of the optics. For example, the second channel 410B may be provided with a distal jet or nozzle to direct fluid against the optics. The optics (e.g. camera 407) may translate within the first channel 410A to maximize the effect of the jet or nozzle. A third channel (not shown) may be provided for clot irrigation. The third irrigation channel may have a larger diameter than the second cleaning channel. The third channel may also have jets or nozzles to help dislodge a clot (e.g., by water dissection). For example, the third channel may direct fluid along the edges of the elongate outer tubular body 408, and/or along the edges of the distal "scoop" structure 409 described above, to aid in the scooping function. The third channel may also direct fluid radially inward or proximally to dislodge clots or prevent clots from lodging within the device.

Figure 21:
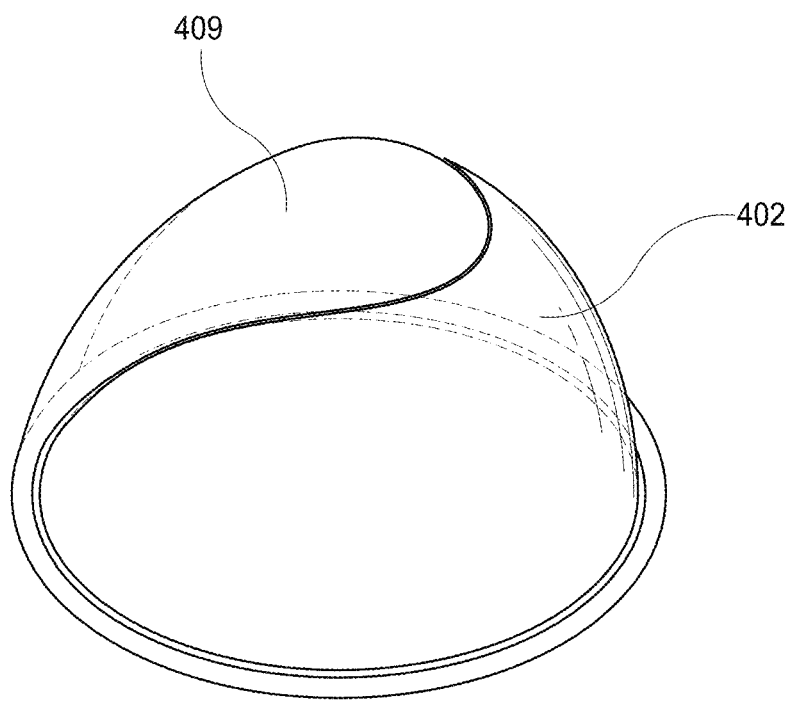
FIG. 21 illustrates the distal end of an obturator.

FIG. 21 shows an obturator 402 shape that may be utilized to fill the open space around the modified distal structures 409 described above. FIG. 21 illustrates the opening at the distal end of an outer tubular body 408, with a distal structure 409 extending beyond the distal opening. The obturator 402 may have a shape that matches the shape of the distal structure 409, to provide a generally continuous, closed surface at the distal end of the combined structure. Such an obturator 402 may be removed from a proximal end of the elongate outer tubular body 408 when clot evacuation is to be performed.

Figure 22:
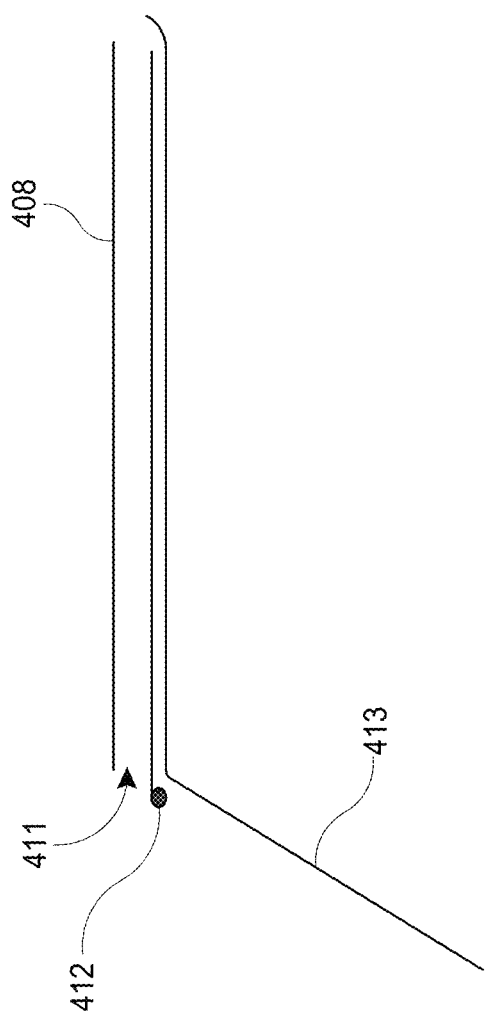
FIG. 22 illustrates an embodiment of a clot evacuation device.

FIG. 22 schematically depicts an embodiment of the clot evacuation device without a handle (i.e. a portal). The clot evacuation device may comprise a working channel 411 and visualization and/or illumination elements. The proximal end may comprise an LED 412 for transmitting light to the distal end of the device. The proximal end can be configured with minimal bulk, which may allow better instrument manipulation in the working channel of the portal by moving items away from the cranial access site. For example, a loose sensor wire 413 may continue past the proximal end of the portal, and the sensor may be positioned outside of the outer tubular body 408 of the portal.

Figure 23:
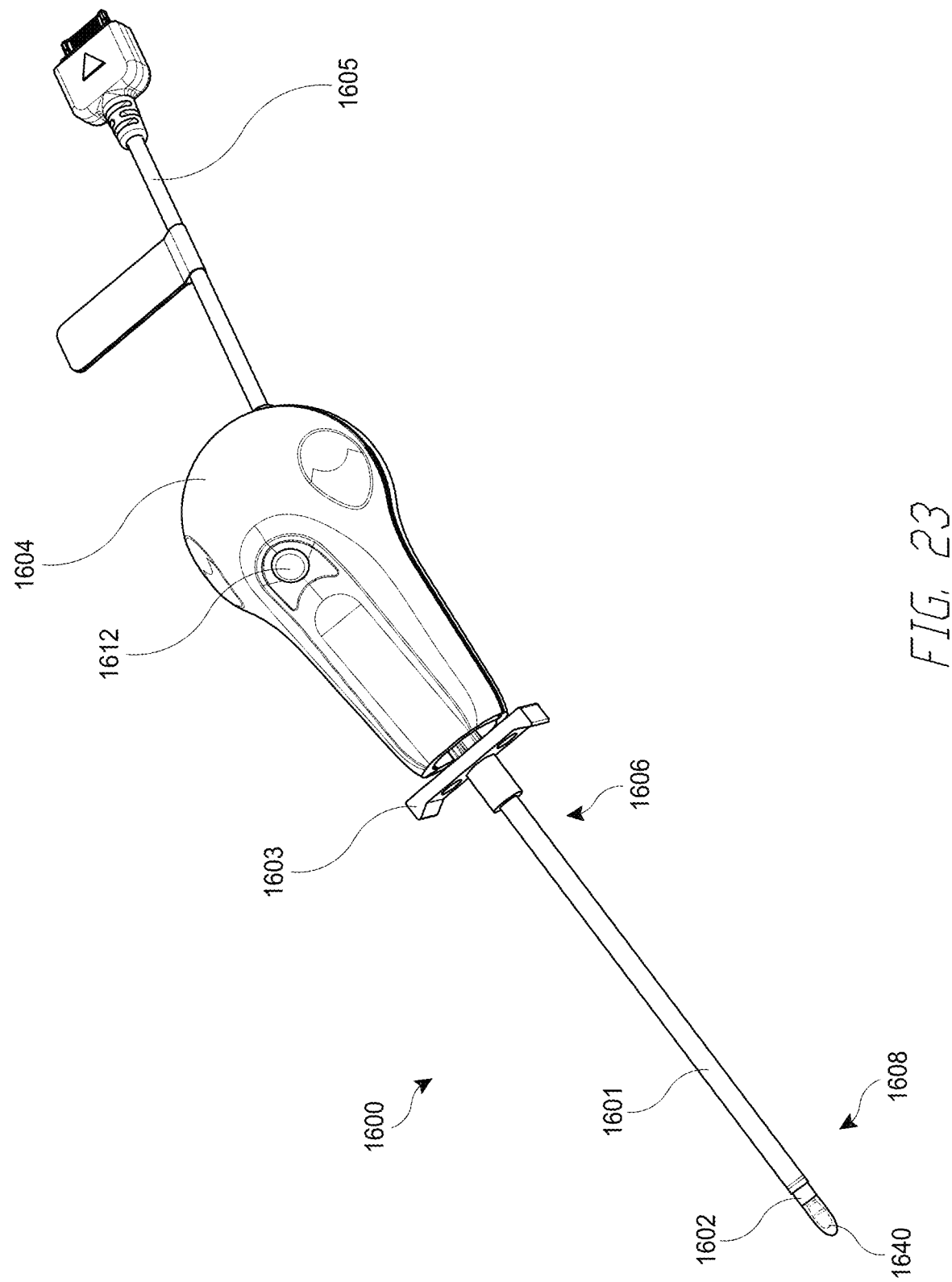
FIG. 23 shows a perspective view of an optical introducer.

Systems and Methods Utilizing an Optical Introducer and a Separate Clot Evacuation Device FIG. 23 depicts an example of an optical introducer 1600, which may have features similar to those previously described, including those related to the Optical Trocar concept, for visualization during insertion into bodily tissue, such as brain tissue. The terms "obturator" and "introducer" may be used interchangeably herein. The optical introducer 1600 may be inserted simultaneously with an outer sheath 1601. In some embodiments, an outer sheath may be inserted over the optical introducer 1600 after it has been inserted into the body. The optical introducer 1600 creates a pathway to the target tissue, which the outer sheath 1601 may maintain once the optical introducer is removed from the body. The outer sheath 1601 may or may not be a peel-away sheath. If peel-away, the outer sheath 1601 may comprise tabs 1603 for bisecting the outer sheath 1601 along its circumference. The optical introducer 1600 comprises an elongated body 1602 having a proximal end 1606 and a distal end 1608. The distal end 1608 may comprise an atraumatic tip 1640, which may be shaped to be relatively rounded, semi-spherical, conical, and/or tapered to help separate tissue as the optical introducer traverses tissue and to avoid cutting, tearing, or coring the tissue. Other atraumatic shapes may be suitable as well. The atraumatic tip 1640 may be entirely or partially transparent to the visible light spectrum or to select wavelengths of light such that direct visualization may be achieved through the tip. In some embodiments the entire atraumatic tip 1640 is constructed from a transparent material, such as a transparent plastic, and may be formed by injection molding. In other embodiments, the atraumatic tip 1640 may be opaque but may comprise a transparent or partially transparent window positioned to allow visualization through the window. The outer sheath 1601 may be configured such that it cooperates with the atraumatic tip 1640 to form an atraumatic distal end of the optical introducer 1600. For instance, the distal edge of the outer sheath 1601 may be tapered, rounded, and/or beveled, so as not to provide a sharp edge that might snag tissue sliding over the atraumatic tip 1640.

The proximal end 1606 may be coupled to a handpiece 1604 by which the operator may use hold and/or control the optical introducer 1600. The shape of the handpiece 1604 may be similar to the shapes of other handpieces described herein. For example, the handpiece 1604 may comprise a generally "clamshell" shape and may include a clamshell top and clamshell bottom connected at a seam. Some embodiments may comprise a clamshell left side and clam shell right side connected at a seam. The handpiece 1604 may include a cable 1605, such as a USB cable, extending from the handpiece 1604 for transferring data and/or for powering the device. In some embodiments, the optical introducer 1600 may comprise wireless capabilities. The optical introducer 1600 may be controllable from an operatively coupled external controller or processor, which may include software for interfacing with the optical introducer. The handpiece 1604 may comprise one or more buttons 1612 for controlling the functionality of the optical introducer 1600. For example, the handpiece 1600 may include a camera button, which may activate the system to collect and/or store a still or moving image or a power button for powering off and on the device.

Figure 24A:
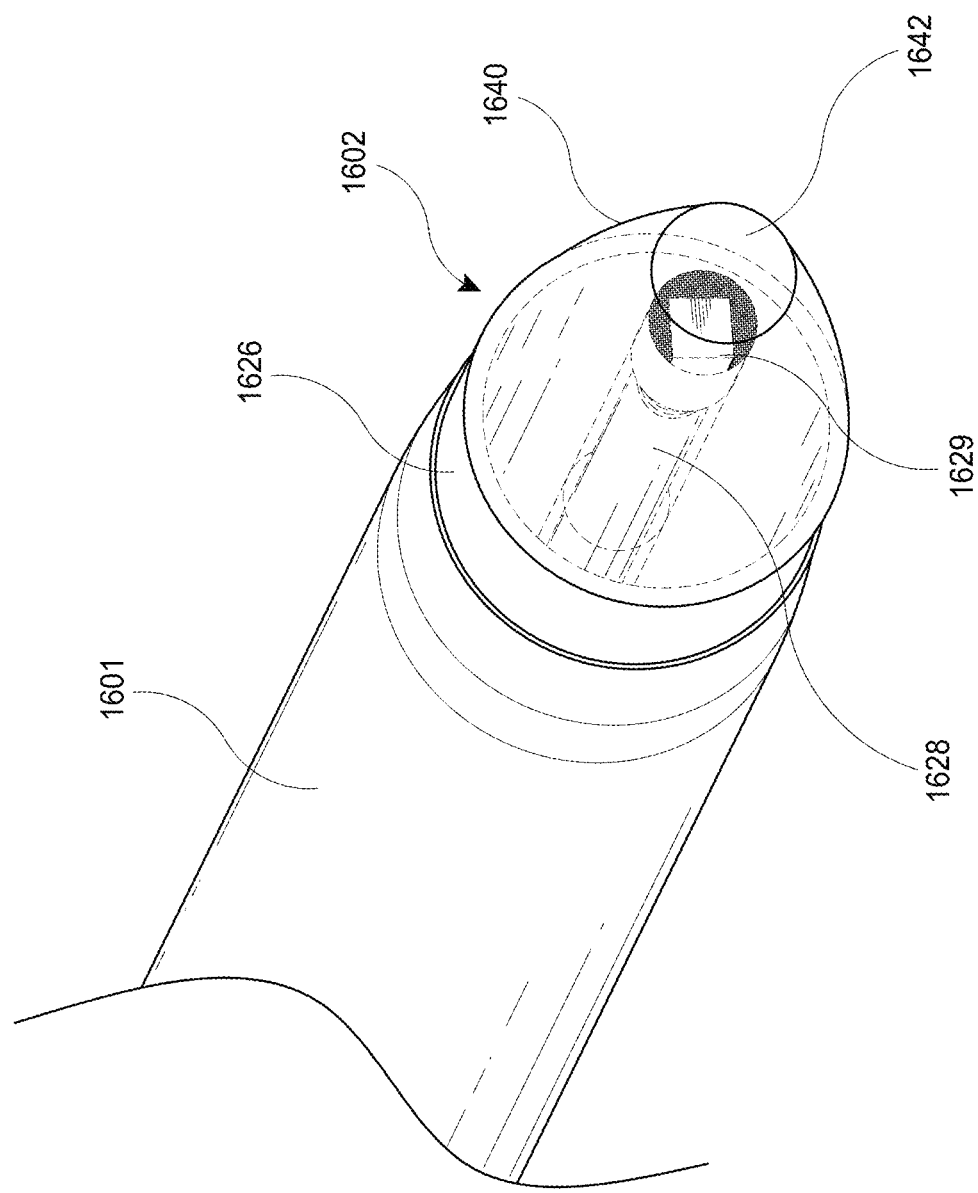

FIG. 24A shows a view of the distal end 1608 of the elongate body 1602 of an optical introducer 1600. The elongate body 1602 may comprise an outer tubular body 1626 configured to removably receive a visualization element 1628 or a visualization element 1628 may be integrally affixed within the elongate body. The visualization element 1628 may comprise a hypotube, as described elsewhere herein, and may include an image guide for transmitting light down the hypotube to an image sensor, such as a camera, and/or an image sensor 1629 positioned at or near the distal end of the hypotube. The visualization element 1628 may include illumination elements within the hypotube, such as fiber optics or LEDs, as described elsewhere herein, or illumination elements may be provided elsewhere within, adjacent to, or integrated with the outer tubular body 1626.

The visualization element 1628 may be positioned centrally within the elongate body 1602 along its longitudinal axis, as shown in FIG. 24A, or may be positioned off-center. The distal end of the visualization element 1628 may extend into the atraumatic tip 1640. The interior of the atraumatic tip 1640 may be hollow or may be solid with a channel defined within for receiving the visualization element 1628, as shown in FIG. 24A. The distal-most end of the atraumatic tip 1640 may end in a rounded tip or may include a flattened surface 1642 normal to the longitudinal axis of the elongate body 1602 and aligned with the distal end of the visualization element 1628. The flattened surface 1642 may provide for better quality imaging through the atraumatic tip 1640.

In some embodiments, the distal end of the visualization element 1628 may be deflected at an angle from the longitudinal axis and/or may be enabled with a wide-field view (e.g., 120 degrees), such as by a lens or prism. The direction of view of the visualization element may be centered, for example, 0 degrees, 3 degrees, 6 degrees, 12 degrees, 15 degrees, 20 degrees, 30 degrees, 45 degrees, or more than 45 degrees off the longitudinal axis of the elongate member 1602. The visualization element 1628 may achieve forward and side views relative to the longitudinal axis. In some embodiments where the direction of the view is off-center from the longitudinal axis, the field of view may be effectively expanded by rotating the visualization element 1628, the elongate body 1602, or the entire optical introducer 1600 by 360 degrees or less, as described elsewhere herein. In some embodiments, the depth of the field of view may be between about 5 mm and 35 mm.

Portions or the entirety of the outer sheath 1601 may be transparent or partially transparent, similar to the atraumatic tip 1640, so that the visualization element 1628 may visualize through the side of the outer sheath 1601 when the atraumatic tip 1640 is disposed partially or entirely within outer sheath 1601 and/or when side viewing is enabled by the visualization element 1628. Similarly, portions or the entirety of the outer tubular body 1626 may be transparent or partially transparent.

The optical introducer 1600 may be used according to any suitable method. By way of example, the optical introducer 1600 may be inserted through outer sheath 1601, such that at least the atraumatic tip 1640 extends beyond the distal end of the outer sheath 1601, and then inserted into the brain or other bodily tissue. The optical introducer 1600 may or may not pass through an access device and/or a trocar device, such as those described elsewhere herein. The optical introducer 1600 may comprise or may be operatively coupled to a navigation system, as described elsewhere herein, to assist in guiding the optical introducer down an appropriate path within the brain or other bodily tissue. The user may use the visualization element 1628 to visualize tissue positioned distally and/or along the sides of the distal end of the elongate member 1602 as the user inserts the optical introducer 1600 through the tissue. At any point in the procedure, the user may partially retract the optical introducer 1600 relative to the distal end of the outer sheath 1601, such that the visualization element 1628 is further separated from the bodily tissue disposed around the distal end of the outer sheath and viewed through a "tunnel." Such "tunnel vision" may advantageously allow the user to better focus on the tissue distal to the visualization element 1628. The images may be displayed in real time on a separate display device and the optical introducer 1600 may include functionality for capturing and saving still images. The optical introducer 1600 may be especially useful for allowing the user to detect the transition between white brain matter and the red blood clot of an intracranial hemorrhage (ICH), thus assisting the user in placing the outer sheath 1601 into proper position for subsequent clot evacuation procedures. Once the optical introducer 1600, and hence, the outer sheath 1601 are in proper position, the user may remove the optical introducer from the body and the outer sheath, leaving the outer sheath in place. Subsequently, the user may insert a separate surgical device, such as the clot evacuation devices disclosed elsewhere herein (or alternatively multiple devices, such as suction, irrigation, an endoscope, cutting tools, etc.) through the outer sheath 1601 such that it may be positioned at the distal end of the outer sheath 1601 to operate on the blood clot or other bodily tissue.

Figure 24B:
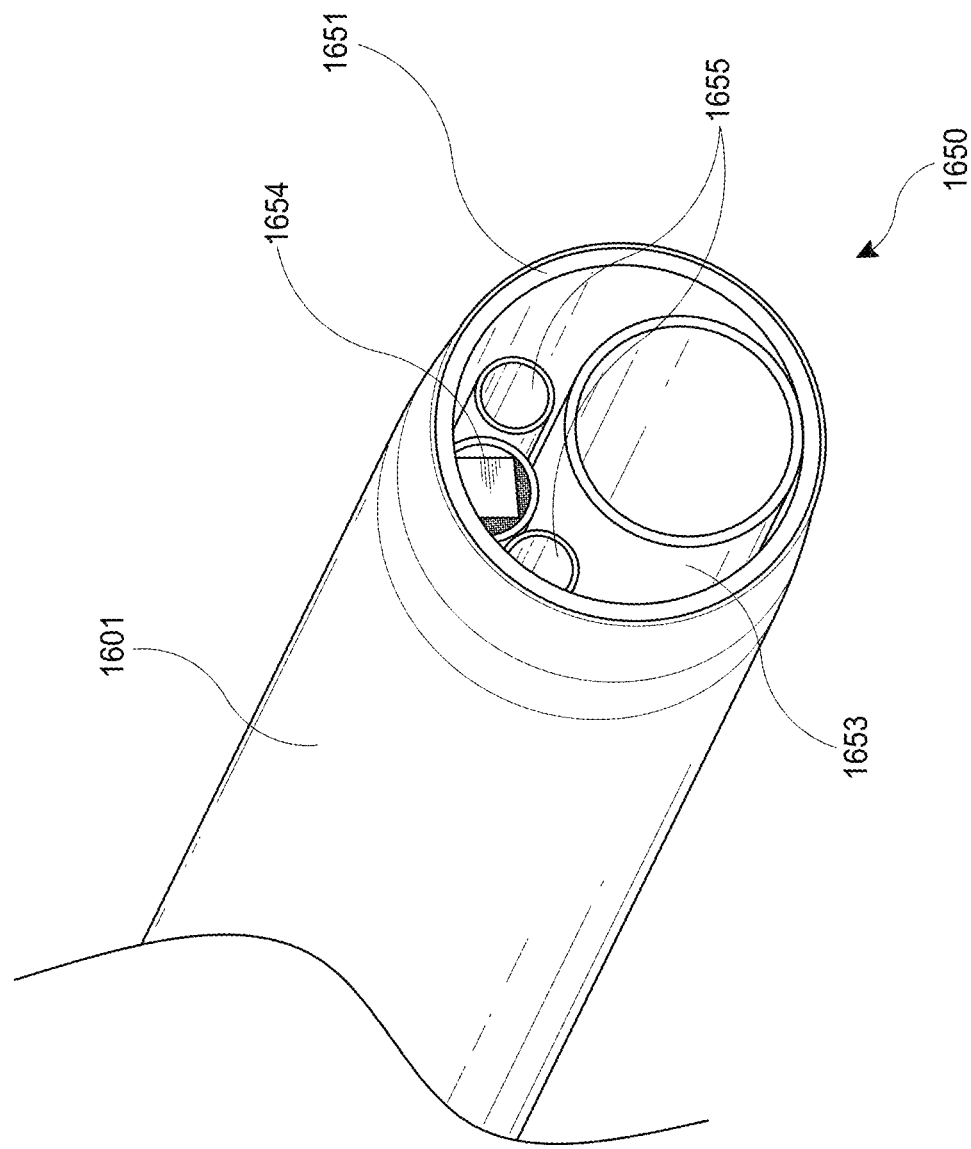
Figure 24C:
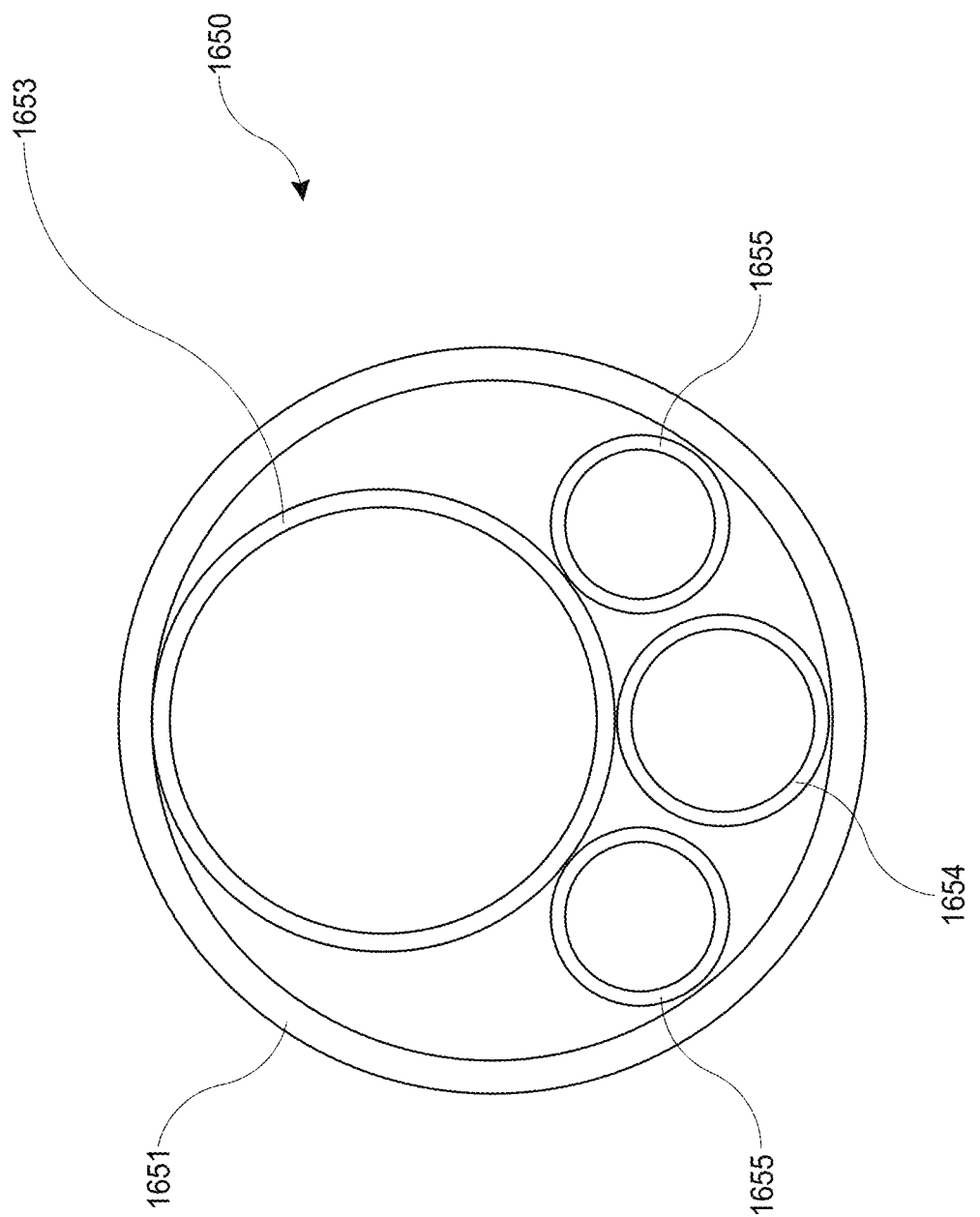

FIG. 24B shows an example of a clot evacuation device 1650 positioned within the outer sheath 1601. FIG. 24C schematically shows a cross-section of clot evacuation device 1650 along its elongate body. The clot evacuation device 1650 may, for example, comprise an outer tubular body 1651 (e.g., 6.05 mm OD, 5.5 mm ID) and a number of operational elements disposed within the outer tubular body, including an evacuation hypotube 1653 (e.g., 3.40-3.76 mm OD, 3.00-3.25 mm ID), for providing aspiration to remove the blood clot and irrigation fluids, a visualization element 1654 (e.g., 1.73 mm OD), which may be the same or similar to the visualization element 1628 disposed within the optical introducer 1600, and one or more irrigation hypotubes 1655 (e.g., 1.07-1.47 mm OD, 0.86 mm ID). The distal ends of the evacuation hypotube 1653, visualization element 1654, and irrigation hypotubes 1655 may be positioned at or near the distal end of the outer tubular body 1651 (e.g. the distal ends may be slightly displaced in a proximal direction within the outer tubular body 1651). In some embodiments, the operational elements, such as the evacuation hypotube 1653, may be axially translatable in a direction parallel to the longitudinal axis of the outer tubular body 1651, such that they may retract within (or further within) the outer tubular body and/or extend beyond the distal end of the outer tubular body. If more than one irrigation hypotube 1655 is provided, one may be configured to provide irrigation primarily to the blood clot and/or near the distal end of the evacuation hypotube 1653 to assist in removing the clot. A second irrigation hypotube 1655 may be configured to provide irrigation primarily to a lens of the visualization element 1654 for cleaning the lens and enabling better visualization, as described elsewhere herein. The distal ends of the irrigation hypotubes 1655 may accordingly be positioned at different positions along the length of the longitudinal axis and/or may be configured, such as by deflection of their distal ends, to direct irrigation fluid in different directions. Upon completion of the blood clot evacuation procedure, the clot evacuation device 1650 may be removed prior to, simultaneously with, or subsequent to removal of the outer sheath 1601. The outer sheath 1601 can optionally be removed prior to completion of the clot evacuation procedure and reinserted over the clot evacuation device 1650 if needed.

FIG. 24D depicts a perspective view of the proximal end of another embodiment of the clot evacuation device 1650 with a half piece of the handpiece housing removed. As shown, the handpiece 1664 may comprise a control 1618 for extending the clot evacuation hypotube 1653 in a distal direction relative to outer tubular body 1651 and other operation components. The control 1618 may be a rod affixed to the clot evacuation hypotube 1653 at its distal end, proximal to the hypotube's insertion into the outer tubular body 1651. The rod 1618 may be aligned axially with the clot evacuation hypotube 1653 such that linear translation of the rod causes linear translation of the clot evacuation hypotube 1653 in an axial direction parallel to the device's longitudinal axis. The clot evacuation hypotube 1653 may be extended beyond the distal end of the outer tubular body 1651. The control 1618 may be biased by a spring 1619 for maintaining the clot evacuation hypotube 1653 in a retracted position. The clot evacuation hypotube 1653 may be connected to a suction tube 1673 exiting the handpiece 1664 for providing suction to the evacuation hypotube 1653. The suction tube 1673 may be connected to a wall suction port, a syringe, or any other suitable means of providing suction. The handpiece 1664 may also comprise irrigation lines, including a clot irrigation line 1675 and lens irrigation line 1676, connected to the irrigation hypotubes 1655 and exiting the handpiece 1664 to join a supply means for providing irrigation. The handpiece 1664 may further comprise a visualization/illumination complex 1674 operatively connected to the visualization element 1654. The visualization complex 1674 may operate the same or similar to other embodiments as described elsewhere herein. The complex 1674 may be operatively coupled with a data port 1677, which can be connected to a data cable for transferring data between the clot evacuation device 1650 and an external processor, controller, and/or display.

Figure 24E:
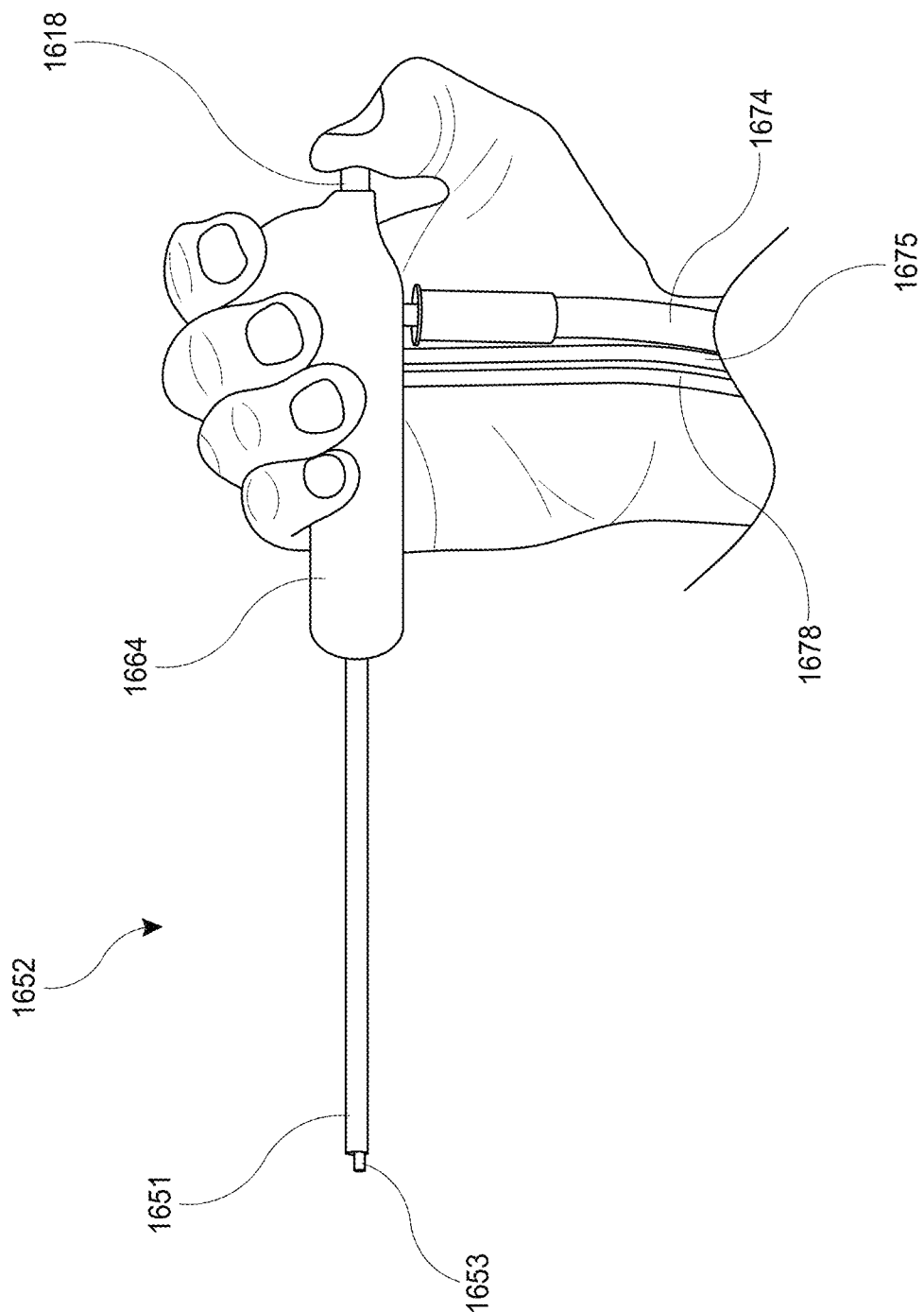

FIG. 24E shows a perspective view of an embodiment of the clot evacuation device 1600 being held in the hand of a user with the evacuation hypotube 1653 deployed in an extended position beyond the distal end of the outer tubular body 1651. A data cable 1678 may extend through an aperture to exit the device with the one or more irrigation lines 1675 and suction tube 1673.

Figure 24F:
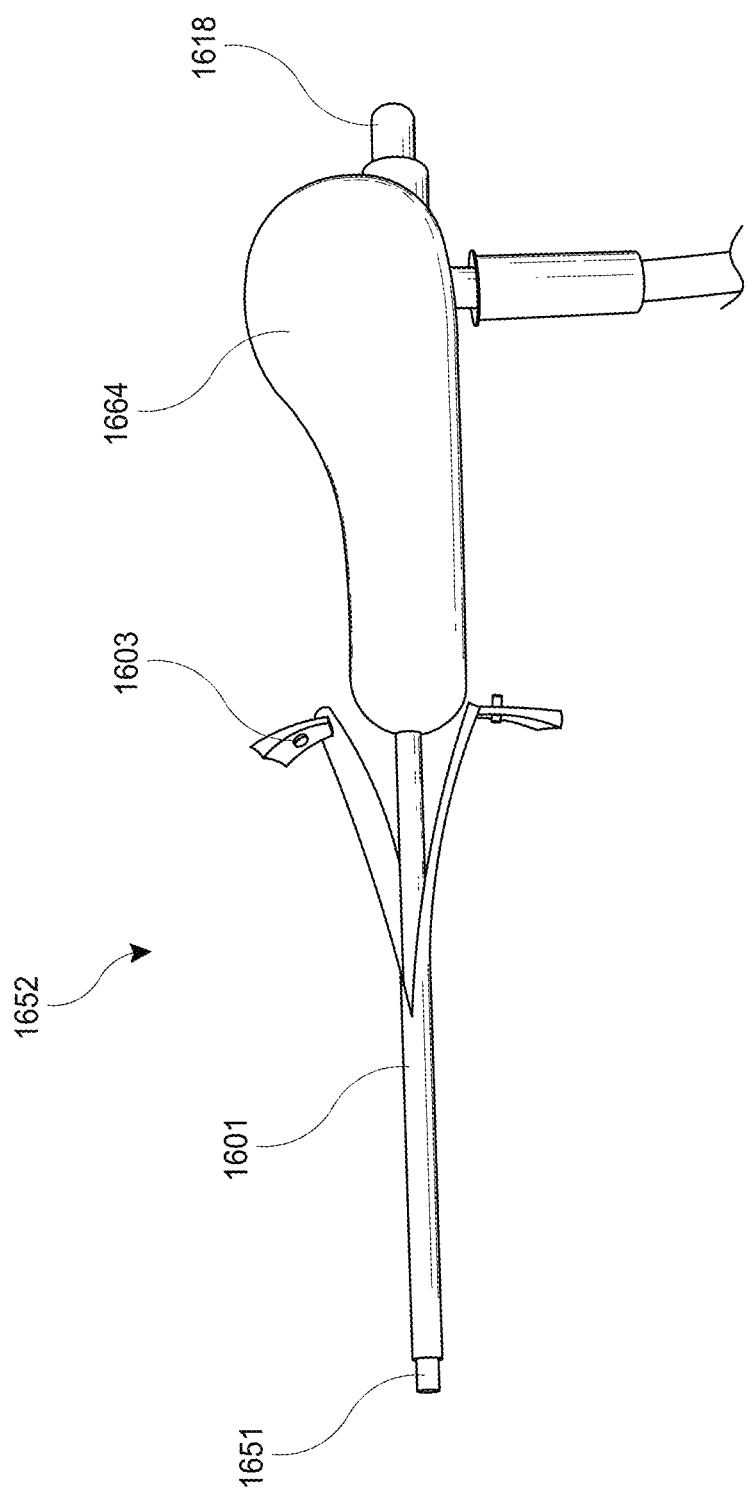

FIG. 24F shows a similar embodiment of the clot evacuation device 1650 with a partially peeled peel-away outer sheath 1601, comprising tabs 1603 at its proximal end, positioned over the elongate body 1652 of the clot evacuation device.

Figure 24G:
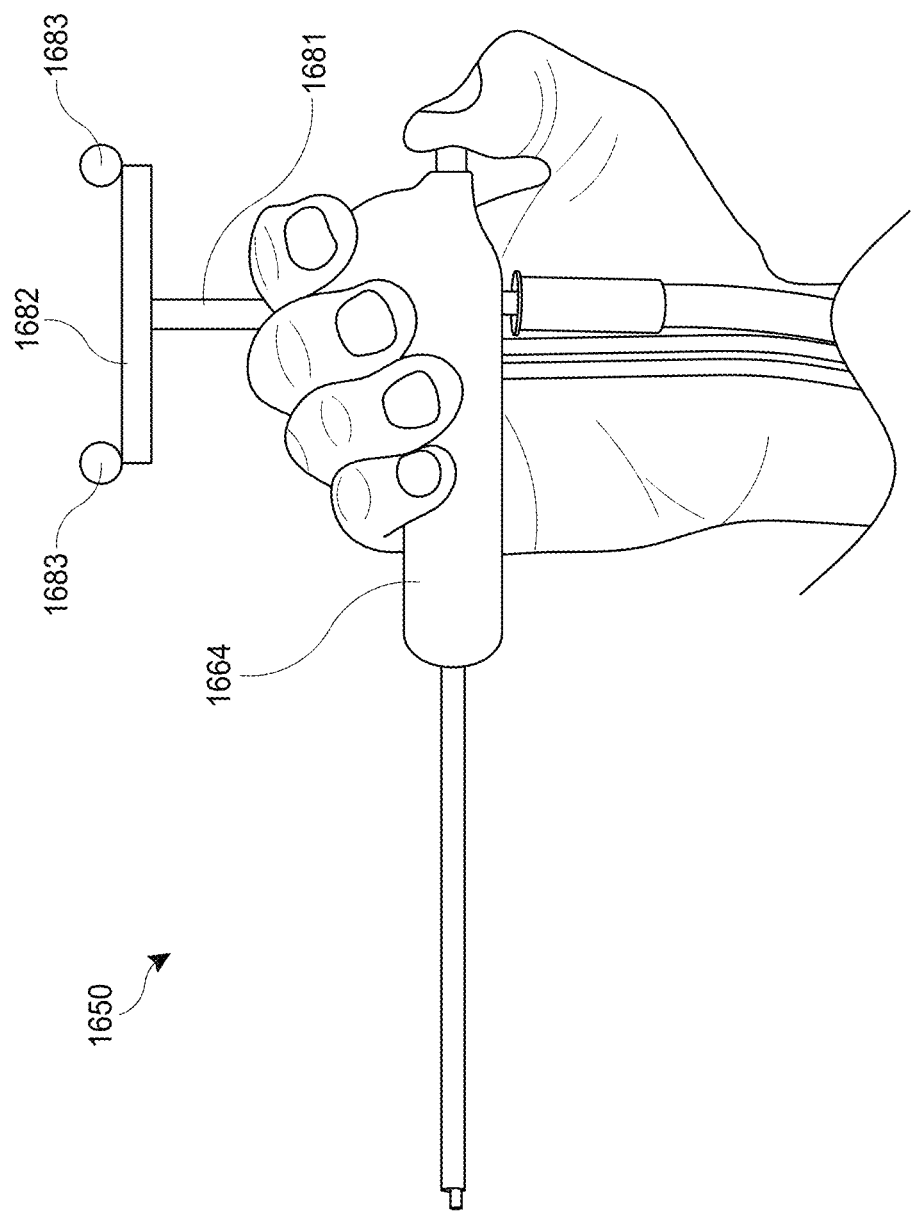

FIG. 24G schematically illustrates the embodiment of the clot evacuation device 1650 shown in FIG. 24E with components of a navigation system 1680 affixed to or integrated with the handpiece 1664. The navigation system may be the same or similar to other navigation systems described elsewhere herein. The navigation system may comprise a post 1681 extending from the handpiece 1664. The post 1681 may extend in any direction form the handpiece 1664 such that it remains outside the body and does not interfere with the insertion of the elongate body 1652 or operation of the clot evacuation device 1650. The post 1681 may be an integral part of the handpiece 1664 that is configured to mount one or more components of a separate navigation system. The post may be affixed to an array 1682 comprising one or more detection elements or reflectors 1683 (e.g., three reflectors) which are configured and spatially positioned to be tracked by a navigation imaging system. The known configuration between the reflectors 1683 and the clot evacuation device 1650 may allow the navigation system to determine the spatial positioning of the clot evacuation device, including the elongate body 1652, in relationship to the images obtained by the navigation system's imaging device. The reflectors 1683 may be optical reflectors which are optically detected by the imaging device of the navigation system.

Systems and Methods Utilizing a Clot Evacuation Device with a Removable Atraumatic Tip In another embodiment, a clot evacuation device, for example, one which is the same as or similar to the clot evacuation device 1650 shown in FIG. 24B, may be configured to be removably secured to an atraumatic tip component at its distal end, such that the clot evacuation device may additionally serve as an optical introducer. The atraumatic tip component may resemble the atraumatic configuration of tip 1640 shown in FIG. 23 or 24A but need not include any visualization elements integrated directly within the component. The atraumatic tip component may be entirely or at least partially transparent such that the visualization element of the clot evacuation device (e.g. visualization element 1654) could operate through the atraumatic tip component when the atraumatic tip component is secured to the clot evacuation device.

The atraumatic tip component may be secured to the distal end of the outer tubular body 1651 of the clot evacuation device 1650 by any suitable means such that it closes off and shields the open face of the outer tubular body and shields components disposed within the outer tubular body. The atraumatic tip component may be secured to the clot evacuation device by any suitable means. In some embodiments, the inner surface of the proximal end of the atraumatic tip component will comprise an elongate projection. The elongate projection may be configured to extend down and frictionally mate with the internal diameter of a working channel, such as that of the evacuation hypotube 1653, so that the atraumatic tip component is held in place at the distal end of the outer tubular member. In some embodiments, the atraumatic tip component may be configured with an annular portion and/or one or more protrusions at its proximal end that are shaped to fit within the internal diameter of the clot evacuation device's outer tubular body and secure the atraumatic tip component via an interference fit or a snap fit. In some embodiments, the inner diameter of the atraumatic tip component may be configured to mate with the outer diameter of the clot evacuation device's outer tubular body, such that the atraumatic tip component slides over the distal end of the outer tubular body. The atraumatic tip component may be removably secured to the clot evacuation device by a friction fit. The atraumatic tip component may be formed of plastic, such as a transparent plastic, and may be fabricated by injection molding.

The visualization element of the clot evacuation device may be located in the same or a different position within the outer tubular body as the visualization element 1654 of the clot evacuation device 1659 depicted in FIG. 24B or as the visualization element 1628 of the optical introducer 1600 depicted in FIG. 24A. The shape of the atraumatic tip component may or may not be altered to accommodate a visualization element positioned off center of the longitudinal axis of the outer tubular body, as depicted in clot evacuation device 1650 shown FIG. 24B. For example, a transparent portion of the atraumatic tip component which is disposed distally of the visualization element and through which the view is directed may be configured with a relatively steep taper, such that surface of the atraumatic tip component is closer to being perpendicular to the direction of the visualization element's view, similar to the flattened surface 1642 shown in FIG. 24A. The atraumatic tip component may be altered in other ways as well to optimize the view of the visualization element.

The atraumatic tip component may be secured to the distal end of the clot evacuation device prior to its insertion into the body. The clot evacuation device may then be inserted into the body with an outer sheath, such as outer sheath 1601, in the same manner as optical introducer 1600. Once the outer sheath is positioned, for example, adjacent a blood clot, the clot evacuation device may be removed and the atraumatic tip component detached from the distal end of the device. The clot evacuation device may subsequently be reinserted into the outer sheath with an exposed distal end and positioned at or near the distal end of the outer sheath, such as depicted in FIG. 24B, to perform the clot evacuation procedure or other operation. This embodiment may be advantageous in reducing the number of components or amount of preparation needed for an operation with a two-step procedure, such as introduction and evacuation. For instance, a single navigation probe coupled to the clot evacuation device could be used in the introducing mode as well as the clot evacuation mode without the need for recalibration or reconfiguration. Also, the same visualization element can be used in the introducing mode as well as the clot evacuation mode and only one handpiece is needed.

Systems and Methods Utilizing an Integrated Introducer/Clot Evacuation Device

FIG. 25A shows an example of another embodiment, in which an optical introducer 1700 is removably insertable within a clot evacuation device 1750. The clot evacuation device 1750 may share similar features with the clot evacuation device 1650 shown in FIG. 24B. The clot evacuation device 1750 may, for example, comprise an outer tubular body 1751 and a number of operational elements disposed within the outer tubular body, including an evacuation hypotube 1753, a visualization element 1754, and one or more irrigation hypotubes 1755. The clot evacuation device 1750 may further comprise a shielding member 1760. The shielding member 1760 may be affixed to the distal end of the outer tubular body 1751 (i.e. a "windshield"). Similar to the atraumatic tip 1640 and the atraumatic tip component described above, in some embodiments, the shielding member 1760 may be entirely or partially transparent to allow visualization through the shielding member and may be constructed from the same or similar materials as the atraumatic tip 1640 or the atraumatic tip component. For example, the shielding member 1760 may be formed from injection molded plastic.

The shielding member 1760 may be permanently or removably attached to the outer tubular body 1751. The shielding member 1760 may form part of an atraumatic surface disposed on the distal end of the clot evacuation device 1750. It may substantially occupy the cross sectional space between the outer diameter of the optical introducer 1700 and the outer tubular body 1751. The shielding member 1760 comprises a proximal end and a distal end. The proximal end may comprise an inner surface disposed adjacent to the distal end of the outer tubular body 1751 and configured to face at least partially toward the internal lumen of the outer tubular body. The distal end may comprise an outer surface disposed distally of the distal end of the outer tubular body 1751 and configured to face away from the internal lumen of the outer tubular body. The inner and outer surfaces of the shielding member 1760 may be opposite sides of a uniformly thick piece of material or they may be distinct surfaces of a piece of material with a variable thickness profile, which may be a solid or may be hollow between the inner and outer surfaces.

The shielding member 1760 further comprises a hollow passage 1762 extending from its proximal end to its distal end. The hollow passage 1762 is generally parallel with the longitudinal axis of the outer tubular body 1751. The hollow passage 1762 may be a hole surrounded on all sides by portions of the shielding member 1760. The hollow passage 1762 may be positioned centrally along the longitudinal axis of the outer tubular body 1751 or may be positioned off-center as shown in FIG. 25A. In some embodiments, the hollow passage 1762 may be positioned along an outer circumference of the shielding member 1760 such that it is only partially surrounded by the shielding member 1760. The hollow passage 1762 may have generally circular end faces, which may be angled due to a tapering of the inner and/or outer surfaces of the shielding member 1760, on its proximal end and distal end. In some embodiments, the hollow passage 1762 may be generally cylindrical and may include a substantial sidewall if the inner and outer surfaces are significantly separated from one another. In other embodiments, the inner surface of the proximal end of the shielding member 1760 may directly meet the outer surface of the distal end of the shielding member at the hole such that there is no substantial sidewall to the hollow passage 1762. In some embodiments, the hollow passage 1762 may not be circular and/or cylindrical and may be any suitable shape.

The hollow passage 1762 may be configured to removably receive the optical introducer 1700. The optical introducer 1700 comprises an elongate body having a proximal end and a distal end and further comprises an atraumatic tip 1740 positioned at the distal end of the elongate body. The atraumatic tip 1740 may be the same or similar to the atraumatic tip 1640 shown in FIG. 24A. In embodiments where the outer diameter of the optical introducer 1600 is approximately the same as the outer diameter of the clot evacuation device 1750, the diameter of the optical introducer 1700 may be reduced relative to optical introducer 1600, but otherwise may retain the same or similar features. It may be shaped to be relatively rounded, semi-spherical, conical, and/or tapered to help separate tissue as the optical introducer traverses tissue and to avoid cutting, tearing, or coring the tissue. The atraumatic tip 1640 may be entirely or partially transparent to the visible light spectrum or to select wavelengths of light such that direct visualization may be achieved through the tip. For example, FIG. 25A shows an optical introducer 1700 with a transparent atraumatic tip 1740 similar to the atraumatic tip 1640.

Like optical introducer 1600, the elongate body of optical introducer 1700 may be configured to removably receive a visualization element 1728 or a visualization element 1728 may be integrally affixed within the elongate body. The visualization element may be the same or similar to the visualization element 1628 or other visualization elements described elsewhere herein. For example, it may include an image sensor 1729 disposed at or near its distal end and illumination elements disposed within. The distal end of the visualization element 1728 may extend into the atraumatic tip 1740, which may or may not comprise a flattened surface 1742. The atraumatic tip 1740 and flattened surface 1742 may be made of an entirely or partially transparent material. The optical introducer 1700 may be sized and configured to slide through the hollow passage 1762 of clot evacuation device 1700, such that at least a portion or the entirety of the atraumatic tip 1740 is positioned distally of the distal end of the shielding member 1760.

In some embodiments, such as shown in FIG. 25A, the evacuation hypotube 1753 may be aligned with the hollow passage 1762 such that the optical introducer is inserted from a proximal end of the clot evacuation device 1750 through the evacuation hypotube 1753 to reach the hollow passage 1762. When secured in a configuration for the optical introduction procedure, the distal end of the atraumatic tip 1740 may comprise the distal-most end of the combined clot evacuation and optical introducer device. The shape of the atraumatic tip 1740 may correspond with the shape of the shielding member 1760, such that when in an operative configuration, the surfaces of atraumatic tip 1750 and shielding member 1760 together form a generally smooth and relatively continuous atraumatic surface. In some embodiments, the optical introducer 1700 may be locked into position at a relative axial position along a length parallel to the longitudinal axis of the clot evacuation device 1750. Means for locking the optical introducer 1700 in place may be located at the proximal end of the clot evacuation device 1750, such as on a handpiece, which may share similar features to other handpieces described elsewhere herein.

During insertion of the combined optical introducer 1700 and clot evacuation device 1750, visualization element 1728 of the optical introducer 1700 may be used to provide guidance to the user in the same manner or similar to the way visualization element 1628 of optical introducer 1600 provides guidance during insertion. In some embodiments, the visualization element 1754 of the clot evacuation device 1750 may be used in addition to or alternatively to the visualization element 1728 to provide guidance. The view of visualization element 1754 may be directed through a transparent portion of the shielding member 1760.

Figure 25B:
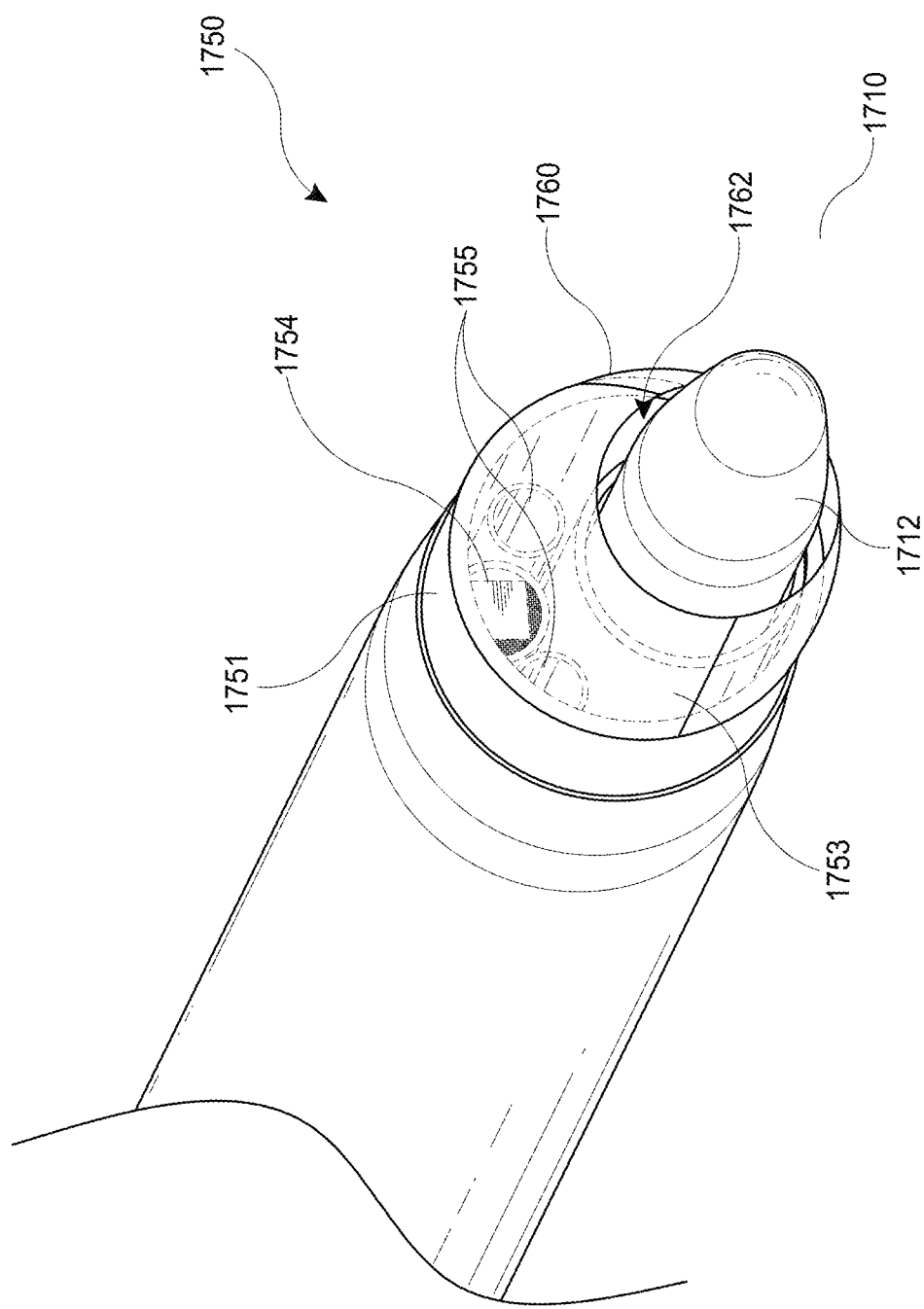

In some embodiments, the clot evacuation device 1750 may be used with an introducer 1710 which does not comprise its own visualization element, as shown in FIG. 25B. The introducer 1710 comprises an elongate body having a proximal end and a distal end and further comprises an atraumatic tip 1712 positioned at the distal end of the elongate body, similar to the optical introducer 1700. The atraumatic tip 1712 may be shaped the same or similar to the atraumatic tip 1740 shown in FIG. 25A, but may be entirely opaque. Alternatively, the atraumatic tip 1712 may also be partially or entirely transparent. In this embodiment, the visualization element 1754 of clot evacuation device 1750 may be used during the insertion step to provide imaging to the user in the same manner or similar to the way the visualization element 1728 of optical introducer 1700 and/or the visualization element 1628 of optical introducer 1600 provide guidance during insertion.

Figure 25C:
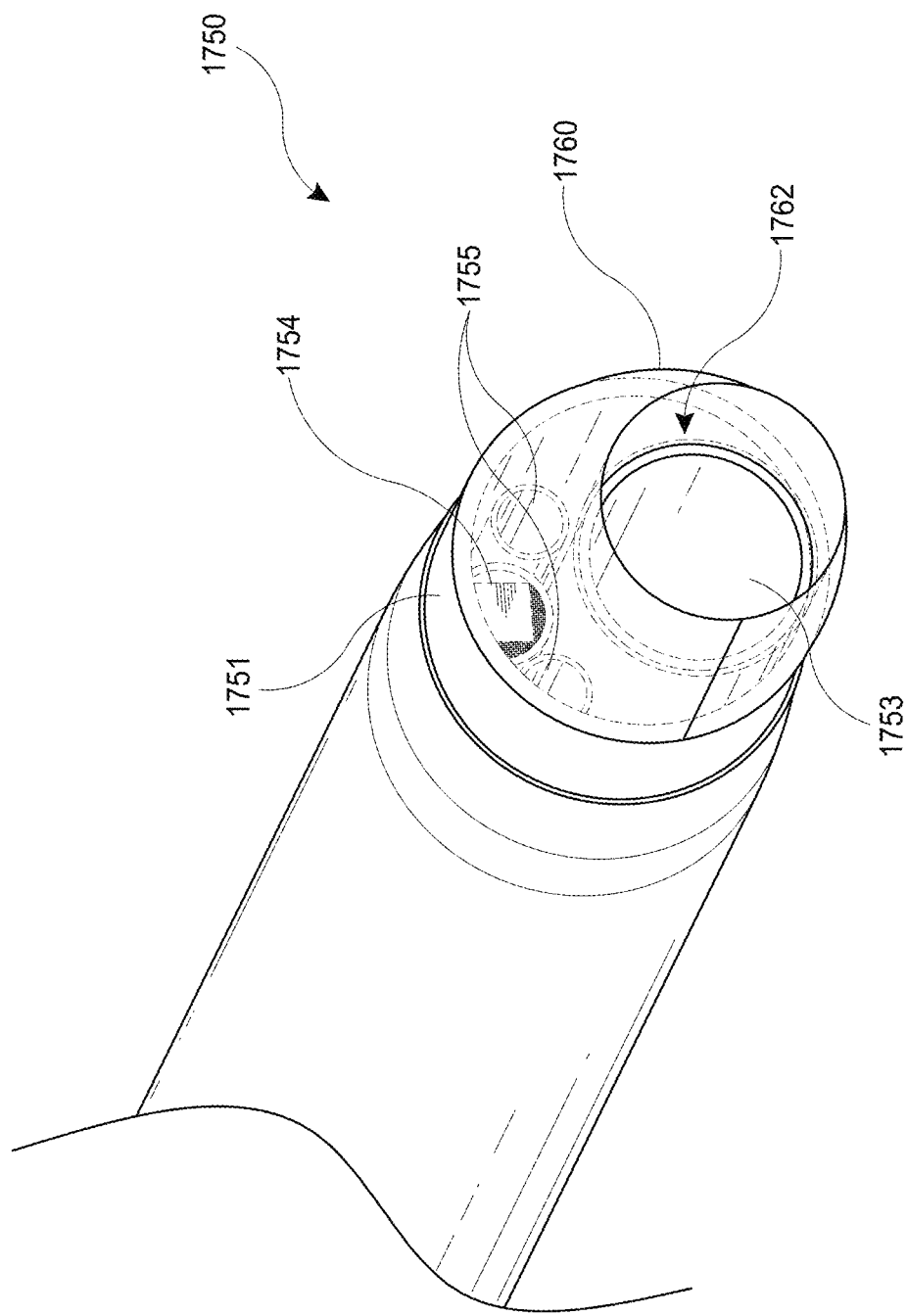

FIG. 25C shows clot evacuation device 1750 without either optical introducer 1700 or introducer 1710. The cross section of clot evacuation device 1750 taken along the elongate body 1752 may be the same or similar to that of clot evacuation device 1650, as shown in FIG. 24C. The proximal end of the clot evacuation device 1750 may likewise be the same or similar to that depicted in FIGS. 24D-24G or as depicted elsewhere herein. After the clot evacuation device 1750 is guided to a desired location inside the body, such as a position adjacent a blood clot, the introducer may be removed from the clot evacuation device, which remains in place. The introducer may be retracted from the outer tubular body 1751 through the proximal end of the clot evacuation device, essentially in a manner reverse to its insertion. Once the introducer is removed, at least some of the operative elements of the clot evacuation device 1750 may effectively operate through the now unoccupied hollow passage 1762. For example, as seen in FIG. 25C, the evacuation hypotube 1753 may aspirate through the hollow passage 1762, sucking tissue, fluid, and/or particulate through the hollow passage 1762 and into the evacuation hypotube 1753. In some embodiments, the evacuation hypotube 1753 may additionally be able to extend through the hollow passage 1762 such that it may operate on the distal side of the shielding member 1760. The view of the visualization element 1754 may be directed partially or entirely through a transparent portion of the shielding member 1760 and/or it may be directed partially or entirely through the hollow passage 1762. In some embodiments, the direction of the view of the visualization element 1754 may be deflected from the longitudinal axis toward the hollow passage 1762 so as to at least partially avoid the shielding member 1760. At least one irrigation hypotube 1755 may be configured to irrigate the distal end of the evacuation hypotube 1753 within the proximal end of the shielding member 1760. In some embodiments, if sufficient pressure is applied through the irrigation hypotube 1755, irrigation fluid may be delivered through the hollow passage 1762. In some embodiments, where the shielding member 1760 at least partially obstructs the direct delivery of irrigation fluid, the inner surface of the proximal end of the shielding member 1760 may be configured to redirect irrigation fluid through the hollow passage 1762. In some embodiments where the view of visualization element 1728 is directed through a transparent portion of the shielding member 1760, an irrigation hypotube 1655 may also be configured to wash that portion of the shielding member 1760 to optimize visualization.

Figure 26A:
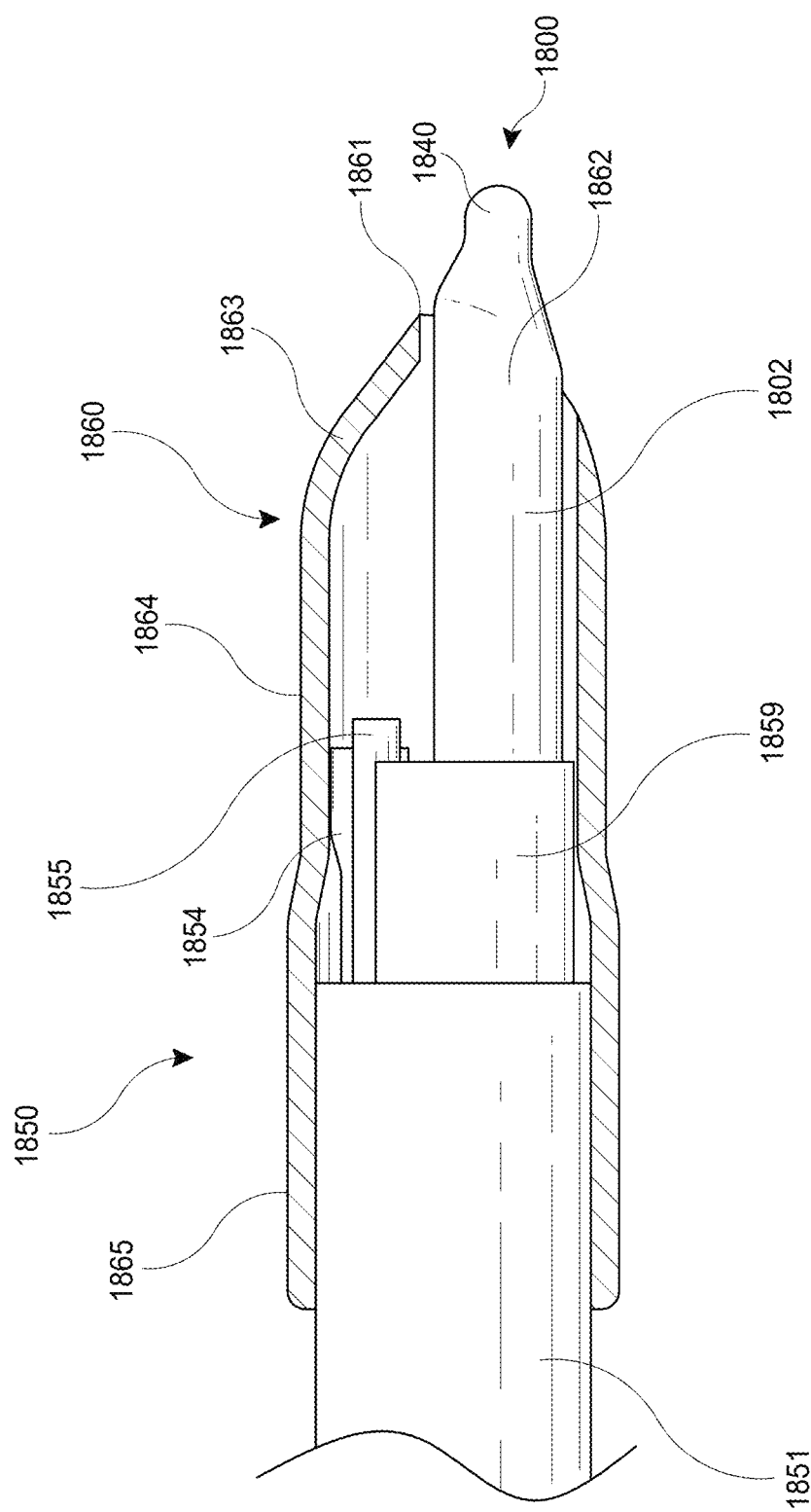
FIGS. 26A-I show examples of the clot evacuation device with a windshield and insertable introducer.
Figure 26B:
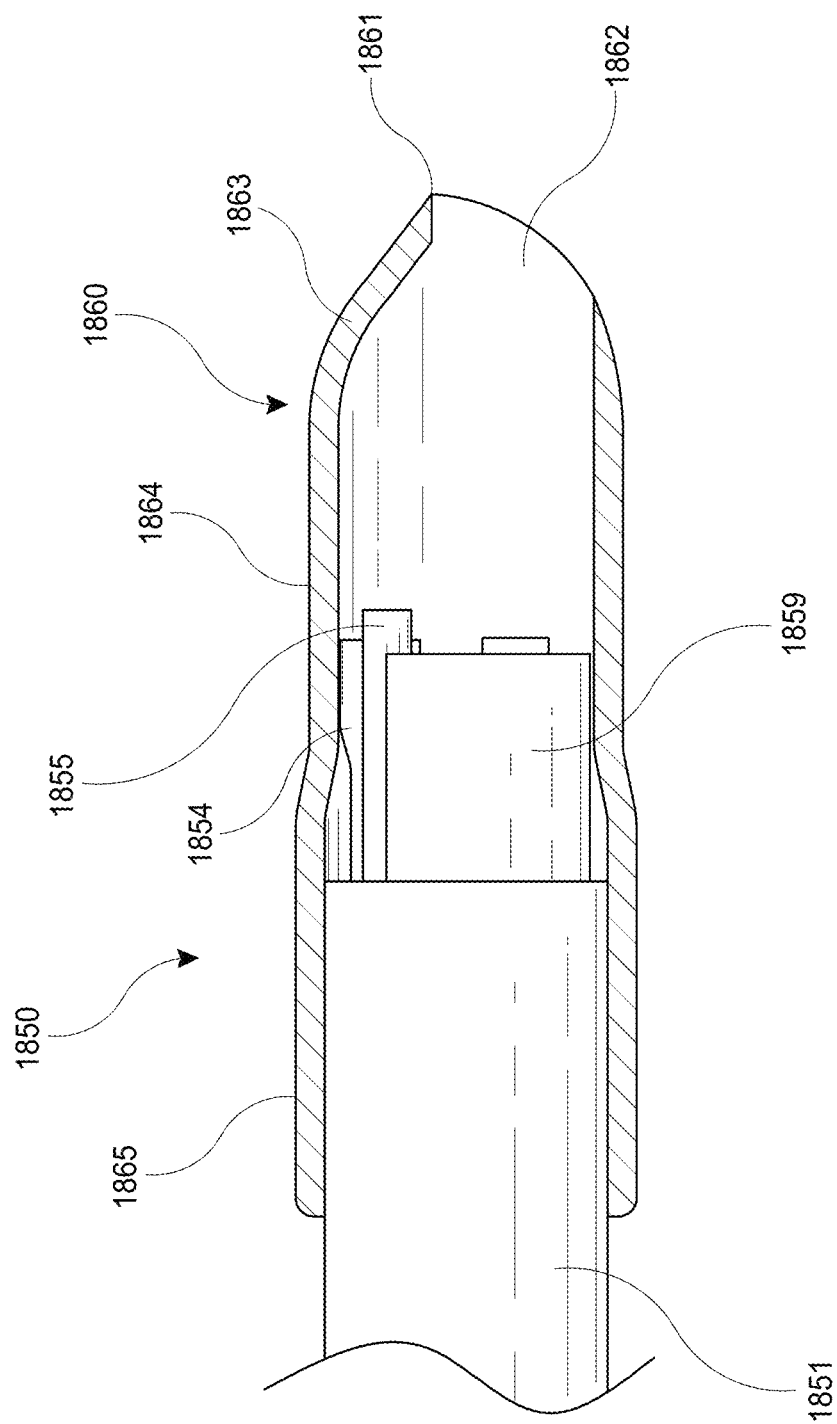
Figure 26C:
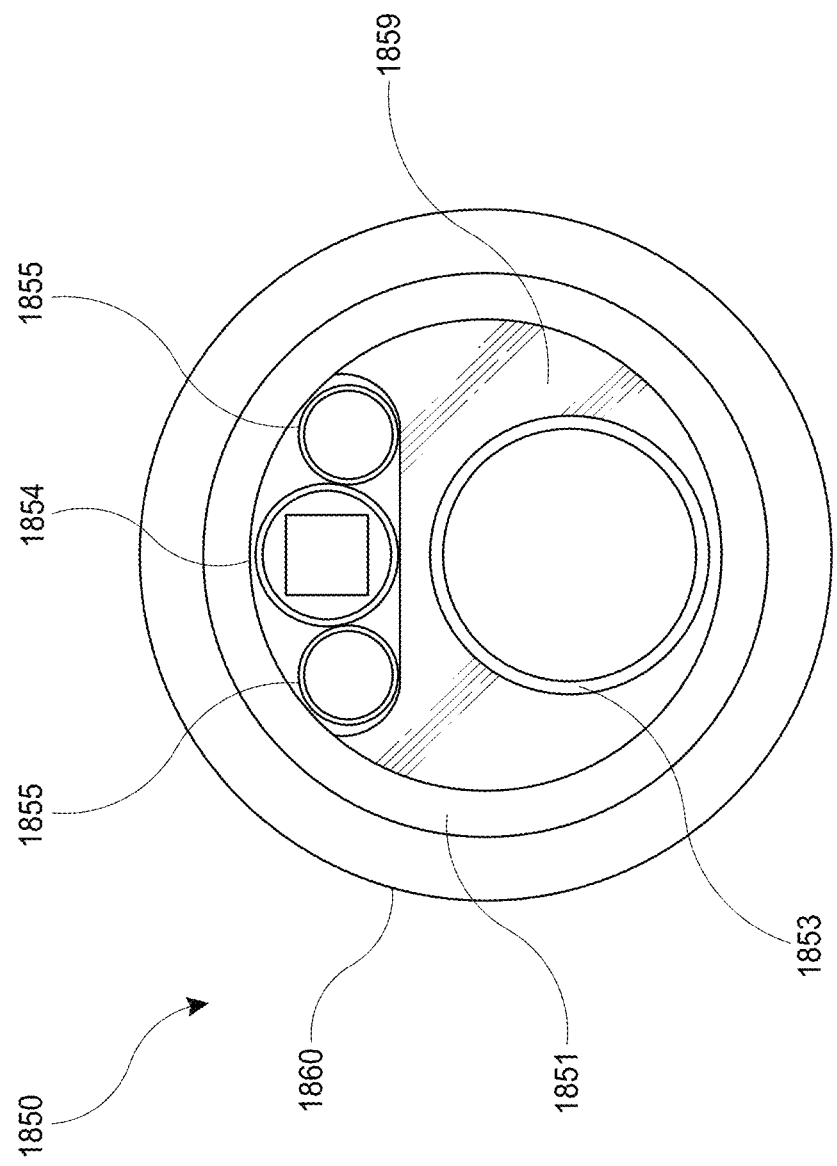

FIGS. 26A-26I depict examples of an alternative embodiment of a combined clot evacuation device 1850 and introducer 1800. FIG. 26A shows a side view of the distal end of clot evacuation device 1850 with introducer 1800 inserted in an operative position for introduction into the body (shielding member 1860 shown in cross-section). FIG. 26B shows the same side view with the introducer 1800 removed. FIG. 26C shows a cross-sectional view of the clot evacuation device 1850 looking from the distal end. In some embodiments, the cross section of clot evacuation device 1850 taken along the elongate body 1852 may be the same or similar to that of clot evacuation device 1650, as shown in FIG. 24C. The proximal end of the clot evacuation device 1850 may likewise be the same or similar to that depicted in FIGS. 24D-24G or as depicted elsewhere herein.

The introducer 1800 comprises an elongate body 1802 with a proximal end and a distal end and further comprises an atraumatic tip 1840 positioned at the distal end of the elongate body. The atraumatic tip 1840 may have a rounded or curved shape, and in some embodiments may be bullet-shaped. As with the embodiment depicted in FIGS. 25A-25C, the introducer 1800 may or may not be an optical introducer with an internal visualization. Like the clot evacuation device 1750, the clot evacuation device 1850 comprises an outer tubular body 1851, a shielding member 1860, an evacuation hypotube 1853, a visualization element 1854, and one or more irrigation hypotubes 1855. Clot evacuation device 1850 may further comprise an interior body 1859 (best seen in FIG. 26C) which substantially occupies the remaining cross sectional space within the inner diameter of the outer tubular body 1851, at least over a portion of the length of the outer tubular body. The interior body 1859 may support the operational elements and hold them in position. The operational elements may or may not be rigidly affixed to the interior body 1859.

Shielding member 1860 may be attached to the distal end of outer tubular body 1851 and extend distally therefrom. Shielding member 1860 is shaped in one embodiment with a somewhat pointed tip 1861 and an off-center hollow passage 1862 directly adjacent the pointed tip 1861. The shielding member 1860 comprises a tapered portion 1863, which contributes to forming an atraumatic surface along with the atraumatic tip 1840 of the introducer 1800, a cylindrical portion 1864 proximal to the tapered portion 1863, and a cylindrical sleeve 1865 with an expanded diameter relative to and proximal to the cylindrical portion 1864 for receiving the outer tubular body 1851. The cylindrical portion 1864 may smoothly transition into the cylindrical sleeve 1865 such that the outer surface remains atraumatic. In some embodiments, the outer diameter of the shielding member 1860 may be between about 6.0 mm and about 7.4 mm (e.g., 6.0 mm or 18 Fr, 6.8 mm or 20.4 Fr, 7.4 mm or 22 Fr) along either the cylindrical sleeve 1865 and/or the cylindrical portion 1864. In some instances, the outer diameter along the cylindrical sleeve 1865 may be about 7.4 mm and the outer diameter along the cylindrical portion 1864 may be about 6.0 mm. In some embodiments, the outer diameter along the cylindrical sleeve 1865 and the cylindrical portion 1864 may be approximately the same, such that there is no taper between them.

As shown in FIG. 26A, the operational elements of the clot evacuation device, including the evacuation hypotube 1853, the visualization element 1854, and the one or more irrigation hypotubes 1855, may extend beyond the distal end of the outer tubular body 1851. Furthermore, a portion of the elongate body 1802 of the introducer 1800 may extend beyond the distal end of the operational elements in its operative configuration. The cylindrical portion 1864 of the shielding member 1860 can be of a length suitable to accommodate the distance the operational elements extend beyond the outer tubular body 1851. It may potentially extend further in the distal direction to accommodate some or all of the portion of the elongate member 1802 that extends beyond the operational elements. The entirety or portions of the shielding member 1860 may be transparent to allow visualization through the shielding member 1860. The entirety or portions of the cylindrical portion 1864, particularly, may be transparent to allow side visualization, such as when wide-angle visualization elements are employed or visualization elements are employed in which the view is directed at least partially toward the side (i.e. in a radial direction). The inner diameter of the cylindrical sleeve 1865 may be configured to mate with the outer diameter of the outer tubular body 1851. The shielding member 1860 may be removably secured to the outer tubular body 1851, such as by a friction fit, or it may be permanently affixed to the outer tubular body 1851 by any suitable means, such as a suitable adhesive, for example.

Figure 26D:
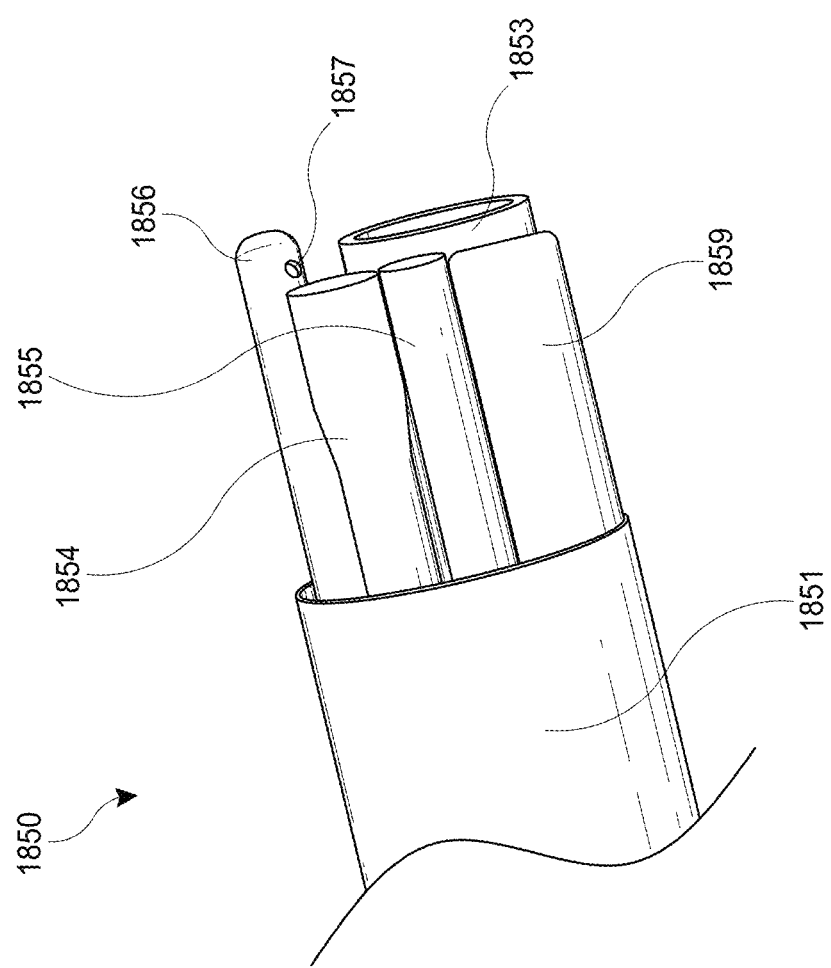
Figure 26E:
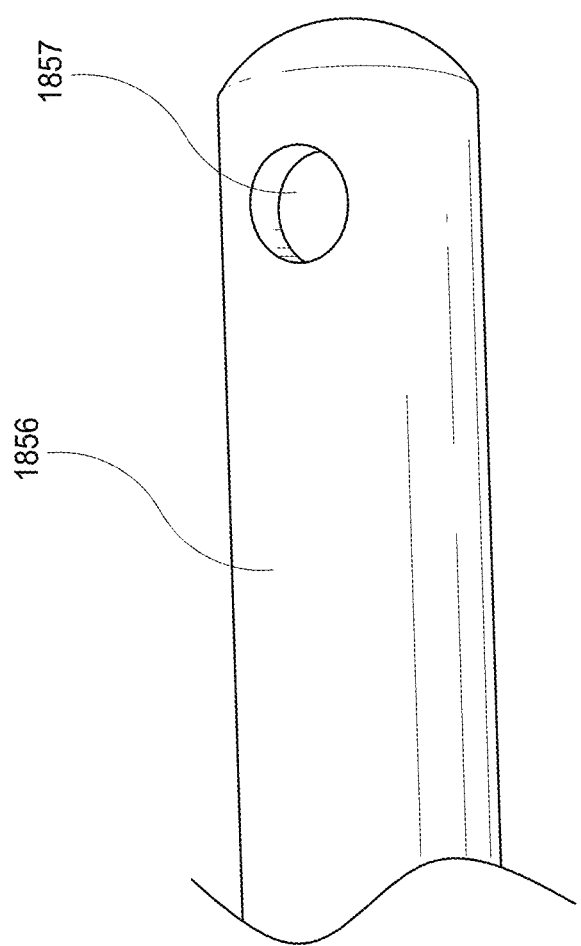

FIG. 26D shows a perspective view of an example of clot evacuation device 1850 with the shielding member 1860 removed. FIG. 26E shows a perspective view of an irrigation hypotube 1856 which is configured specifically for irrigating a visualization element 1854. As seen in FIG. 26D, when an irrigation hypotube 1856 is configured to irrigate the visualization element 1854 it may comprise a closed face distal end and an irrigation aperture 1857 in the sidewall of the hypotube 1856 which is positioned further in the distal direction than the distal end of the visualization element 1854. The irrigation hypotube 1856 may be positioned adjacent to the visualization element 1854 and the irrigation aperture 1857 may be oriented toward the visualization element 1854. Irrigation fluid may be forced under pressure through the irrigation aperture 1857 and onto the distal end or directly in front of the distal end of the visualization element 1854 for cleaning the lens and/or clearing the view directly in front of the visualization element 1854. In some embodiments, an irrigation hypotube 1855 may also be configured to wash transparent portions of the shielding member through which visualization is achieved.

Figure 26F:
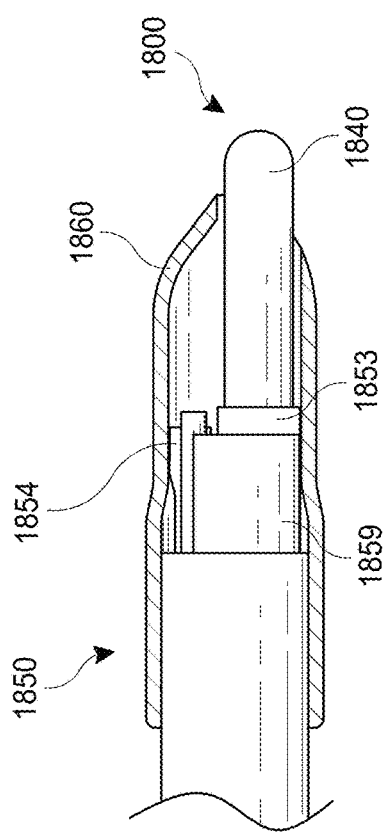
Figure 26G:
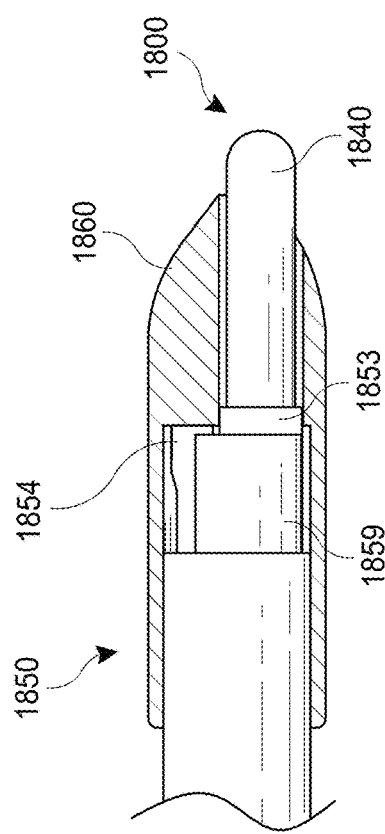
Figure 26H:
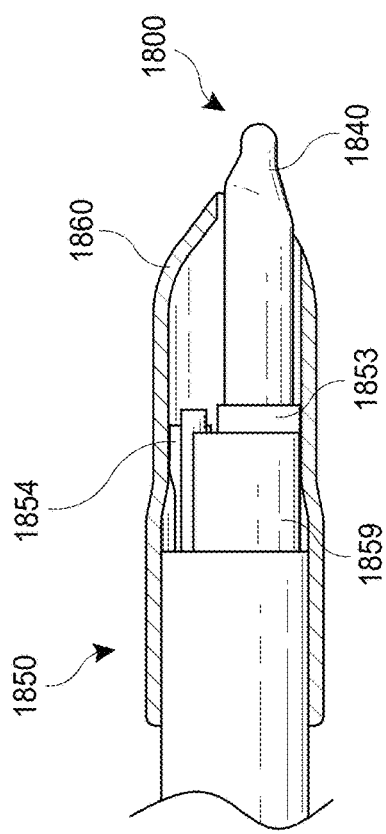
Figure 26I:
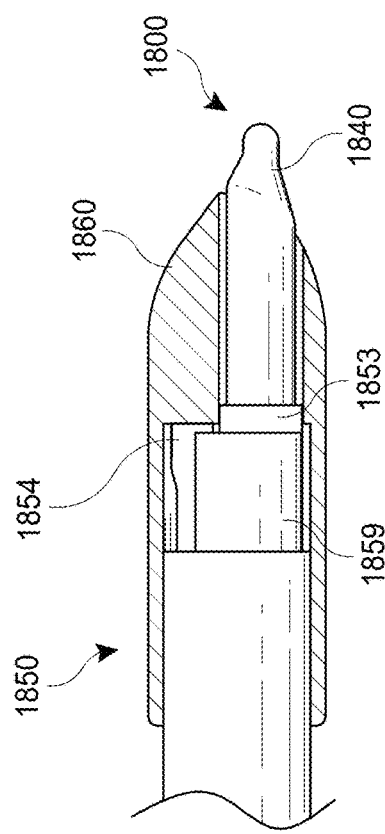

FIGS. 26F-26I show side views of examples of a clot evacuation device 1850 and insertable introducer 1800 with various configurations of the shielding member 1860 (shown in cross-section) and atraumatic tip 1840. In FIGS. 26F and 26G, the shielding member 1860 is shelled (i.e. hollow), such that there is a space between the distal ends of the operational elements, including the visualization device 1854, and the shielding member 1860. This space may allow for use of operational elements, such as irrigation hypotubes 1855 inside the shielding member 1860. In FIGS. 26H and 26I, the shielding member 1860 is solid, such that the shielding member extends to and/or abuts the distal end of the visualization element 1854, leaving substantially no space between the visualization element 1854 and the shielding member 1860. Additional operational elements, such as irrigation hypotubes 1855, may be omitted from these devices. The proximity of the transparent portion of the shielding member 1860 to the visualization device 1854 may allow better visualization. In FIGS. 26F and 26H, the atraumatic tip is pointed, in that it comprises a further taper distal to the shielding member 1860 before reaching the atraumatic tip. In FIGS. 27G and 26I, the atraumatic tip is domed. The clot evacuation device 1850 shown in FIG. 26F may be the same or similar to that shown in FIG. 26A.

Inserting the introducer through the evacuation hypotube of the clot evacuation device, such as shown in the examples of FIGS. 25A-25C and FIGS. 26A-I may be advantageous for reducing the device volume needed to accommodate the evacuation hypotube and the introducer. As in these examples, the outer diameter of the clot evacuation tube may be approximately the same size as the diameter of the hollow passage of the shielding member, at least at its distal end. This may be advantageous in embodiments where the evacuation hypotube is configured to be selectively extendable through the hollow passage during aspiration. In other embodiments, the introducer may not be inserted through the evacuation hypotube, but may be inserted through the outer tubular body in a space unoccupied by any other operational elements.

In some embodiments of the combined clot evacuation device and introducer, the outer diameter of the introducer is approximately the same as the diameter of the hollow passage, for example as seen in FIG. 26A, such that the distal end of the clot evacuation device is substantially closed off from the physiological environment during insertion. In other embodiments, the distal end of the elongate body of the introducer may comprise a filler member/sealing member. The filler member may be generally annular and surround the circumference of the introducer proximal to the atraumatic tip. The filler member may occupy the residual space between the outer diameter of the introducer and the hollow passage in embodiments where the diameter of the hollow passage is larger than that of the introducer. In some embodiments where the introducer is inserted through the working channel of an evacuation hypotube, the outer diameter of the combined introducer and filler member may be larger than the inner diameter of the evacuation hypotube. In such cases, the filler member may be compliant such that it may be compressed both during insertion of the introducer and during removal of the introducer such that the introducer with attached filler member can fit within the working channel. The filler member may be a foam ring for example.

In another embodiment, as described elsewhere herein, the filler member may be a balloon attached to the introducer which may be inflated after being inserted and extended through the working channel and deflated prior to retraction. The introducer may further comprise a channel coupled to the balloon or other integrated means for inflating and deflating the balloon.

In another embodiment, the filler member may a semi-rigid/semi-flexible film which is affixed to the introducer, similar to the balloon. The film may form an annular ring around the introducer and may operate similarly to the balloon, except that it is neither inflated nor deflated. The outer diameter of the film may be larger than the diameter of the hollow passage and the film may be rigid enough such that it effectively seals the space between the outer diameter of the introducer and the hollow passage when pressed against the hollow passage. The film may flex to an extent like a tent over a tent pole. This flexing may allow the introducer to be extended an additional length beyond the hollow passage without compromising the seal between the introducer and the hollow passage. The flexible nature of the film may also allow the film to collapse along the circumference of the introducer as the introducer is inserted into or retracted from the working channel of the clot evacuation device.

Embodiments where the hollow passage is larger than the diameter of the introducer may provide some advantages. A larger hollow passage may allow for direct visualization by the clot evacuation visualization element through the hollow passage rather than through the shielding member. In some instances this may provide better imaging. The larger opening may also allow for more operational procedures (e.g. irrigation) to occur through the hollow passage. Simultaneously, a smaller diameter working channel, through which the introducer passes (thereby limiting the size of the introducer), may provide more volume within the device to incorporate operational elements.

Figure 27A:
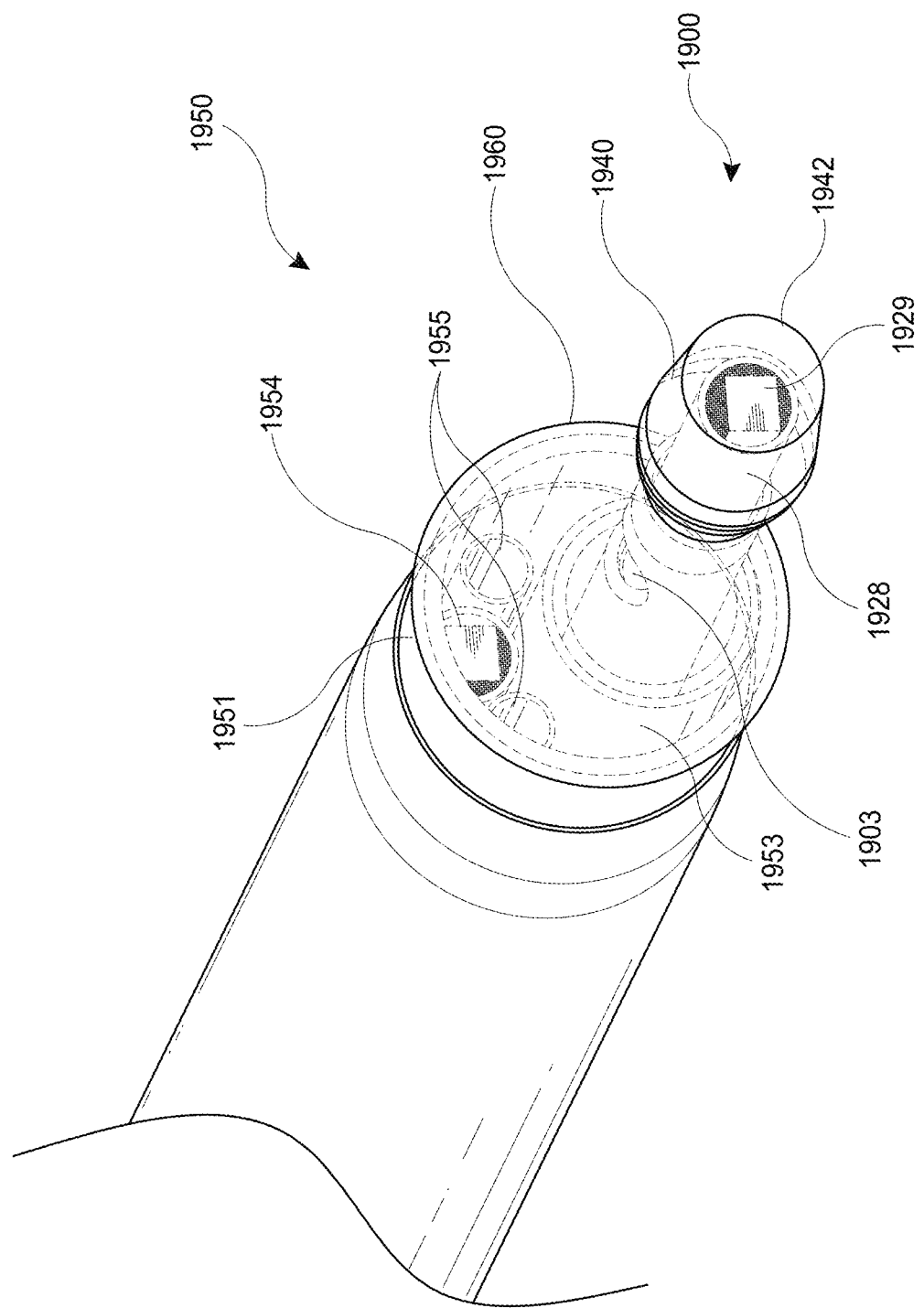
FIGS. 27A-E show examples of a clot evacuation device and insertable introducer with a balloon shielding member.

Systems and Methods Utilizing an Integrated Introducer/Clot Evacuation Device with an Inflatable Balloon FIG. 27A shows an example of another embodiment, in which an optical introducer 1900 is removably insertable within a clot evacuation device 1950. The optical introducer 1900 may share identical or similar features with the optical introducer 1700, shown in FIG. 25A. The optical introducer 1900 comprises an elongate body having a proximal end and a distal end and further comprises an atraumatic tip 1940 positioned at the distal end of the elongate body. The atraumatic tip 1940 may be shaped to be relatively rounded, semi-spherical, conical, and/or tapered to help separate tissue as the optical introducer traverses tissue and to avoid cutting, tearing, or coring the tissue. The atraumatic tip 1940 may be entirely or partially transparent to the visible light spectrum or to select wavelengths of light such that direct visualization may be achieved through the tip. Like optical introducer 1700, the elongate body of optical introducer 1900 may be configured to removably receive a visualization element 1928 or a visualization element 1928 may be integrally affixed within the elongate body. The visualization element 1928 may be the same or similar to the visualization element 1728 or other visualization elements described elsewhere herein. For example, it may include an image sensor 1929 disposed at or near its distal end and illumination elements disposed within. The distal end of the visualization element 1928 may extend into the atraumatic tip 1940, which may or may not comprise a flattened surface 1942.

The clot evacuation device 1950 may share similar features with the clot evacuation device 1750 shown in FIG. 25A. The clot evacuation device 1950 may, for example, comprise an outer tubular body 1951 and a number of operational elements disposed within the outer tubular body 1951, including an evacuation hypotube 1953, a visualization element 1954, and one or more irrigation hypotubes 1955. The components of the clot evacuation device 1950 may be positioned the same or similar to the components of the clot evacuation device 1650 as schematically illustrated in FIG. 24C. The combined clot evacuation device 1950 may further comprise a shielding member 1960.

Unlike clot evacuation device 1750, in which the shielding member 1760 is a windshield affixed to the distal end of the outer tubular body 1751, the shielding member 1960 is a balloon affixed to the distal end of the elongate body of the optical introducer 1900. The balloon 1960 may be at least partially transparent to the visible light spectrum or select wavelengths such that visualization may be achieved through the balloon 1960. Similar to the windshield shielding member 1760, the balloon shielding member 1960 may substantially occupy the cross-sectional space between the outer diameter of the optical introducer 1900 and the outer tubular body 1951 and in doing so shield the operational elements disposed within the outer tubular body from bodily tissue disposed distally to the outer tubular body 1951. The outer diameter of the balloon 1960 may extend to approximately the inner or outer diameter of the outer tubular body 1951 or it may extend somewhat beyond the outer diameter of the outer tubular body 1951, effectively increasing the outer diameter of the clot evacuation device 1950.

In some embodiments, the combined clot evacuation device 1950 and optical introducer 1900 may comprise both a windshield and a balloon 1960, as described elsewhere herein. In such embodiments, the outer diameter of the balloon may extend to approximately the diameter of a hollow passage within the windshield. In other embodiments, the clot evacuation device 1950 may comprise a collar affixed to the distal end of the outer tubular body 1951. The collar may be flexible and may help form a seal between the outer tubular body 1951 and the outer diameter of the balloon 1960.

The balloon 1960 may be fabricated and attached to the optical introducer 1900 by any suitable means, including those known in the art for attaching balloons to introducers for expanding the anatomical working space within the body upon inflation. The balloon 1960 may be formed to be generally toroidal in shape such that it surrounds the entire circumference of the optical introducer 1900. The outer surface of the balloon 1960 may be generally rounded, which may contribute to an atraumatic surface disposed on the distal end of the combined clot evacuation device 1950 and optical introducer 1900. In some embodiments, the balloon 1960 may comprise fiber reinforcements, which may alter the shape of the inflated balloon 1960. The fiber reinforcements may reduce the amount by which the balloon 1960 bulges and can allow the balloon 1960 to fully extend to the diameter of the outer tubular member 1951 without portions significantly bulging beyond the outer tubular body 1951. The balloon 1960 may be controllably inflatable and/or deflatable. The elongate body of the optical introducer 1900 may comprise an air lumen leading from the proximal end of the device to an inflation aperture 1903 in its sidewall. The inflation aperture 1903 may be in fluid communication with the interior of the balloon 1960 and an air-tight seal between the interior and exterior of the balloon 1960 may be formed around the inflation aperture on the surface of the elongate body of the optical introducer 1900. The user may alter the air pressure within the air lumen to either inflate or deflate the balloon 1960.

The operation of the combined clot evacuation device 1950 and optical introducer 1900 may be similar to that of clot evacuation device 1750 and optical introducer 1700. The optical introducer 1900 may be inserted into a working channel of the clot evacuation device 1950 with the balloon 1960 deflated. The working channel of the clot evacuation device 1950 shown in FIG. 27A is the clot evacuation hypotube 1953. In other embodiments, the working channel may not be the lumen of a clot evacuation hypotube 1953. Once the inflation aperture 1903 has passed sufficiently beyond the distal end of the working channel and the distal ends of the other operational elements, the balloon 1960 may be inflated, sealing off the distal end of the outer tubular body 1951. In some embodiments in which the distal end of the outer tubular body 1951 extends beyond the distal end of the operational elements disposed within its internal diameter, the inflation aperture 1903 may positioned within the outer tubular body 1951 such that the outer surface of the balloon 1960 is expanded to interface with the internal diameter of the outer tubular body 1951. In other embodiments, the inflation aperture 1903 may be positioned just beyond the distal end of the outer tubular body 1951 such that the outer surface of the balloon 1960 abuts the end face of the outer tubular body 1951 or somewhere in between.

After the balloon 1960 is inflated, the combined clot evacuation device 1950 and optical introducer 1900 may be inserted into the body in the same manner as the combined clot evacuation device 1750 and optical introducer 1700. The visualization element 1928 of the optical introducer 1900 may be used to guide insertion of the device as described elsewhere herein. If the balloon 1960 is at least partially transparent, the visualization element 1954 of the clot evacuation device 1950 may be used in addition to or alternatively to visualization element 1928, by viewing through the balloon 1960. In some embodiments, a balloon 1960 and a windshield may be provided, in which case the view of the visualization element 1954 may also be directed through a transparent portion of the windshield. Once the clot evacuation device 1950 is in proper position, the balloon 1960 may be deflated and the optical introducer 1900 retracted from the working channel, leaving the distal end of the outer tubular body 1951 open such that the operative elements may freely operate on the blood clot or other bodily tissue. Upon completion of the procedure, the clot evacuation device 1950 may be removed from the body.

Figure 27B:
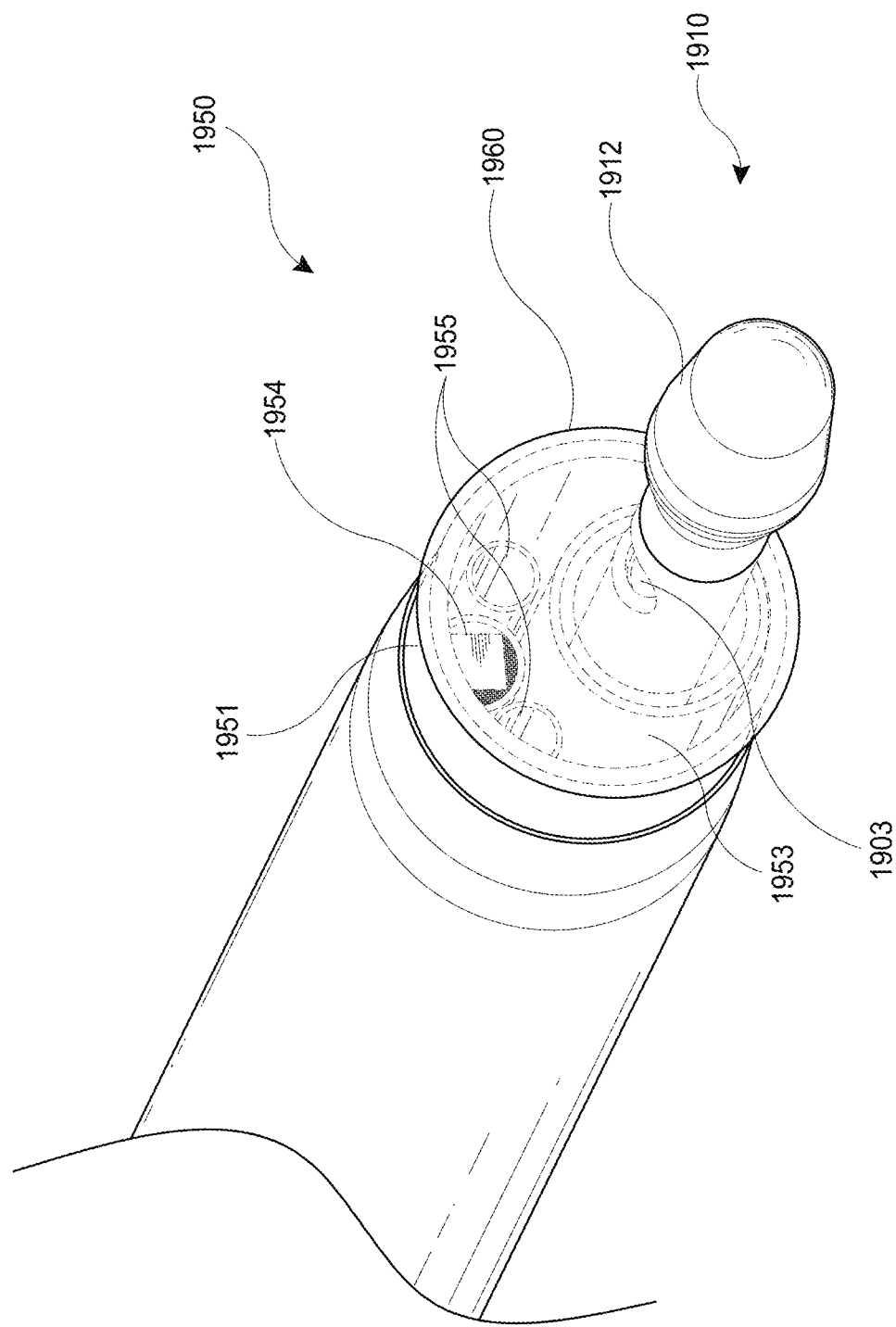

In some embodiments, the clot evacuation device 1950 may be used with an introducer 1910 which does not comprise its own visualization element, as shown in FIG. 27B. The introducer 1910 may share similar features to the introducer 1710 shown in FIG. 25B, including comprising an atraumatic tip 1912, except that it comprises a balloon shielding member 1960 the same as that of the optical introducer 1900. In this embodiment, the visualization element 1954 of clot evacuation device 1950 may be used to provide imaging to the user through the balloon 1960 in the same manner or similar to the way the visualization element 1754 of the clot evacuation device 1750 or as described elsewhere herein for providing guidance during insertion.

Figure 27C:
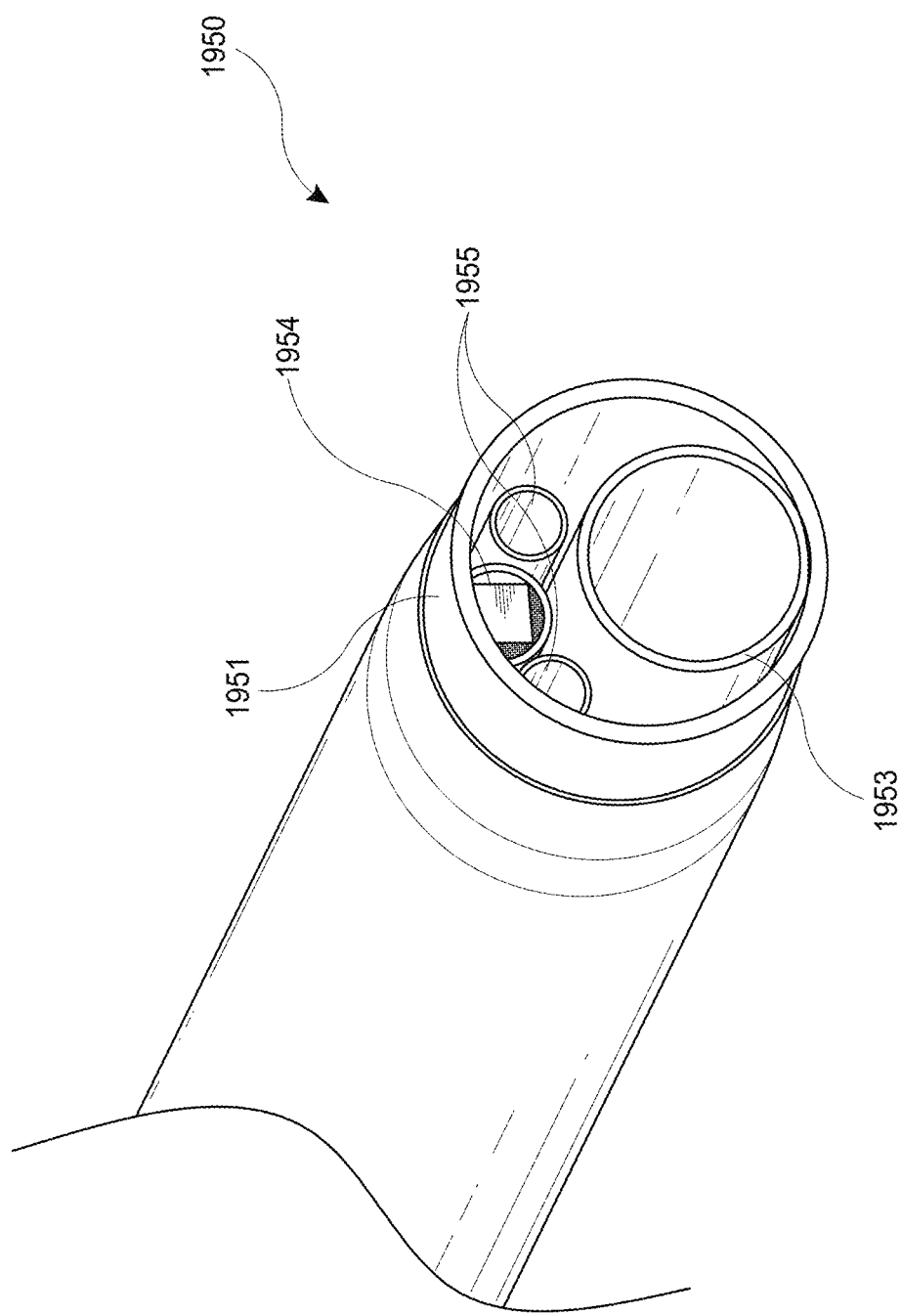

FIG. 27C shows clot evacuation device 1950 without either optical introducer 1900 or introducer 1910. The cross section of clot evacuation device 1950 taken along the elongate body 1952 may be the same or similar to that of clot evacuation device 1650, as shown in FIG. 24C. The proximal end of the clot evacuation device 1950 may likewise be the same or similar to that depicted in FIGS. 24D-24G or as depicted elsewhere herein. After the clot evacuation device 1950 is guided to a desired location inside the body, such as a position adjacent a blood clot, the introducer may be removed from the clot evacuation device, which remains in place. The introducer may be retracted from the outer tubular body 1951 through the proximal end of the clot evacuation device 1950, essentially in a manner reverse to its insertion. The operational elements, including the evacuation hypotube 1953, the visualization element 1954, and the one or more irrigation hypotubes 1955 may operate freely through the distal open face of the outer tubular member 1951.

Figure 27D:
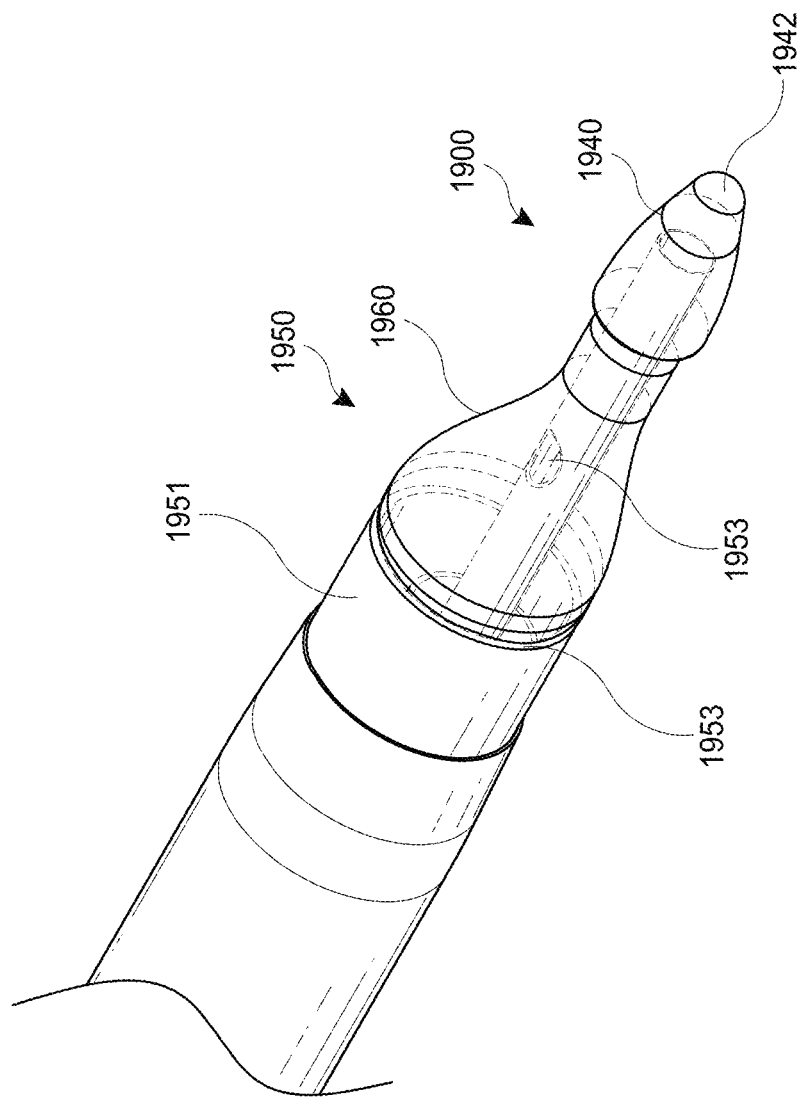
Figure 27E:
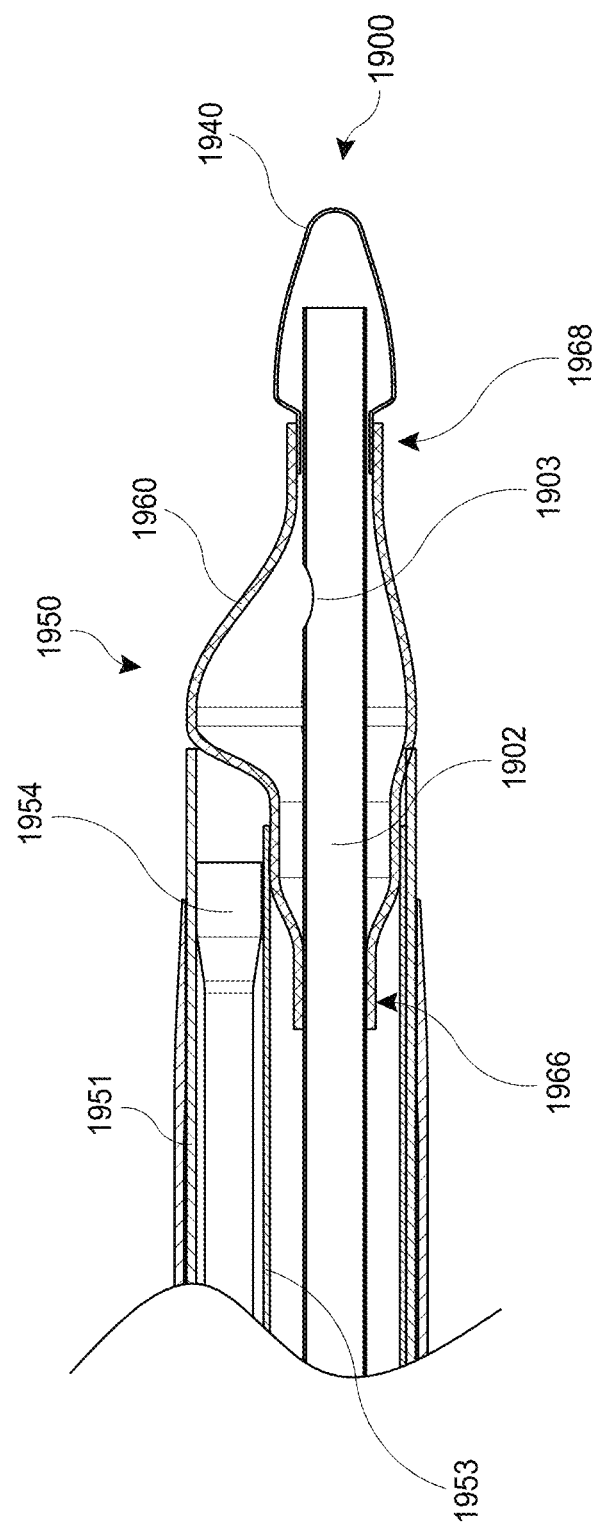

FIGS. 27D and 27E show another example of a clot evacuation device 1950 with an introducer or optical introducer 1900. FIG. 27D is a perspective view of the distal end of the clot evacuation device 1950 with introducer or optical introducer 1900 inserted through the evacuation hypotube 1953 and balloon 1960 inflated. FIG. 27E is a side cross-sectional view of the distal end of the clot evacuation device 1950 with introducer or optical introducer 1900 inserted through the evacuation hypotube 1953 and balloon 1960 inflated. In the example shown in FIGS. 27D and 27E, the balloon 1960 is affixed to the elongate body 1902 of the introducer or optical introducer 1900. The interior of the balloon 1960 may comprise the volume between the surface of the balloon 1960 and the surface of the elongate body 1902 between a proximal seal 1966 and a distal seal 1968. The balloon 1960 may be generally tubular, comprising a proximal opening and a distal opening, and the proximal and distal seals 1966, 1968 can be formed by affixing the circumferences of the proximal and distal openings to the elongate body 1902 to form air-tight seals around the elongate body 1902. The proximal seal 1966 may be formed at a location along the elongate body 1902 positioned within in the evacuation hypotube 1953 when the introducer or optical introducer 1900 is inserted to an operative distance. The distal seal 1968 may be formed over a portion of the atraumatic tip 1940 surrounding the elongate body 1902. The seals 1966, 1968 may be formed by adhesive, compressive retention elements, or any other suitable means. The inflation aperture 1903 is positioned between the proximal seal 1966 and distal seal 1968 such that it is in fluid communication with the interior of the balloon 1966. The body of the balloon 1960 may have one or more tapered surfaces, which can be formed from reinforcement fibers. When inflated, the balloon 1960 may expand to a shape configured to close off the outer tubular body 1951 and/or form an atraumatic surface proximal to the atraumatic tip 1940. The atraumatic tip 1940 may be positioned a sufficient distance away from the distal end of the outer tubular body 1951 to allow for a more gradual taper by the surface of the balloon 1960. When inflated, the balloon 1960 may expand to several different diameters along the length of the elongate body 1902. For example, the balloon 1960 may expand to a first diameter, approximately equal to the diameter of the evacuation hypotube 1953 to seal off the evacuation hypotube 1953, and may expand along a more distal portion to a second diameter, approximately equal to the diameter of outer tubular body 1951 to seal off the outer tubular body 1951. The atraumatic tip 1940 may comprise any shape disclosed herein. As shown in FIGS. 27D and 27E, the atraumatic tip 1940 may be "bullet" shaped. The outer diameter of the atraumatic tip 1940 may be larger than the outer diameter of the balloon 1960 at the distal seal 1968, which may protect the integrity of the distal seal 1968 as the combined clot evacuation device 1950 and introducer or optical introducer 1900 is inserted into the body.

Figure 28:
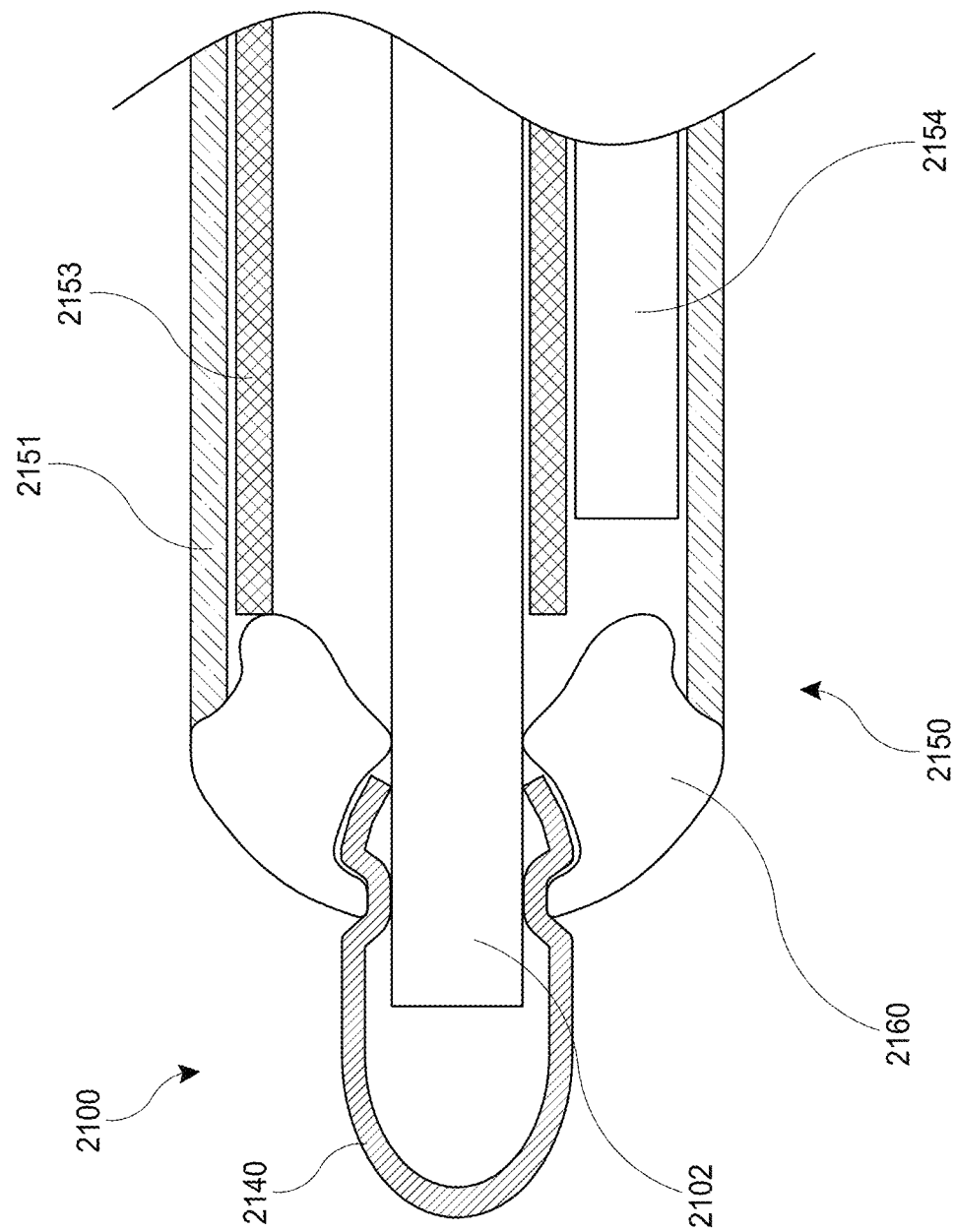
FIG. 28 schematically illustrates a side view cross-section of an alternative embodiment of a clot evacuation device with insertable introducer and a balloon shielding member.

FIG. 28 schematically illustrates a cross-sectional side view of a clot evacuation device 2150 and optical introducer 2100. In this example, the clot evacuation device 2150 comprises an outer tubular body 2151 and a number of operational elements disposed within the outer tubular body 2151, including an evacuation hypotube 2153 and visualization element 2154. The optical introducer 2100 comprises an elongate body 2102 with an internally disposed visualization element, a transparent atraumatic tip 2140 secured to the distal end of the elongate body 2102, and a balloon 2160 attached to and surrounding the distal end of the elongate body 2102, proximal to the atraumatic tip 2140. The balloon 2160 may operate the same or similar to the balloon 1960 of the combined clot evacuation device 1950. The optical introducer 2100 is inserted within the working channel of the clot evacuation hypotube 2153. In the example shown in FIG. 28, the outer diameter of the elongate body 2102 is less than the inner diameter of the clot evacuation hypotube 2153.

Systems and Methods for Adapting an Endoscope to Receive an Introducer

In other embodiments, the device may not be a clot evacuation device or other operational device but may be an adaptor kit for transforming standard endoscopes into optical introducers. The adaptor kit may include a shielding member and an introducer and may be configured to interface with specific models of endoscopes existing within the medical device industry. The introducer may be specifically configured to be removably inserted within an open working channel of a standard endoscope, similar to the way introducers are received within the working channel of clot evacuation devices described elsewhere herein. The shielding member may be configured to removably attach to the distal end of the standard endoscope (i.e. a windshield). It may be secured to the standard endoscope by any suitable means. For example, the shielding member may comprise protrusions configured to wedge into a recess on the standard endoscope and/or the shielding member may be held in place by one or more thin tension cables that travel through the working channel (or another lumen) to the proximal end of the standard endoscope. The shielding member may have a hollow passage for allowing the introducer to extend through as described elsewhere herein. The atraumatic tip of the introducer and the outer surface of the shielding member may cooperate to form an atraumatic distal end to the adapted endoscope. The introducer may or may not comprise its own visualization element. If the introducer comprises a visualization element, the introducer may be an optical introducer as described elsewhere herein. The shielding member may be attached to the standard endoscope and the introducer inserted through the working channel prior to its insertion into the body. During insertion, the endoscope may provide direct visualization through a transparent portion of the shielding member so as to guide the introduction procedure. Upon proper positioning of the standard endoscope the introducer may be removed through the working channel. Various operational instruments may be subsequently inserted through the working channel of the standard endoscope to perform the appropriate operation through the hollow passage of the shielding member. The shielding member may remain in place during the operational procedure and the visualization components of the standard endoscope may continue to operate through the shielding member. The shielding member may be removed after the standard endoscope is retracted from the body. The adaptor kit may be for single use operations or may be reusable. There may be different configurations of the introducer and shielding member for adapting to different endoscopes.

Additional Examples of Clot Evacuation Devices

Figure 29A:
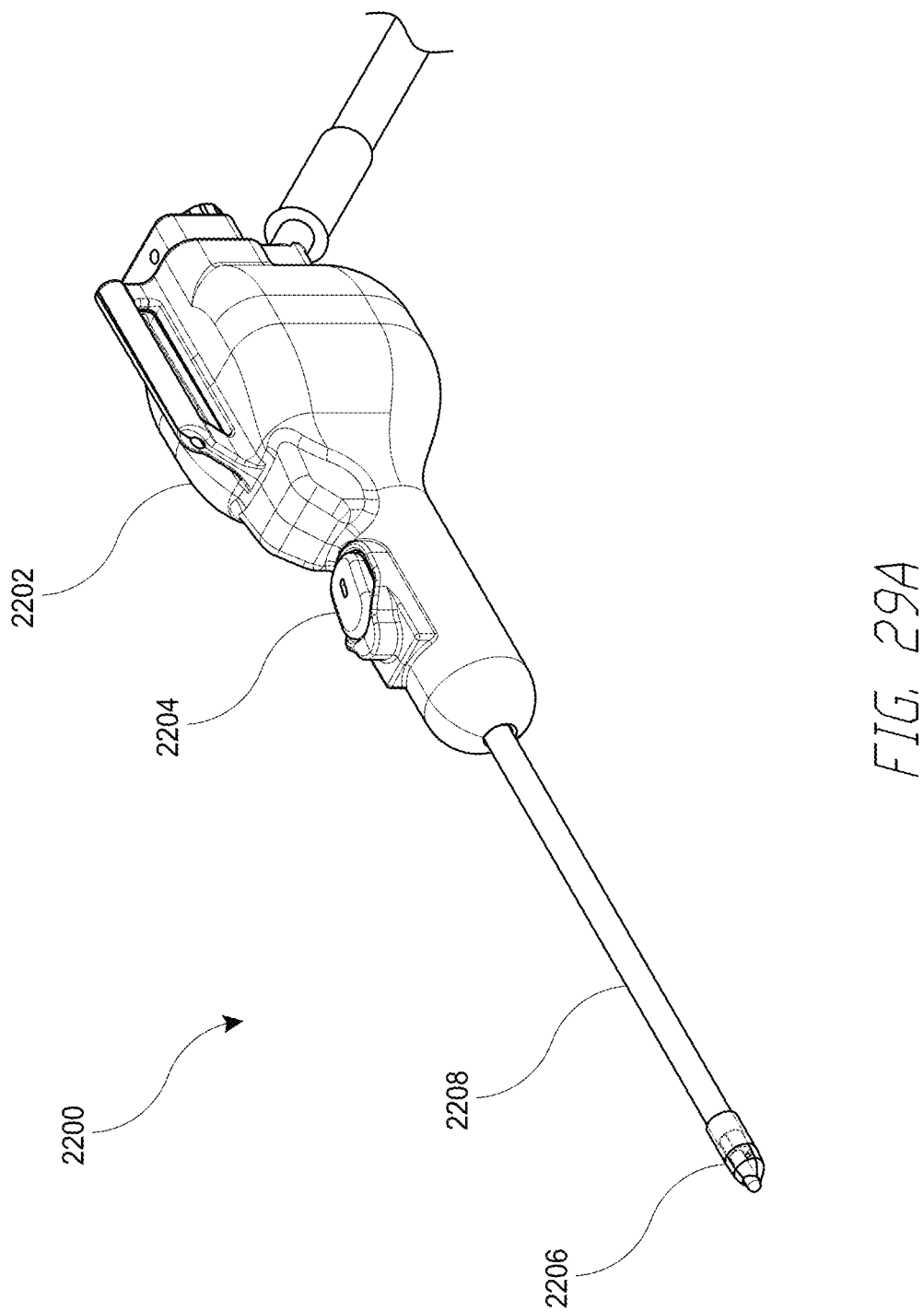
FIGS. 29A-G show various views of an example of a clot evacuation device.
Figure 29C:
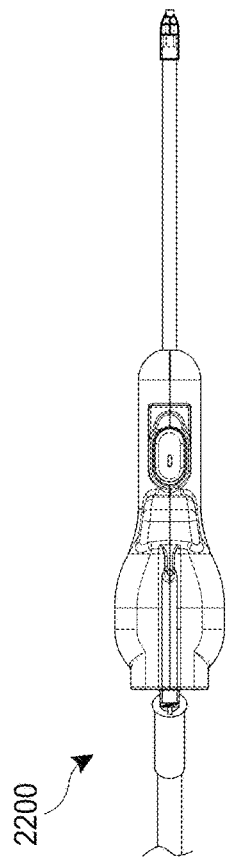
Figure 29D:
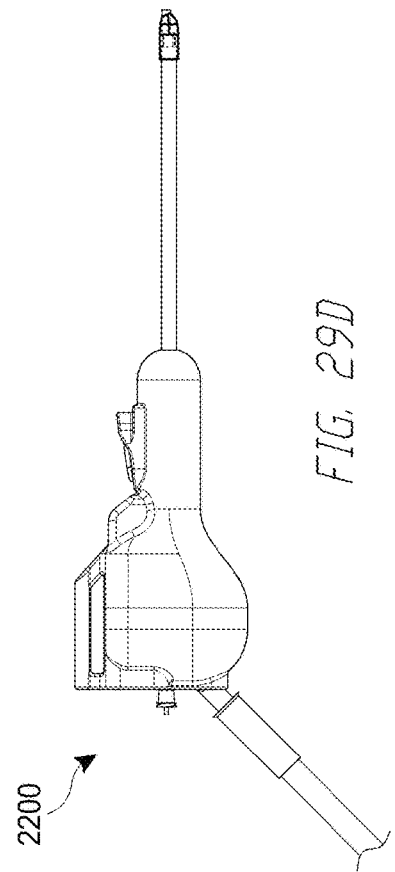
Figure 29E:
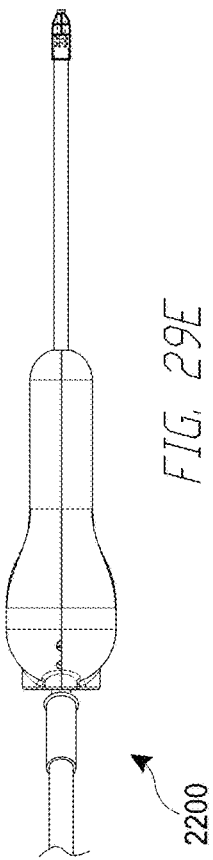
Figure 29B:
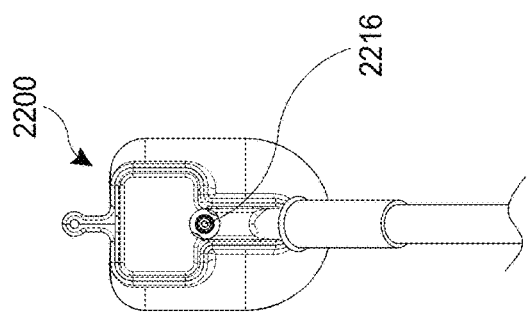
Figure 29F:
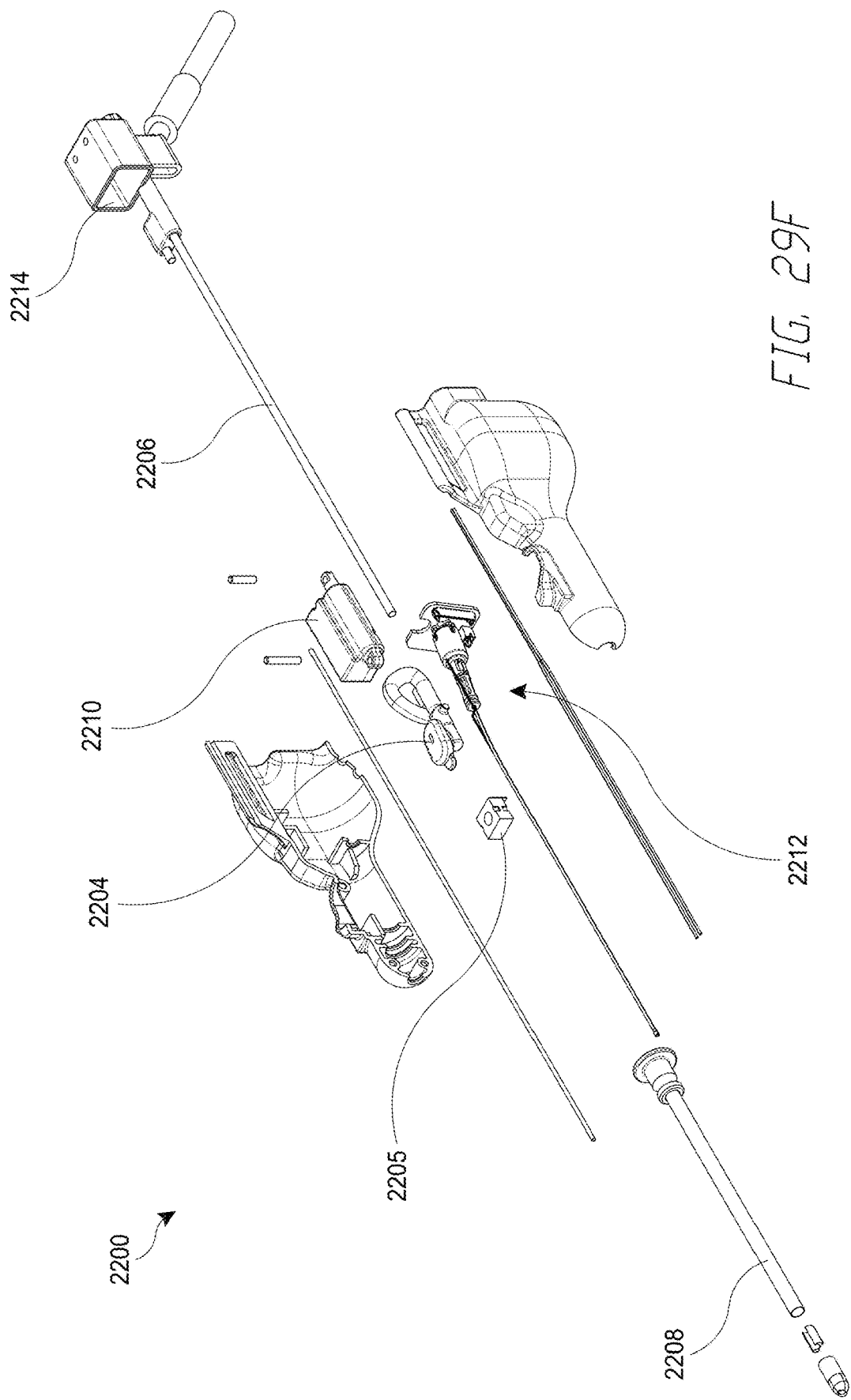
Figure 29G:
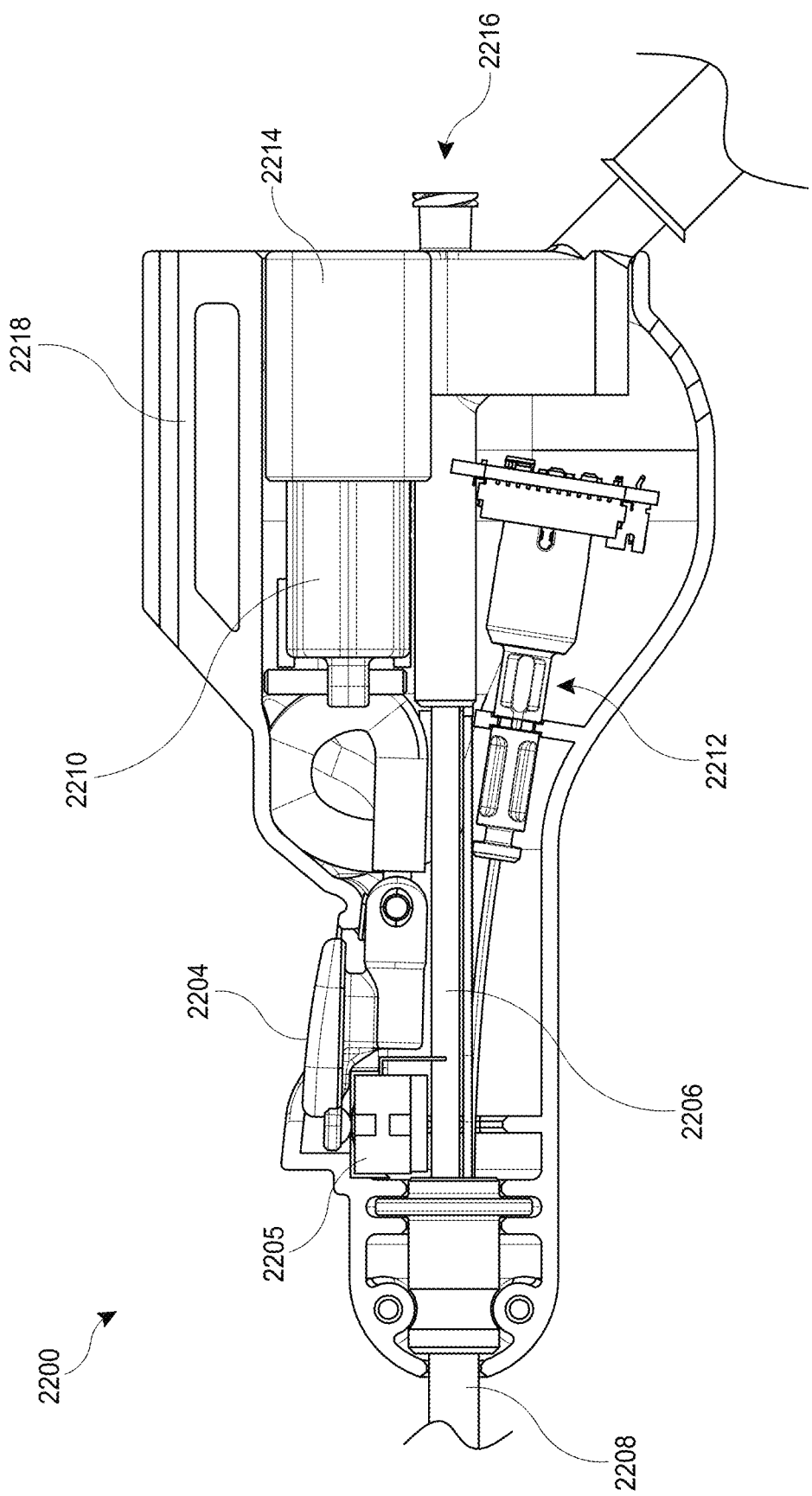

FIGS. 29A-29G depict an example of a clot evacuation device 2200. The features of the proximal end and/or handpiece 2202 of clot evacuation device 2200 will be described and may be combined with other features disclosed elsewhere herein or combined with other embodiments disclosed elsewhere herein. FIG. 29A is a perspective view of the clot evacuation device 2200. FIG. 29B is a proximal view of the clot evacuation device 2200. FIG. 29C is a top view of the clot evacuation device 2200. FIG. 29D is a side view of the clot evacuation device 2200. FIG. 29E is a bottom view of the clot evacuation device 2200. FIG. 29F is an exploded view of the clot evacuation device 2200. FIG. 29G is a side cross-sectional view of the handpiece 2202 of the clot evacuation device 2200. The handpiece 2202 may comprise an actuation button 2204 for retracting and/or extending an evacuation hypotube 2206 relative to an outer tubular body 2208, as will be described below, and as described elsewhere herein.

As shown in FIGS. 29F and 29G, the handpiece 2202 can include an electrical switch 2205, a piston assembly 2210, a visualization complex 2212, and a proximal hub 2214. The actuation button 2204 may be compressed (it may operate around a pivot) to activate the electrical switch 2205 which may be configured to actuate the piston assembly 2210. One end of the piston assembly 2210 can be fixedly secured to the proximal hub 2214 (e.g. by a pin) causing it to move upon actuation in a proximal direction (e.g. by about 10 mm) relative to the rest of the handpiece 2202 in which the other end of the piston assembly 2210 is fixedly secured (e.g. by a second pin). In an un-retracted state, the evacuation hypotube 2206 may extend distally beyond the outer tubular body 2208 and in a retracted state the outer tubular body 2208 may extend distally beyond the evacuation hypotube 2206. Retraction of the evacuation hypotube 2206 may be useful, for example, to provide an unobstructed view by the visualization device of the visualization complex 2212 and/or to bring the evacuation hypotube 2206 closer to an irrigation jet. Reactivation of the electrical switch 2205 by the actuation button 2204 may cause the proximal hub 2214 to return to its un-retracted position. In some embodiments, the actuation button 2204 may be configured to extend the evacuation hypotube 2206 distally forward and to then retract it to a normal position. In some embodiments, the distal end of the evacuation hypotube 2206 may only reach the distal end of the outer tubular body 2208 in a fully extended position. The clot evacuation device 2200 can be configured to removably receive an introducer as described elsewhere herein, which may be inserted down the evacuation hypotube 2206. The proximal hub 2214 can include a hole 2216 (FIG. 29B) through which the introducer may be inserted, which can be sealed by a plug or cover. The clot evacuation device can include a rail 2218 for mounting a surgical navigation array or other piece of instrumentation.

FIG. 30 shows an example of a clot evacuation device 2400 with a slidable button 2404 fixedly secured to the outer circumference of the evacuation hypotube 2406 along a portion of the hypotube disposed internally within the handpiece. The user may move the slidable button 2404 proximally or distally to move the evacuation hypotube 2406 in a proximal and/or distal direction with respect to the outer tubular body 2408. In some embodiments, the evacuation hypotube 2406 may be spring loaded to bias the evacuation hypotube 2406 in a certain direction (e.g. a proximal retracted position or a distal extended position).

The retraction and/or extension of the evacuation hypotubes (and in some embodiments the outer tubular bodies) in the embodiments disclosed herein may be accomplished by any suitable means and are not limited to the examples provided. Means of actuating the retraction/extension can include electric motors, electromagnetic solenoids, pneumatic pistons, cable systems, mechanical assemblies, etc. In some embodiments, the evacuation hypotube may manually extended by the user from the proximal end. The handpiece may include a sealing member (e.g., an O-ring) surrounding the evacuation hypotube within the handpiece. The retraction/extension may be accomplished by a hybrid mode of actuation. For instance, the clot evacuation device can include an automated actuation mechanism (e.g., a motor) for retracting/extending the evacuation hypotube a first larger distance (e.g., 10 mm) and also allow manual actuation of the evacuation hypotube, for example by the fingers of the user. The manual actuation may be limited to a smaller distance (e.g., 2 mm) for fine-tuning. The manual fine-tuning may allow the user to sense tactile feedback in touching tissue with the evacuation hypotube. The automated actuation may provide favorable ergonomics for moving the evacuation hypotube over larger distances. The actuation mechanism may be integrated into the handpiece or into an external component. For example, in some embodiments the retraction/extension may be operated by operation of a foot pedal operatively connected to the clot evacuation device.

The clot evacuation devices disclosed herein may also have several operable modes of retraction and/or extension. For example, the clot evacuation device may be configured to retract or extend the evacuation hypotube a first distance (e.g. a maximal distance such as 10 mm) and to oscillate the evacuation hypotube over a shorter displacement back and forth along a longitudinal direction when in a maximally extended position. The shorter displacement may be less than the distance of full retraction/extension. The evacuation hypotube may be oscillated at various speeds. Small displacement oscillations (e.g., 3 mm) may create a "pecking" motion, which may be useful for removing a blood clot. Even smaller displacement oscillations (e.g., 0.5 mm) may create a vibration effect, which also may be useful for removing a blood clot. Other modes of operation are also contemplated. In some embodiments, the clot evacuation hypotube may be extended to about 2 mm beyond the distal end of the windshield.

In many embodiments, the evacuation hypotubes and/or evacuation lumens of the clot evacuation devices disclosed herein may be used as working channels for additional instruments, similar to the way they may be used for the insertion of introducers and/or obturators. For example, bipolar devices, ultrasonic transducers, graspers, and other neurosurgical instruments which are smaller than the inner diameter of the evacuation hypotube (e.g., 2.9 mm) may be inserted through the working channel of an evacuation hypotube from the proximal end of the device. The length of the working channel may be about 280.5 mm long. These instruments, may be used, for instance, after the clot evacuation device has been inserted into the body to perform additional operations in the body. In this manner, the clot evacuation device can act as clot evacuation device and/or introducer and/or trocar/portal. The clot evacuation device can include a plug, cover, or seal located at the proximal entry point into the clot evacuation hypotube or lumen so that suction may be maintained in the evacuation hypotube or lumen during clot evacuation steps of a procedure (i.e. aspiration).

Sensors within the clot evacuation device (e.g., cameras) can be shielded from electromagnetic/RF interference (e.g., from other surgical devices inserted through the evacuation hypotube) by any suitable means. For example, shielding material and/or additional ground wires can be included in the clot evacuation device. The main data cable can be used to accommodate additional ground wires and shielding tubing. The shielding tubing and/or housing for various sensor components can comprise materials suitable for resisting electromagnetic interference, such as non-metallic materials (e.g., thin-walled plastics, polyamides) or appropriate metals (e.g., titanium). The circuit board in the handpiece can be protected from electromagnetic interference by a metallic box. Aspects of RF shielding are further described in one or more the following US patent applications, the disclosures of which are herein incorporated by reference in their entireties: US 2015/0112324, US 2015/0157387, US 2011/0276113, US 2012/0095458, and US 2010/0286477

Further examples of embodiments of the present disclosure may include:

1. A device or method for clot evacuation, particularly for treating intracranial hemorrhages, using an integrated device that provides both visualization (e.g., imaging, video and illumination) with suction and irrigation.

2. A device or method for clot evacuation, particularly for treating intracranial hemorrhages, that includes vibration or mechanical movement, such as rotational movement of a suction tube provided concentrically over a visualization element or vibration of a visualization element, to help clear the fluid from the fluid pathway.

3. A device or method for clot evacuation, particularly for treating intracranial hemorrhages, for maintaining good visualization of the clot so that a visualization element is not obstructed by bodily fluids or tissue. For example, the visualization element may be retractable within a suction channel. In other examples, irrigation can be used to clean the visualization element (such as optics) by utilizing particular arrangements of the optics and irrigation devices.

4. A device or method for clot evacuation, particularly for treating intracranial hemorrhages, which uses a visualization device having a clear and conically shaped obturator distal end that enables surgeons to see tissue as the device is moved into the clot location. For example, a separate visualization device may be provided that is removable from a clear trocar, or an integrated visualization device may be provided with a clear, conical distal window. This may be used with a separate integrated visualization/suction/irrigation device to remove the clot.

5. A device or method for clot evacuation, particularly for treating intracranial hemorrhages, wherein the obturator distal end described in feature 4 above is configured to open and allow the distal end of the clot evacuation device to extend outward toward the tissue site 6. A device or method for clot evacuation, particularly for treating intracranial hemorrhages, wherein an introducer is removably insertable within a working channel of the clot evacuation device and may be used to atraumatically insert the clot evacuation device into the body tissue. The introducer and/or the clot evacuation device may comprise additional components for shielding the operational elements of the clot evacuation device during insertion, yet allowing the operational elements to perform through the distal end of the clot evacuation device during insertion and/or upon removal of the introducer.

7. A device or method for clot evacuation, particularly for treating intracranial hemorrhages, that provides visualization and includes optical enhancements on the clot evacuation device itself to help the surgeon see where the device is going before it gets there. For example, such enhancements could help the surgeon see through the tissue, to be able to see the transition in tissue from white brain matter to the red clot. Various embodiments are contemplated, such as infrared illumination fibers, ultrasonic transducers, and other sensors (such as glucose sensors).

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described in this section or elsewhere in this specification may be embodied in a variety of other forms. Furthermore, various omissions, substitutions and changes in the form of the methods and systems described in this section or elsewhere in this specification may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth in this section or elsewhere in this specification. Accordingly, the scope of the present disclosure is not intended to be limited by the specific disclosures of preferred embodiments in this section or elsewhere in this specification, and may be defined by claims as presented in this section or elsewhere in this specification or as presented in the future.

What is claimed is:

1. A surgical device for creating an access path to an internal region of a body, of a patient, the surgical device comprising; an outer tubular body having a proximal end and a distal end; a visualization element disposed within the outer tubular body and having a distal end positioned at or near the distal end of the outer tubular body for transmitting images received from inside the body of the patient; an evacuation hypotube with a lumen configured for removable insertion of an introducer with an atraumatic tip and one or more additional instruments for performing an operation within the body of the patient disposed within the outer tubular body and having a distal end positioned at or near the distal end of the outer tubular body; a shielding member that is at least partially transparent, removably attachable to the distal end of the outer tubular body to cover the one or more additional instruments, and includes a hollow passageway; wherein the shielding member permits fluid communication between the evacuation hypotube, the visualization element, the one or more additional instruments and the hollow passageway; wherein the evacuation hypotube is configured to be proximally retractable, distally extendable, or both relative to the outer tubular body and through the hollow passageway of the shielding member; and wherein the introducer is removably extendable through the shielding member beyond the distal end of the outer tubular body to form an atraumatic distal tip, while the shielding member forms a continuous atraumatic surface between the introducer and the outer tubular body such that the surgical device may be atraumatically inserted into the body of the patient to a location where the operation is to be performed.

2. The surgical device of claim 1, wherein the evacuation hypotube is configured to provide suction that assists in clot removal.

3. The surgical device of claim 1, wherein the one or more instruments comprises an irrigation hypotube for providing fluid irrigation.

4. The surgical device of claim 1, wherein the one or more instruments comprises an illumination element for providing light to a working area disposed distally of the distal end of the outer tubular body.

5. The surgical device of claim 1, wherein the atraumatic tip of the introducer is at least partially transparent and includes an image sensor for transmitting images received from inside the body of the patient.

6. The surgical device of claim 1, wherein the the shielding member surrounds the hollow passageway on all sides.

* * * * *